United States Patent
Huizing et al.

(10) Patent No.: US 10,493,087 B2
(45) Date of Patent: Dec. 3, 2019

(54) SIALYLATION-INCREASING THERAPIES FOR DISEASES ASSOCIATED WITH OXIDATIVE STRESS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Marjan Huizing, Santa Cruz, CA (US); May C. Malicdan, Rockville, MD (US); Nuria Carrillo, Bethesda, MD (US)

(73) Assignee: The United States of America, as represented by National Institute of Health, Bethesda, MD (US)

( * ) Notice: Subject to any disclaimer, the term of this patent is extended or adjusted under 35 U.S.C. 154(b) by 0 days.

(21) Appl. No.: 15/553,561

(22) PCT Filed: Feb. 23, 2016

(86) PCT No.: PCT/US2016/019084
§ 371 (c)(1),
(2) Date: Aug. 24, 2017

(87) PCT Pub. No.: WO2016/137963
PCT Pub. Date: Sep. 1, 2016

(65) Prior Publication Data
US 2018/0235988 A1    Aug. 23, 2018

Related U.S. Application Data

(60) Provisional application No. 62/120,742, filed on Feb. 25, 2015.

(51) Int. Cl.
| | | |
|---|---|---|
| *A61K 31/7008* | (2006.01) | |
| *A61K 31/7012* | (2006.01) | |
| *A61K 31/702* | (2006.01) | |
| *A61P 9/00* | (2006.01) | |
| *A61K 45/06* | (2006.01) | |
| *A61K 31/7088* | (2006.01) | |
| *A61K 9/00* | (2006.01) | |
| *A61K 9/127* | (2006.01) | |
| *A61K 9/50* | (2006.01) | |
| *A61K 47/20* | (2006.01) | |

(52) U.S. Cl.
CPC ........ *A61K 31/7008* (2013.01); *A61K 9/0053* (2013.01); *A61K 9/127* (2013.01); *A61K 9/50* (2013.01); *A61K 31/702* (2013.01); *A61K 31/7012* (2013.01); *A61K 31/7088* (2013.01); *A61K 45/06* (2013.01); *A61K 47/20* (2013.01); *A61P 9/00* (2018.01)

(58) Field of Classification Search
CPC .................... A61P 9/00–14; A61K 31/7008
See application file for complete search history.

(56) References Cited

U.S. PATENT DOCUMENTS

| | | | |
|---|---|---|---|
| 2010/0249047 A1* | 9/2010 | Huizing | ............. A61K 31/7012 514/25 |
| 2011/0212917 A1 | 9/2011 | Shiota et al. | |
| 2011/0301103 A1 | 12/2011 | Chugh | |
| 2012/0142619 A1 | 6/2012 | Jin et al. | |
| 2013/0058998 A1 | 3/2013 | Huizing et al. | |
| 2014/0037658 A1 | 2/2014 | Nilsson et al. | |

FOREIGN PATENT DOCUMENTS

| | | |
|---|---|---|
| JP | 2006 265210 | 10/2006 |
| WO | WO 95/33484 | 12/1995 |
| WO | WO 2008/150477 | 12/2008 |
| WO | WO 2014/160018 | 10/2014 |
| WO | WO 2014/194053 | 12/2014 |
| WO | WO 2016/137963 | 9/2016 |

OTHER PUBLICATIONS

Chai, Y. et al "Hereditary inclusion-body myopathy associated with cardiomyopathy . . . " Muscle & Nerve, pp. 133-136. (Year: 2011).*
Cardinale, D. et al "Anthracycline-induced cardiomyopathy" J. Am. Coll. Cardiol., vol. 55, No. 3, pp. 213-220. (Year: 2010).*
Wu, X. et al "N-acetylcysteine reduces oxidative stress . . . " Mol. Med. Rep., vol. 10, pp. 615-624. (Year: 2014).*
Liberopoulos, E. et al "Early statin therapy in patients . . . " Hellenic J. Cardiol., vol. 46, pp. 5-8. (Year: 2005).*
Rosenson, R. "Statins in atherosclerosis . . . " Atherosclerosis, vol. 173, pp. 1-12. (Year: 2004).*
Cho et al., "Sialic acid deficiency is associated with oxidative stress leading to muscle atrophy and weakness in the GNE myopathy," *Human Molecular Genetics* 26(16): 3081-3093 (Advance Access publication May 13, 2017).
AN 2007-085923, X1)002758095, *Daiabase WPI Week 200709*, Thomson Scientific Ltd., London, GB, Oct. 5, 2006.
Bhavanandan et al., "Identification of the glycosidically bound sialic acid in mucin glycoproteins that reacts as 'free sialic acid' in the Warren assay," *Glycobiology* 8(11): 1077-1086 (Nov. 1, 1998).
Cho et al., "GP 27 Muscle atrophy in the GNE myopathy mouse model is associated with oxidative stress," Abstract G.P. 27, *Neuromuscular Disorders* 22(9): 816 (Oct. 1, 2012). Abstract only.
Cho et al., "P.3.6 Antioxidant capacity is impaired hyposialylated myotubes of GNE myopathy," Abstract P.3.6, *Neuromuscular Disorders* 23(9): 757 (Oct. 1, 2013). Abstract only.
Eguchi et al., "Modification of oligosaccharides by reactive oxygen species decreases sialyl lewis x-mediated cell adhesion," *Glycobiology* 15(11): 1094-1101 (Jul. 6, 2005).

(Continued)

*Primary Examiner* — Leigh C Maier
(74) *Attorney, Agent, or Firm* — Klarquist Sparkman, LLP

(57) ABSTRACT

Methods are disclosed for treating a subject with a vascular or cardiac disorder associated with oxidative stress. Methods are disclosed for treating a subject with GNE myopathy that has impaired cardiac function. These methods include administering to the subject a therapeutically effective amount of a acid, or one or more sialylated compounds, mannosamine, N-acetyl mannosamine or a derivative thereof. In other embodiments, methods are disclosed for detecting a disorder associated with oxidative stress.

18 Claims, 26 Drawing Sheets

(56) References Cited

OTHER PUBLICATIONS

Goldman et al., "Myocardial levels of sialic acid are increased in patients with heart failure secondary to coronary artery disease," *European Heart Journal* 17: 475 (Aug. 1, 2009). Abstract only.
Gopaul et al., "Sialic acid: a novel marker of cardiovascular disease?," *Clinical Biochemistry* 39(7): 667-681 (Jul. 1, 2006).
Iijima et al., "Characterization of the reaction between sialic acid (N-acetylneuraminic acid) and hydrogen peroxide," *Biological and Pharmaceutical Bulletin* 30(3): 580-582 (published online Dec. 22, 2006).
Iijima et al., "Novel biological function of sialic acid (N-acetylneuraminic acid) as a hydrogen peroxide scavenger," *FEBS Letters* 561(1-3): 163-166 (published online Feb. 23, 2004).
International Search Report from the parent PCT Application No. PCT/US2016/019084, 7 pages (dated Aug. 9, 2016).
Leoyklang et al., "Sialylation of Thomsen-Friedenreich antigen is a noninvasive blood-based bimarker for GNE myopathy," *Biomarkers* 8(5): 641-652 (Jun. 8, 2014).
Malicdan et al., "A GNE knockout mouse expressing human V572L mutation develops features similar to distal myopathy with rimmed vacuoles or hereditary inclusion body myopathy, " *Human Molecular Genetics* 16(2): 115-128 (Dec. 12, 2006).
Malicdan et al., "Prophylactic treatment with sialic acid metabolites precludes the development of the myopathic phenotype in the DMRV-hIBM mouse model," *Nature Medicine* 15(6): 690-695 (published online May 17, 2009).
Manoli et al., "Targeting proximal tubule mitochondrial dysfunction attenuates the renal disease of methylmalonic academia," *Proceedings of the National Academy of Sciences* 110(33): 13552-13557 (Aug. 13, 2013).
Nagasawa et al., "N-acetyl-d-mannosaminetreatment alleviates age-related decline in place-learning ability in dogs," *Journal of Veterinary Medical Science*, Advance Publication, 76(5): 757-761 (Advance Publication published online Jan. 16, 2014).
Serdar et al., "The relation between oxidant and antioxidant parameters and severity of acute coronary syndromes," *Acta Cardiologica* 62(4): 373-380 (Jul. 31, 2007).
Written Opinion from the parent PCT Application No. PCT/US2016/019084, 12 pages (dated Aug. 9, 2016).
Yonekawa et al., "Sialyllactose ameliorates myopathic phenotypes in symptomatic GNE myopathy model mice," *Brain* 137(10): 2670-2679 (Jul. 24, 2014).
Malicdan and Nishino, "Perspectives on Distal myopathy with rimmed vacuoles or hereditary inclusion body myopathy: contributions from an animal model. Lack of sialic acid, a central determinant in sugar chains, causes myopathy?," *Acta Myologica* XXVI: 171-175 (2007).

* cited by examiner

FIG. 2A
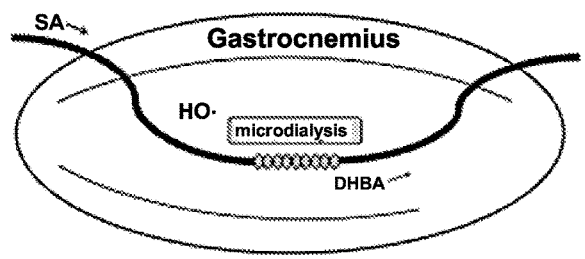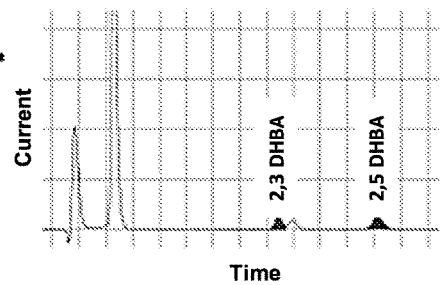
FIG. 2B
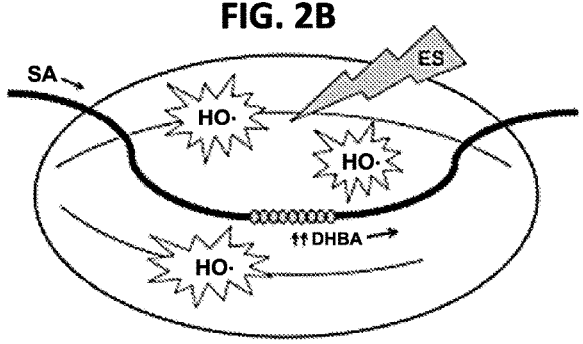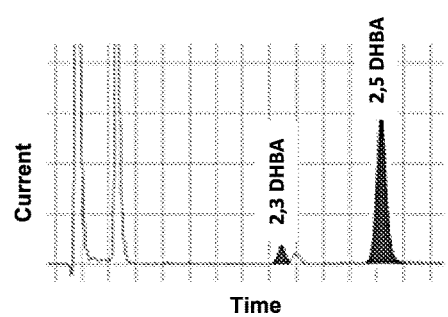
FIG. 2C
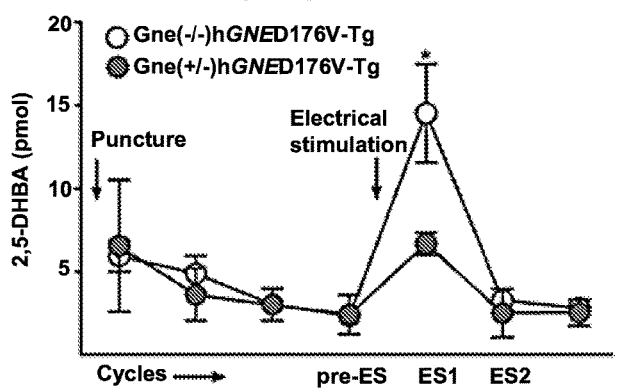
FIG. 2D
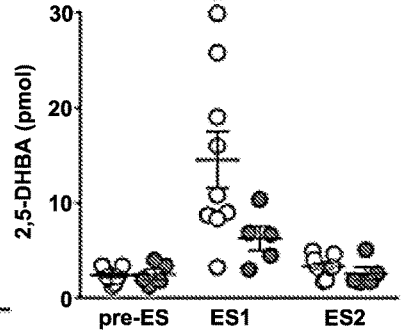

FIG. 3A
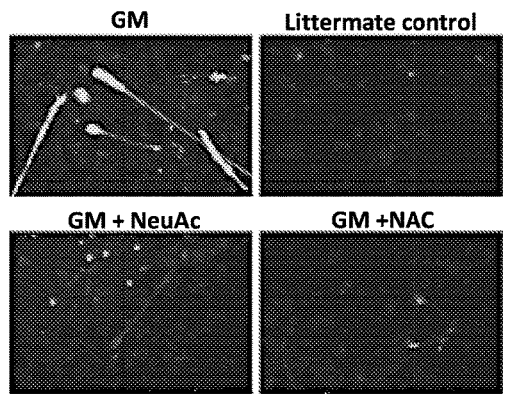
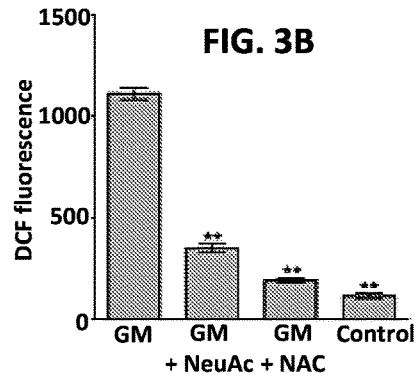
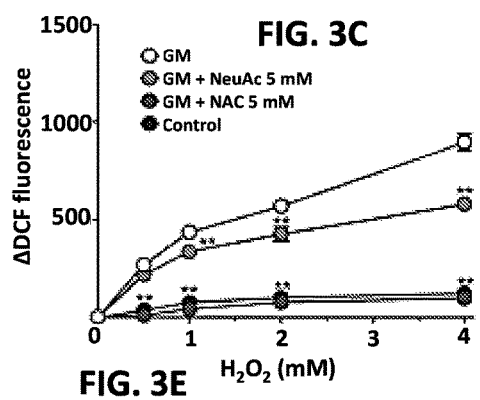
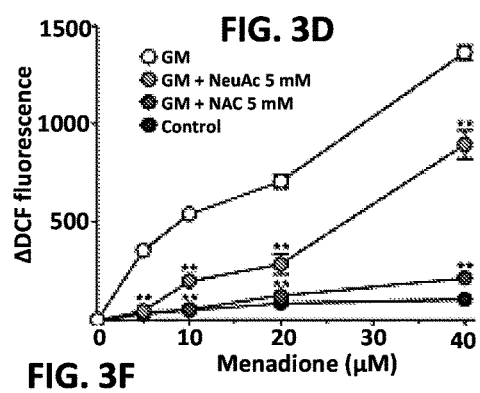
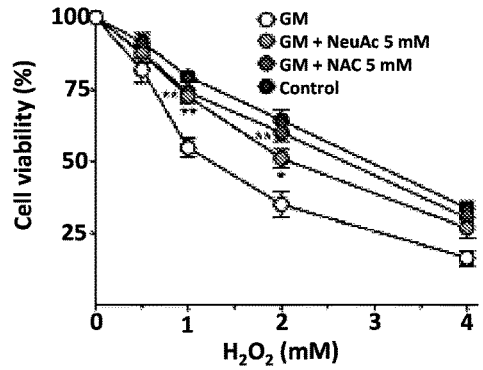
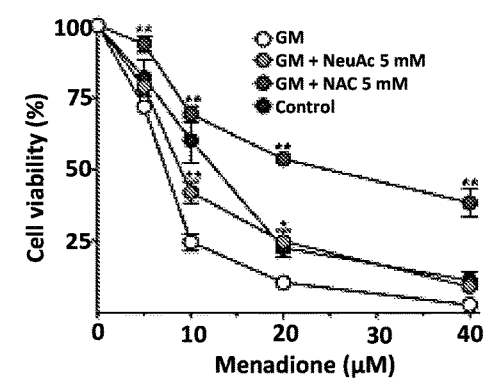

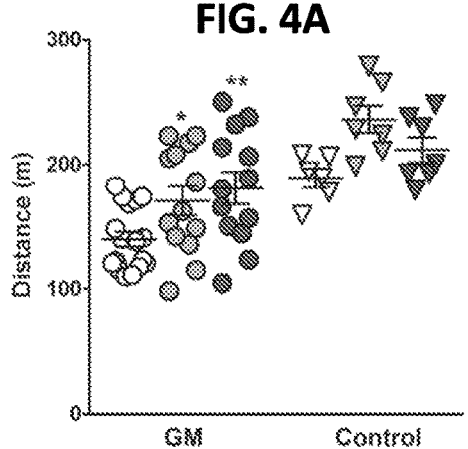
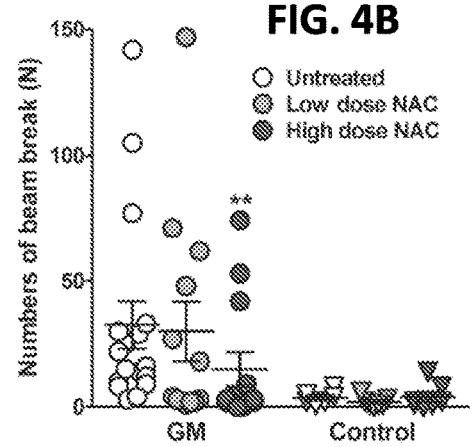
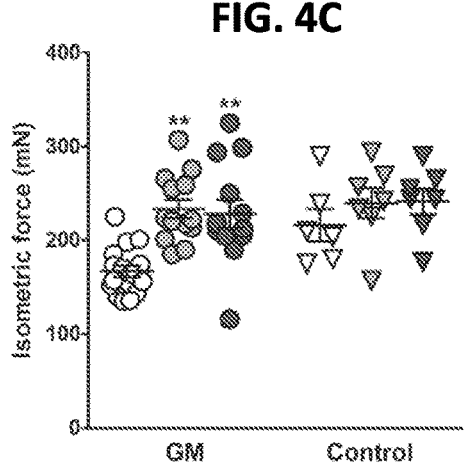
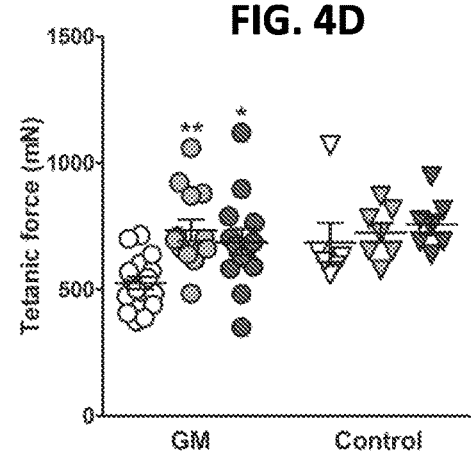
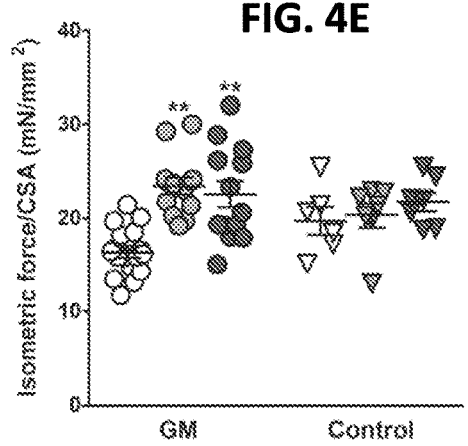
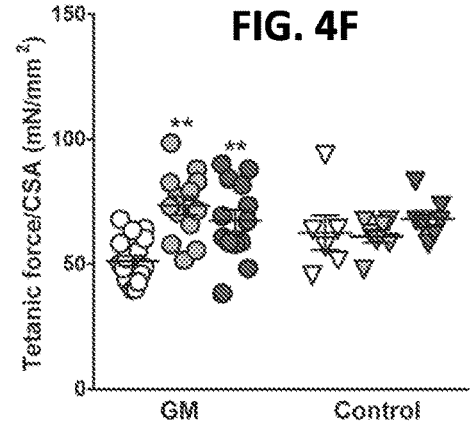

Table 1

Changes in muscle atrophy related genes expression in Gne⁻/⁻hGNED176V-Tg mice analyzed by microarray

| Gene Symbol | Average Intensity | | Ratio (G/L) | p-value |
|---|---|---|---|---|
| | Gne⁻/⁻hGNED176V-Tg (G) | Gne⁺/⁻hGNED176V-Tg (L) | | |
| Akt1 | 85.362 | 69.558 | 1.227 | 0.073 |
| Amfr | 204.682 | 182.763 | 1.120 | 0.177 |
| Anapc11 | 83.798 | 100.209 | 0.836 | 0.092 |
| Anapc16 | 129.161 | 158.520 | 0.815 | 0.062 |
| Apc | 81.308 | 65.174 | 1.248 | 0.057 |
| Arih1 | 68.769 | 60.847 | 1.130 | 0.462 |
| Arrb1 | 24.332 | 28.621 | 0.850 | 0.156 |
| Arrb1 | 22.461 | 25.646 | 0.876 | 0.285 |
| Atg3 | 148.747 | 153.902 | 0.967 | 0.622 |
| Atg4b | 82.019 | 84.790 | 0.967 | 0.598 |
| Axin1 | 29.489 | 27.618 | 1.068 | 0.497 |
| Birc6 | 77.269 | 69.776 | 1.107 | 0.201 |
| Birc6 | 13.954 | 10.520 | 1.327 | 0.080 |
| Birc7 | 15.666 | 14.226 | 1.101 | 0.491 |
| Brap | 21.584 | 22.545 | 0.957 | 0.628 |
| Brca1 | 17.442 | 8.818 | 1.978 | 0.025 |
| Btrc | 58.449 | 56.718 | 1.031 | 0.398 |
| Cand1 | 59.057 | 45.466 | 1.299 | 0.184 |
| Cblb | 61.749 | 49.984 | 1.235 | 0.340 |
| Ccnf | 43.132 | 42.035 | 1.026 | 0.821 |
| Ccnf | 180.709 | 175.198 | 1.031 | 0.806 |
| Cdc34 | 83.265 | 98.263 | 0.847 | 0.106 |
| Crbn | 111.690 | 100.210 | 1.115 | 0.326 |
| Cul1 | 113.322 | 107.485 | 1.054 | 0.594 |
| Cul1 | 124.978 | 113.982 | 1.096 | 0.040 |
| Cul3 | 1010.376 | 966.489 | 1.045 | 0.607 |
| Cul4a | 110.009 | 110.050 | 1.000 | 0.949 |
| Cul4a | 11.405 | 7.207 | 1.582 | 0.246 |
| Cul4b | 14.074 | 10.726 | 1.312 | 0.118 |
| Cyhr1 | 131.761 | 173.670 | 0.759 | 0.002 |
| Cyhr1 | 104.861 | 122.284 | 0.858 | 0.073 |
| Ddb1 | 249.554 | 204.955 | 1.218 | 0.183 |
| Egln2 | 187.486 | 199.457 | 0.940 | 0.265 |
| Fbxl14 | 49.372 | 44.164 | 1.118 | 0.470 |
| Fbxl15 | 30.685 | 36.989 | 0.830 | 0.065 |
| Fbxl3 | 17.795 | 15.365 | 1.158 | 0.565 |
| Fbxl5 | 13.857 | 15.769 | 0.879 | 0.431 |
| Fbxo2 | 27.204 | 28.005 | 0.971 | 0.727 |

FIG. 6A

| | | | | |
|---|---|---|---|---|
| Fbxo25 | 32.376 | 31.864 | 1.016 | 0.977 |
| Fbxo30 | 16.730 | 18.332 | 0.913 | 0.321 |
| Fbxo30 | 43.590 | 40.837 | 1.067 | 0.682 |
| Fbxo32 | 1028.212 | 475.260 | 2.163 | 0.170 |
| Fbxo40 | 579.046 | 505.343 | 1.146 | 0.365 |
| Fbxo45 | 81.247 | 92.435 | 0.879 | 0.145 |
| Fbxw11 | 120.775 | 134.133 | 0.900 | 0.107 |
| Fbxw11 | 21.718 | 21.049 | 1.032 | 0.564 |
| Fbxw5 | 97.531 | 117.526 | 0.830 | 0.054 |
| Fbxw7 | 58.501 | 74.144 | 0.789 | 0.007 |
| Fem1b | 30.891 | 28.974 | 1.066 | 0.324 |
| Fzr1 | 51.419 | 54.904 | 0.937 | 0.368 |
| Gja1 | 32.078 | 28.321 | 1.133 | 0.293 |
| Gpc3 | 16.670 | 18.489 | 0.902 | 0.290 |
| Gpc3 | 16.803 | 17.869 | 0.940 | 0.575 |
| Gpc3 | 13.100 | 13.024 | 1.006 | 0.837 |
| Hectd1 | 352.869 | 298.582 | 1.182 | 0.098 |
| Hectd2 | 239.211 | 271.276 | 0.882 | 0.114 |
| Hecw1 | 58.925 | 58.512 | 1.007 | 0.973 |
| Hecw2 | 46.346 | 38.341 | 1.209 | 0.239 |
| Hecw2 | 20.219 | 16.385 | 1.234 | 0.037 |
| Herc2 | 184.994 | 167.317 | 1.106 | 0.279 |
| Herc3 | 22.676 | 35.167 | 0.645 | 0.043 |
| Herc4 | 19.251 | 24.436 | 0.788 | 0.097 |
| Herc4 | 10.354 | 9.725 | 1.065 | 0.888 |
| Herc4 | 31.654 | 29.215 | 1.084 | 0.585 |
| Huwe1 | 103.744 | 96.469 | 1.075 | 0.466 |
| Ier3 | 78.003 | 53.414 | 1.460 | 0.075 |
| Itch | 18.162 | 20.263 | 0.896 | 0.089 |
| Itch | 62.087 | 59.771 | 1.039 | 0.734 |
| Kcmf1 | 953.903 | 931.889 | 1.024 | 0.911 |
| Kctd13 | 28.798 | 31.890 | 0.903 | 0.067 |
| Klhl13 | 19.302 | 21.278 | 0.907 | 0.411 |
| Klhl20 | 239.750 | 238.512 | 1.005 | 0.950 |
| Klhl21 | 137.841 | 124.176 | 1.110 | 0.754 |
| Klhl9 | 342.208 | 302.967 | 1.130 | 0.022 |
| Lnx1 | 16.130 | 16.990 | 0.949 | 0.629 |
| Lnx1 | 10.899 | 9.975 | 1.093 | 0.907 |
| Malt1 | 222.856 | 214.319 | 1.040 | 0.417 |
| Malt1 | 120.893 | 115.395 | 1.048 | 0.715 |
| Malt1 | 70.313 | 62.885 | 1.118 | 0.428 |
| Mapk15 | 35.180 | 38.846 | 0.906 | 0.312 |
| March2 | 70.819 | 82.647 | 0.857 | 0.050 |
| March2 | 22.010 | 23.216 | 0.948 | 0.485 |
| March2 | 81.339 | 75.451 | 1.078 | 0.491 |

FIG. 6B

| | | | | |
|---|---|---|---|---|
| March4 | 8.164 | 7.099 | 1.150 | 0.657 |
| March5 | 345.316 | 374.920 | 0.921 | 0.130 |
| March6 | 34.939 | 34.527 | 1.012 | 0.976 |
| March6 | 87.111 | 84.335 | 1.033 | 0.752 |
| March6 | 128.635 | 121.045 | 1.063 | 0.678 |
| March8 | 27.330 | 27.180 | 1.006 | 0.975 |
| March8 | 44.395 | 39.702 | 1.118 | 0.147 |
| Mdm2 | 19.784 | 15.415 | 1.283 | 0.095 |
| Mgrn1 | 68.345 | 73.988 | 0.924 | 0.268 |
| Mib1 | 17.020 | 9.754 | 1.745 | 0.065 |
| Mib2 | 49.962 | 54.104 | 0.923 | 0.305 |
| Mul1 | 67.135 | 74.829 | 0.897 | 0.101 |
| Mylip | 78.192 | 78.285 | 0.999 | 0.898 |
| Ndfip1 | 217.842 | 207.193 | 1.051 | 0.454 |
| Nedd4 | 59.414 | 58.259 | 1.020 | 0.798 |
| Nedd4 | 20.476 | 18.676 | 1.096 | 0.285 |
| Nedd4 | 196.642 | 163.189 | 1.205 | 0.192 |
| Nedd4l | 40.480 | 40.400 | 1.002 | 0.935 |
| Nub1 | 101.499 | 89.085 | 1.139 | 0.333 |
| Os9 | 47.530 | 40.527 | 1.173 | 0.158 |
| Park2 | 8.565 | 6.220 | 1.377 | 0.205 |
| Pcnp | 325.311 | 337.577 | 0.964 | 0.625 |
| Pdzrn3 | 82.362 | 76.073 | 1.083 | 0.610 |
| Pdzrn3 | 13.777 | 11.803 | 1.167 | 0.765 |
| Pja2 | 17.992 | 19.353 | 0.930 | 0.498 |
| Pja2 | 19.017 | 20.243 | 0.939 | 0.446 |
| Pja2 | 332.472 | 318.175 | 1.045 | 0.604 |
| Plk1 | 7.232 | 5.012 | 1.443 | 0.452 |
| Ppil2 | 46.995 | 46.424 | 1.012 | 0.919 |
| Prpf19 | 208.009 | 193.798 | 1.073 | 0.322 |
| Rbbp6 | 19.505 | 22.864 | 0.853 | 0.234 |
| Rbbp6 | 132.733 | 128.300 | 1.035 | 0.558 |
| Rbbp6 | 75.931 | 68.995 | 1.101 | 0.551 |
| Rbx1 | 553.500 | 651.949 | 0.849 | 0.112 |
| Rbx1 | 33.500 | 34.628 | 0.967 | 0.747 |
| Rchy1 | 134.923 | 152.758 | 0.883 | 0.018 |
| Rchy1 | 9.784 | 6.657 | 1.470 | 0.038 |
| Rfwd3 | 33.570 | 33.997 | 0.987 | 0.816 |
| Rlim | 22.176 | 22.767 | 0.974 | 0.752 |
| Rlim | 10.721 | 8.512 | 1.260 | 0.402 |
| Rnf103 | 60.028 | 49.970 | 1.201 | 0.121 |
| Rnf11 | 302.230 | 341.906 | 0.884 | 0.204 |
| Rnf111 | 12.530 | 12.147 | 1.032 | 0.893 |
| Rnf130 | 189.437 | 184.637 | 1.026 | 0.814 |
| Rnf135 | 21.480 | 22.527 | 0.954 | 0.579 |

FIG. 6C

| | | | | |
|---|---|---|---|---|
| Rnf139 | 305.614 | 322.523 | 0.948 | 0.368 |
| Rnf139 | 42.087 | 44.241 | 0.951 | 0.601 |
| Rnf139 | 45.547 | 45.851 | 0.993 | 0.989 |
| Rnf144b | 30.483 | 33.720 | 0.904 | 0.491 |
| Rnf144b | 27.591 | 24.199 | 1.140 | 0.238 |
| Rnf144b | 7.852 | 4.167 | 1.884 | 0.066 |
| Rnf151 | 10.388 | 9.790 | 1.061 | 0.819 |
| Rnf213 | 106.955 | 98.656 | 1.084 | 0.651 |
| Rnf220 | 113.697 | 124.741 | 0.911 | 0.107 |
| Rnf220 | 16.107 | 16.545 | 0.974 | 0.728 |
| Rnf220 | 12.401 | 12.305 | 1.008 | 0.960 |
| Rnf220 | 174.949 | 172.994 | 1.011 | 0.908 |
| Rnf220 | 35.074 | 33.988 | 1.032 | 0.787 |
| Rnf25 | 57.964 | 62.902 | 0.922 | 0.207 |
| Rnf34 | 5.851 | 5.730 | 1.021 | 0.436 |
| Rnf34 | 88.318 | 78.195 | 1.129 | 0.377 |
| Rnf40 | 68.522 | 70.304 | 0.975 | 0.708 |
| Rnf41 | 73.293 | 77.838 | 0.942 | 0.373 |
| Rnf41 | 88.097 | 88.558 | 0.995 | 0.876 |
| Rnf6 | 346.902 | 293.073 | 1.184 | 0.153 |
| Rnf8 | 25.718 | 29.343 | 0.876 | 0.092 |
| Rnf8 | 15.307 | 13.383 | 1.144 | 0.257 |
| Sgsm3 | 20.659 | 30.422 | 0.679 | 0.001 |
| Siah1a | 18.627 | 21.479 | 0.867 | 0.395 |
| Siah1b | 7.268 | 6.185 | 1.175 | 0.593 |
| Siah2 | 29.315 | 38.781 | 0.756 | 0.027 |
| Sirt1 | 77.043 | 63.466 | 1.214 | 0.028 |
| Skp1a | 1110.940 | 1118.617 | 0.993 | 0.895 |
| Smurf1 | 21.738 | 25.575 | 0.850 | 0.052 |
| Smurf1 | 13.682 | 14.192 | 0.964 | 0.746 |
| Smurf2 | 42.310 | 46.830 | 0.903 | 0.271 |
| Smurf2 | 21.626 | 21.730 | 0.995 | 0.840 |
| Snx1 | 20.830 | 17.054 | 1.221 | 0.377 |
| Socs7 | 86.393 | 87.887 | 0.983 | 0.818 |
| Sox17 | 5.933 | 6.018 | 0.986 | 0.992 |
| Sox17 | 45.969 | 36.076 | 1.274 | 0.098 |
| Sox9 | 11.049 | 9.524 | 1.160 | 0.476 |
| Tnfaip1 | 58.770 | 67.414 | 0.872 | 0.163 |
| Tnfaip3 | 95.878 | 94.392 | 1.016 | 0.848 |
| Tnk2 | 23.077 | 34.743 | 0.664 | 0.004 |
| Topors | 95.065 | 116.691 | 0.815 | 0.154 |
| Topors | 18.338 | 18.262 | 1.004 | 0.983 |
| Traf3 | 45.942 | 57.052 | 0.805 | 0.033 |
| Traf4 | 47.592 | 51.609 | 0.922 | 0.384 |
| Traf4 | 29.738 | 26.305 | 1.130 | 0.646 |

FIG. 6D

| | | | | |
|---|---|---|---|---|
| Traf7 | 115.996 | 120.438 | 0.963 | 0.221 |
| Trib3 | 68.206 | 69.855 | 0.976 | 0.697 |
| Trib3 | 16.793 | 12.753 | 1.317 | 0.072 |
| Trim21 | 20.682 | 19.362 | 1.068 | 0.675 |
| Trim24 | 214.895 | 265.885 | 0.808 | 0.154 |
| Trim25 | 68.387 | 49.220 | 1.389 | 0.014 |
| Trim28 | 159.480 | 143.215 | 1.114 | 0.228 |
| Trim28 | 16.452 | 12.813 | 1.284 | 0.044 |
| Trim32 | 86.342 | 102.208 | 0.845 | 0.004 |
| Trim33 | 50.538 | 51.176 | 0.988 | 0.846 |
| Trim33 | 230.206 | 231.488 | 0.994 | 0.913 |
| Trim33 | 16.201 | 15.043 | 1.077 | 0.598 |
| Trim8 | 70.831 | 71.978 | 0.984 | 0.731 |
| Trim9 | 10.250 | 12.130 | 0.845 | 0.342 |
| Uba6 | 29.648 | 31.121 | 0.953 | 0.492 |
| Uba6 | 30.057 | 30.986 | 0.970 | 0.924 |
| Ube2c | 45.508 | 29.020 | 1.568 | 0.135 |
| Ube2d1 | 1057.041 | 1063.233 | 0.994 | 0.866 |
| Ube2d2 | 234.317 | 217.680 | 1.076 | 0.446 |
| Ube2d2 | 3007.810 | 2437.272 | 1.234 | 0.238 |
| Ube2d3 | 34.382 | 38.709 | 0.888 | 0.194 |
| Ube2d3 | 724.629 | 721.338 | 1.005 | 0.939 |
| Ube2e1 | 192.020 | 205.577 | 0.934 | 0.272 |
| Ube2g1 | 278.315 | 282.235 | 0.986 | 0.870 |
| Ube2g1 | 27.461 | 27.269 | 1.007 | 0.987 |
| Ube2g1 | 37.361 | 32.293 | 1.157 | 0.244 |
| Ube2l3 | 248.237 | 278.250 | 0.892 | 0.139 |
| Ube2l6 | 27.974 | 30.396 | 0.920 | 0.418 |
| Ube2m | 319.485 | 327.230 | 0.976 | 0.858 |
| Ube2n | 74.188 | 89.802 | 0.826 | 0.040 |
| Ube2o | 46.882 | 45.425 | 1.032 | 0.811 |
| Ube2q1 | 55.293 | 57.488 | 0.962 | 0.650 |
| Ube2ql1 | 34.704 | 28.219 | 1.230 | 0.237 |
| Ube2z | 65.193 | 67.589 | 0.965 | 0.567 |
| Ube3b | 467.307 | 420.111 | 1.112 | 0.334 |
| Ube3c | 129.802 | 129.247 | 1.004 | 0.979 |
| Ube4b | 48.449 | 42.803 | 1.132 | 0.129 |
| Ubox5 | 64.492 | 63.427 | 1.017 | 0.927 |
| Ubr7 | 168.652 | 153.720 | 1.097 | 0.064 |
| Uhrf2 | 45.169 | 39.161 | 1.153 | 0.335 |
| Uhrf2 | 71.981 | 56.675 | 1.270 | 0.048 |
| Vcp | 467.263 | 510.540 | 0.915 | 0.032 |
| Vcpip1 | 20.930 | 18.322 | 1.142 | 0.117 |
| Vhl | 16.767 | 17.012 | 0.986 | 0.971 |
| Wdsub1 | 101.764 | 105.117 | 0.968 | 0.604 |

FIG. 6E

| | | | | |
|---|---|---|---|---|
| Wwp1 | 76.951 | 79.190 | 0.972 | 0.703 |
| Wwp1 | 526.046 | 475.817 | 1.106 | 0.270 |
| Zer1 | 252.629 | 225.505 | 1.120 | 0.396 |

FIG. 6F

Table 2

Changes in oxidative stress and redox homeostasis related genes expression in Gne⁻/⁻ hGNED176V-Tg mice analyzed by microarray

| Gene Symbol | Average Intensity | | Ratio (G/L) | p-value |
|---|---|---|---|---|
| | Gne⁻/⁻hGNED176V-Tg (G) | Gne⁺/⁻hGNED176V-Tg (L) | | |
| Abcc1 | 16.309 | 20.351 | 0.801 | 0.043 |
| Abcc1 | 69.968 | 68.503 | 1.021 | 0.779 |
| Adh5 | 131.686 | 137.427 | 0.958 | 0.372 |
| Adrbk1 | 148.733 | 142.922 | 1.041 | 0.560 |
| Adrbk1 | 12.215 | 9.584 | 1.275 | 0.342 |
| Agap3 | 103.403 | 99.434 | 1.040 | 0.224 |
| Aifm1 | 156.543 | 150.671 | 1.039 | 0.485 |
| Aldh1a1 | 683.513 | 718.879 | 0.951 | 0.626 |
| Aldh3a2 | 36.844 | 34.916 | 1.055 | 0.629 |
| Aldh5a1 | 45.307 | 51.583 | 0.878 | 0.248 |
| Als2 | 55.352 | 65.582 | 0.844 | 0.194 |
| Apex1 | 112.273 | 128.003 | 0.877 | 0.102 |
| Apod | 43.335 | 46.816 | 0.926 | 0.542 |
| Apod | 191.614 | 158.545 | 1.209 | 0.107 |
| Atox1 | 93.532 | 89.684 | 1.043 | 0.876 |
| Atrn | 16.309 | 13.138 | 1.241 | 0.104 |
| Bcl2 | 68.532 | 67.136 | 1.021 | 0.800 |
| Bcl2 | 18.226 | 16.722 | 1.090 | 0.596 |
| Btk | 5.956 | 1.865 | 3.193 | 0.039 |
| Camk2g | 383.176 | 411.369 | 0.931 | 0.297 |
| Camk2g | 7.306 | 7.777 | 0.939 | 0.802 |
| Car3 | 2711.234 | 1968.868 | 1.377 | 0.146 |
| Cat | 9.797 | 9.065 | 1.081 | 0.796 |
| Cat | 406.462 | 345.098 | 1.176 | 0.034 |
| Chrna4 | 14.599 | 19.068 | 0.766 | 0.042 |
| Coq7 | 158.903 | 210.045 | 0.757 | 0.364 |
| Crygd | 92.364 | 94.834 | 0.974 | 0.704 |
| Cst3 | 2096.927 | 2177.208 | 0.963 | 0.673 |
| Cth | 13.006 | 15.074 | 0.863 | 0.426 |
| Ctns | 41.079 | 28.265 | 1.453 | 0.048 |
| Cycs | 1597.618 | 1761.899 | 0.907 | 0.428 |
| Cygb | 107.795 | 87.077 | 1.238 | 0.104 |
| Ddit3 | 57.150 | 65.509 | 0.872 | 0.344 |
| Dgkk | 117.932 | 105.134 | 1.122 | 0.063 |
| Dld | 365.375 | 369.138 | 0.990 | 0.843 |
| Dnajc10 | 16.379 | 16.266 | 1.007 | 0.867 |
| Dnajc10 | 73.141 | 60.898 | 1.201 | 0.203 |
| Egln2 | 187.486 | 199.457 | 0.940 | 0.265 |

FIG. 6G

| | | | | |
|---|---|---|---|---|
| Epas1 | 12.742 | 13.989 | 0.911 | 0.603 |
| Epas1 | 22.794 | 22.351 | 1.020 | 0.930 |
| Epas1 | 18.080 | 16.643 | 1.086 | 0.601 |
| Epx | 20.291 | 19.581 | 1.036 | 0.875 |
| Ercc1 | 43.987 | 51.277 | 0.858 | 0.087 |
| Ercc2 | 9.183 | 8.090 | 1.135 | 0.631 |
| Ercc3 | 24.349 | 21.720 | 1.121 | 0.289 |
| Ercc6 | 30.208 | 31.100 | 0.971 | 0.856 |
| Ercc8 | 178.103 | 189.594 | 0.939 | 0.388 |
| Erp44 | 129.580 | 145.760 | 0.889 | 0.348 |
| Etfdh | 398.933 | 357.037 | 1.117 | 0.251 |
| Fgf8 | 20.327 | 22.185 | 0.916 | 0.743 |
| Fos | 163.221 | 179.493 | 0.909 | 0.679 |
| G6pdx | 43.499 | 28.660 | 1.518 | 0.012 |
| Gab1 | 15.800 | 15.014 | 1.052 | 0.632 |
| Gab1 | 50.508 | 42.278 | 1.195 | 0.369 |
| Gab1 | 22.881 | 18.535 | 1.234 | 0.238 |
| Gclc | 53.312 | 51.370 | 1.038 | 0.838 |
| Gclc | 24.863 | 23.892 | 1.041 | 0.761 |
| Gclm | 106.202 | 123.691 | 0.859 | 0.174 |
| Ggt5 | 28.270 | 24.729 | 1.143 | 0.271 |
| Ggt6 | 32.842 | 33.951 | 0.967 | 0.635 |
| Ggt7 | 16.099 | 19.317 | 0.833 | 0.301 |
| Glo1 | 533.754 | 565.464 | 0.944 | 0.736 |
| Glrx | 74.310 | 95.058 | 0.782 | 0.018 |
| Glrx2 | 221.728 | 260.697 | 0.851 | 0.088 |
| Glrx3 | 692.716 | 745.806 | 0.929 | 0.257 |
| Glrx5 | 357.949 | 445.758 | 0.803 | 0.074 |
| Gpx1 | 273.777 | 244.858 | 1.118 | 0.590 |
| Gpx4 | 735.843 | 765.534 | 0.961 | 0.573 |
| Gpx7 | 35.137 | 37.324 | 0.941 | 0.623 |
| Gsr | 56.343 | 77.095 | 0.731 | 0.131 |
| Gsr | 11.259 | 12.675 | 0.888 | 0.439 |
| Gss | 32.774 | 29.729 | 1.102 | 0.399 |
| Gstk1 | 70.453 | 83.397 | 0.845 | 0.310 |
| Gstm2 | 108.202 | 95.290 | 1.136 | 0.666 |
| Gstt3 | 231.233 | 298.900 | 0.774 | 0.038 |
| Gstz1 | 4.877 | 7.695 | 0.634 | 0.199 |
| Gstz1 | 227.164 | 225.802 | 1.006 | 0.971 |
| Hmox1 | 82.765 | 45.999 | 1.799 | 0.061 |
| Hnf1a | 45.720 | 47.335 | 0.966 | 0.674 |
| Hnf1a | 196.592 | 194.543 | 1.011 | 0.999 |
| Idh1 | 130.231 | 89.558 | 1.454 | 0.018 |
| Il6 | 13.301 | 8.859 | 1.501 | 0.056 |
| Jak2 | 15.037 | 14.574 | 1.032 | 0.931 |
| Jak2 | 34.213 | 32.647 | 1.048 | 0.783 |
| Krit1 | 67.123 | 67.263 | 0.998 | 0.912 |
| Krit1 | 27.503 | 26.111 | 1.053 | 0.673 |

FIG. 6H

| | | | | |
|---|---|---|---|---|
| Krit1 | 23.553 | 19.068 | 1.235 | 0.087 |
| Lias | 96.917 | 114.659 | 0.845 | 0.001 |
| Lrrk2 | 15.303 | 18.555 | 0.825 | 0.202 |
| Lrrk2 | 58.413 | 66.367 | 0.880 | 0.143 |
| Magt1 | 11.061 | 11.982 | 0.923 | 0.600 |
| Magt1 | 58.745 | 63.173 | 0.930 | 0.644 |
| Map2k1 | 198.496 | 217.736 | 0.912 | 0.150 |
| Mgst1 | 115.114 | 148.369 | 0.776 | 0.036 |
| Mgst2 | 16.027 | 16.593 | 0.966 | 0.723 |
| Mlll2 | 9.565 | 6.771 | 1.413 | 0.320 |
| Mmp2 | 394.826 | 444.357 | 0.889 | 0.022 |
| Mmp9 | 9.086 | 9.856 | 0.922 | 0.803 |
| Mpv17 | 40.332 | 42.563 | 0.948 | 0.450 |
| Mt1 | 1413.202 | 548.677 | 2.576 | 0.088 |
| Mt2 | 56.833 | 18.428 | 3.084 | 0.053 |
| Mutyh | 15.853 | 13.989 | 1.133 | 0.493 |
| Naprt1 | 24.121 | 19.971 | 1.208 | 0.620 |
| Ndufa12 | 11.390 | 14.227 | 0.801 | 0.106 |
| Ndufs8 | 443.072 | 540.183 | 0.820 | 0.200 |
| Neil1 | 44.830 | 49.482 | 0.906 | 0.114 |
| Neil1 | 42.916 | 46.387 | 0.925 | 0.168 |
| Nfkb1 | 94.107 | 86.299 | 1.090 | 0.422 |
| Nfkb1 | 370.671 | 317.425 | 1.168 | 0.039 |
| Nme5 | 20.130 | 23.381 | 0.861 | 0.253 |
| Nox1 | 22.808 | 22.428 | 1.017 | 0.918 |
| Nqo1 | 54.237 | 60.431 | 0.898 | 0.221 |
| Nqo1 | 34.395 | 37.609 | 0.915 | 0.372 |
| Nudt15 | 24.065 | 27.850 | 0.864 | 0.238 |
| Ogg1 | 15.356 | 21.178 | 0.725 | 0.011 |
| Oplah | 23.549 | 23.217 | 1.014 | 0.977 |
| Oxsr1 | 196.386 | 215.676 | 0.911 | 0.150 |
| P4hb | 465.675 | 415.426 | 1.121 | 0.370 |
| Park7 | 1168.050 | 1357.724 | 0.860 | 0.093 |
| Pdia4 | 51.200 | 44.000 | 1.164 | 0.647 |
| Pdia5 | 25.660 | 18.633 | 1.388 | 0.025 |
| Pdilt | 13.910 | 10.927 | 1.273 | 0.107 |
| Plk3 | 86.233 | 86.517 | 0.997 | 0.921 |
| Ppargc1b | 52.554 | 68.485 | 0.767 | 0.152 |
| Ppargc1b | 12.278 | 11.244 | 1.092 | 0.561 |
| Ppp1r15b | 65.407 | 71.675 | 0.913 | 0.206 |
| Prdx1 | 823.939 | 892.239 | 0.923 | 0.372 |
| Prdx1 | 34.188 | 22.717 | 1.505 | 0.262 |
| Prdx2 | 639.175 | 679.461 | 0.941 | 0.639 |
| Prdx3 | 894.146 | 899.719 | 0.994 | 0.881 |
| Prdx6 | 635.457 | 649.507 | 0.978 | 0.737 |
| Prkca | 32.322 | 39.546 | 0.817 | 0.103 |
| Prkca | 95.650 | 106.925 | 0.895 | 0.446 |
| Prkca | 34.003 | 30.443 | 1.117 | 0.682 |

FIG. 6I

| | | | | |
|---|---|---|---|---|
| Prkca | 33.077 | 27.528 | 1.202 | 0.270 |
| Prkca | 19.052 | 15.657 | 1.217 | 0.595 |
| Prkca | 14.557 | 11.759 | 1.238 | 0.720 |
| Prkcd | 41.298 | 59.021 | 0.700 | 0.086 |
| Prkcd | 118.743 | 116.918 | 1.016 | 0.768 |
| Pmp | 193.471 | 191.150 | 1.012 | 0.957 |
| Psen1 | 67.235 | 60.235 | 1.116 | 0.387 |
| Psip1 | 45.528 | 50.117 | 0.908 | 0.350 |
| Psmb5 | 401.934 | 446.162 | 0.901 | 0.253 |
| Ptges2 | 160.581 | 189.263 | 0.848 | 0.015 |
| Ptgs1 | 98.729 | 93.294 | 1.058 | 0.589 |
| Ptgs2 | 9.049 | 7.620 | 1.187 | 0.425 |
| Ptprk | 46.634 | 48.407 | 0.963 | 0.625 |
| Ptprk | 7.847 | 7.378 | 1.063 | 0.743 |
| Ptprk | 23.006 | 21.138 | 1.088 | 0.307 |
| Ptprn | 27.875 | 30.334 | 0.919 | 0.470 |
| Pxdn | 50.712 | 46.939 | 1.080 | 0.349 |
| Qsox1 | 21.077 | 24.994 | 0.843 | 0.092 |
| Qsox1 | 18.695 | 12.356 | 1.513 | 0.108 |
| Qsox2 | 37.262 | 32.765 | 1.137 | 0.262 |
| Rgs14 | 159.316 | 161.162 | 0.989 | 0.899 |
| Romo1 | 634.533 | 735.736 | 0.862 | 0.165 |
| Rrm2b | 166.239 | 186.783 | 0.890 | 0.169 |
| Ryr2 | 15.286 | 22.458 | 0.681 | 0.004 |
| Ryr2 | 27.417 | 21.049 | 1.303 | 0.170 |
| Sh3bgrl3 | 143.952 | 99.097 | 1.453 | 0.253 |
| Sirt1 | 77.043 | 63.466 | 1.214 | 0.028 |
| Slc22a8 | 4.872 | 2.854 | 1.707 | 0.993 |
| Slc9a3r1 | 12.578 | 8.081 | 1.557 | 0.622 |
| Sod1 | 816.564 | 891.766 | 0.916 | 0.234 |
| Sod1 | 10.609 | 8.122 | 1.306 | 0.256 |
| Sod2 | 501.092 | 553.249 | 0.906 | 0.386 |
| Srxn1 | 41.730 | 37.819 | 1.103 | 0.651 |
| Tat | 17.840 | 15.759 | 1.132 | 0.359 |
| Tlr4 | 15.816 | 10.939 | 1.446 | 0.119 |
| Tmx1 | 68.594 | 65.538 | 1.047 | 0.618 |
| Tmx2 | 280.900 | 266.296 | 1.055 | 0.646 |
| Tmx3 | 91.682 | 85.208 | 1.076 | 0.328 |
| Tusc3 | 26.293 | 27.222 | 0.966 | 0.712 |
| Tusc3 | 29.402 | 26.656 | 1.103 | 0.746 |
| Txn1 | 346.511 | 321.706 | 1.077 | 0.770 |
| Txn2 | 392.713 | 410.440 | 0.957 | 0.624 |
| Txndc11 | 19.463 | 20.913 | 0.931 | 0.646 |
| Txndc11 | 40.310 | 42.695 | 0.944 | 0.546 |
| Txndc11 | 4036.619 | 3602.082 | 1.121 | 0.056 |
| Txndc12 | 41.706 | 49.872 | 0.836 | 0.219 |
| Txndc15 | 164.613 | 169.650 | 0.970 | 0.651 |
| Txndc5 | 13.572 | 15.921 | 0.852 | 0.341 |

FIG. 6J

| | | | | |
|---|---|---|---|---|
| Txndc5 | 107.423 | 99.415 | 1.081 | 0.379 |
| Txndc5 | 100.408 | 87.105 | 1.153 | 0.390 |
| Txndc9 | 178.258 | 190.268 | 0.937 | 0.388 |
| Txndc9 | 23.138 | 23.976 | 0.965 | 0.775 |
| Txndc9 | 16.151 | 14.761 | 1.094 | 0.499 |
| Txnip | 2489.362 | 2274.487 | 1.094 | 0.742 |
| Txnip | 1314.973 | 1138.449 | 1.155 | 0.563 |
| Txnl1 | 431.049 | 439.385 | 0.981 | 0.808 |
| Txnrd1 | 136.757 | 119.546 | 1.144 | 0.238 |
| Txnrd1 | 17.743 | 8.707 | 2.038 | 0.069 |
| Txnrd2 | 18.795 | 22.964 | 0.818 | 0.253 |
| Txnrd2 | 40.869 | 44.945 | 0.909 | 0.233 |
| Txnrd3 | 55.381 | 57.032 | 0.971 | 0.714 |
| Ucn | 20.809 | 17.873 | 1.164 | 0.472 |
| Ucp2 | 116.009 | 53.869 | 2.154 | 0.008 |
| Wrn | 15.730 | 9.352 | 1.682 | 0.065 |
| Xpa | 50.588 | 45.859 | 1.103 | 0.244 |

FIG. 6K

Table 3
Changes in autophagy related genes expression in Gne⁻/⁻hGNED176V-Tg mice analyzed by microarray

| Gene Symbol | Average Intensity Gne⁻/⁻hGNED176V-Tg (G) | Average Intensity Gne⁺/⁻hGNED176V-Tg (L) | Ratio (G/L) | p-value |
|---|---|---|---|---|
| Abl1 | 15.18 | 18.41 | 0.824 | 0.236 |
| Abl1 | 125.33 | 107.48 | 1.166 | 0.244 |
| Abl1 | 25.19 | 19.48 | 1.293 | 0.072 |
| Ambra1 | 1062.97 | 1334.29 | 0.812 | 0.281 |
| Ambra1 | 25.85 | 26.97 | 0.958 | 0.659 |
| Ambra1 | 19.06 | 18.22 | 1.046 | 0.864 |
| Arsa | 43.03 | 34.45 | 1.249 | 0.006 |
| Atg10 | 30.84 | 37.13 | 0.831 | 0.136 |
| Atg10 | 6.37 | 4.28 | 1.487 | 0.395 |
| Atg12 | 122.66 | 133.23 | 0.921 | 0.429 |
| Atg13 | 18.27 | 23.67 | 0.772 | 0.038 |
| Atg14 | 31.29 | 28.29 | 1.106 | 0.459 |
| Atg16l1 | 61.91 | 64.24 | 0.964 | 0.599 |
| Atg3 | 148.75 | 153.90 | 0.967 | 0.622 |
| Atg4a | 306.13 | 364.41 | 0.840 | 0.045 |
| Atg4a | 30.92 | 34.33 | 0.901 | 0.490 |
| Atg4b | 82.02 | 84.79 | 0.967 | 0.598 |
| Atg4c | 14.31 | 19.00 | 0.753 | 0.031 |
| Atg4d | 64.72 | 82.09 | 0.788 | 0.124 |
| Atg5 | 50.94 | 55.85 | 0.912 | 0.249 |
| Atg7 | 33.11 | 30.22 | 1.096 | 0.178 |
| Atg9b | 41.78 | 42.79 | 0.976 | 0.760 |
| Becn1 | 65.90 | 69.06 | 0.954 | 0.496 |
| Bnip1 | 83.61 | 94.85 | 0.882 | 0.104 |
| Bnip1 | 20.69 | 20.26 | 1.021 | 0.890 |
| Cdkn2d | 89.72 | 90.49 | 0.991 | 0.843 |
| Cisd2 | 32.38 | 31.64 | 1.024 | 0.803 |
| Cisd2 | 212.15 | 203.00 | 1.045 | 0.612 |
| Dap | 85.16 | 60.87 | 1.399 | 0.584 |
| Dap | 83.98 | 51.04 | 1.645 | 0.264 |
| Dram1 | 14.81 | 11.08 | 1.337 | 0.153 |
| Dram1 | 10.39 | 6.67 | 1.557 | 0.280 |
| Ei24 | 123.48 | 135.94 | 0.908 | 0.361 |
| Irgm1 | 91.23 | 81.76 | 1.116 | 0.260 |
| Lamp1 | 25.00 | 25.91 | 0.965 | 0.663 |
| Lamp1 | 833.63 | 686.64 | 1.218 | 0.035 |
| Map1lc3a | 864.27 | 903.99 | 0.956 | 0.563 |
| Map1lc3b | 773.33 | 621.95 | 1.243 | 0.062 |
| Park2 | 8.56 | 6.22 | 1.377 | 0.205 |

FIG. 6L

| | | | | |
|---|---|---|---|---|
| Park7 | 1168.05 | 1357.72 | 0.860 | 0.093 |
| Pik3cb | 14.26 | 10.50 | 1.358 | 0.159 |
| Prkaa1 | 43.08 | 43.18 | 0.998 | 0.974 |
| Prkaa1 | 19.49 | 19.00 | 1.026 | 0.887 |
| Prkaa2 | 774.02 | 734.97 | 1.053 | 0.736 |
| Psen1 | 67.24 | 60.24 | 1.116 | 0.387 |
| Rab24 | 89.78 | 103.95 | 0.864 | 0.070 |
| Rb1cc1 | 144.66 | 137.50 | 1.052 | 0.439 |
| Stk11 | 352.73 | 353.95 | 0.997 | 0.909 |
| Tm9sf1 | 75.78 | 71.32 | 1.063 | 0.656 |
| Tm9sf1 | 24.19 | 20.12 | 1.202 | 0.074 |
| Ulk1 | 47.23 | 45.62 | 1.035 | 0.973 |
| Ulk2 | 101.74 | 94.85 | 1.073 | 0.564 |
| Ulk3 | 14.50 | 12.88 | 1.126 | 0.449 |
| Wdr45 | 68.16 | 71.49 | 0.953 | 0.366 |
| Wipi1 | 184.52 | 178.49 | 1.034 | 0.581 |
| Wipi2 | 59.84 | 60.18 | 0.994 | 0.901 |

FIG. 6M

Table 4
Changes in collagen organization and biosynthesis related genes expression in Gne⁻/⁻ hGNED176V-Tg mice analyzed by microarray

| Gene Symbol | Average Intensity | | Ratio (G/L) | p-value |
|---|---|---|---|---|
| | Gne⁻/⁻hGNED176V-Tg (G) | Gne⁺/⁻hGNED176V-Tg (L) | | |
| Acan | 18.939 | 20.660 | 0.917 | 0.678 |
| Adamts14 | 192.803 | 197.796 | 0.975 | 0.675 |
| Adamts2 | 101.085 | 120.571 | 0.838 | 0.174 |
| Adamts2 | 24.508 | 20.827 | 1.177 | 0.581 |
| Adamts2 | 12.380 | 12.851 | 0.963 | 0.651 |
| Adamts2 | 33.768 | 26.668 | 1.266 | 0.349 |
| Anxa2 | 185.408 | 88.601 | 2.093 | 0.163 |
| Atp7a | 26.611 | 28.451 | 0.935 | 0.553 |
| Col10a1 | 6.526 | 8.426 | 0.775 | 0.224 |
| Col11a1 | 22.121 | 21.909 | 1.010 | 0.925 |
| Col11a2 | 13.948 | 10.822 | 1.289 | 0.148 |
| Col12a1 | 25.397 | 20.774 | 1.223 | 0.267 |
| Col13a1 | 7.915 | 6.139 | 1.289 | 0.101 |
| Col14a1 | 56.211 | 40.337 | 1.394 | 0.144 |
| Col17a1 | 114.982 | 88.151 | 1.304 | 0.002 |
| Col18a1 | 13.581 | 10.950 | 1.240 | 0.447 |
| Col19a1 | 11.140 | 10.905 | 1.022 | 0.543 |
| Col19a1 | 20.245 | 15.002 | 1.349 | 0.114 |
| Col1a1 | 56.516 | 42.103 | 1.342 | 0.634 |
| Col1a2 | 12.737 | 10.049 | 1.267 | 0.071 |
| Col1a2 | 206.884 | 129.426 | 1.598 | 0.515 |
| Col20a1 | 29.076 | 24.147 | 1.204 | 0.174 |
| Col22a1 | 8.379 | 8.205 | 1.021 | 0.907 |
| Col22a1 | 52.997 | 45.294 | 1.170 | 0.504 |
| Col23a1 | 30.521 | 27.569 | 1.107 | 0.203 |
| Col23a1 | 29.947 | 25.400 | 1.179 | 0.239 |
| Col24a1 | 25.457 | 25.409 | 1.002 | 0.866 |
| Col27a1 | 35.915 | 26.356 | 1.363 | 0.099 |
| Col2a1 | 38.484 | 42.493 | 0.906 | 0.506 |
| Col3a1 | 1159.976 | 803.206 | 1.444 | 0.805 |
| Col3a1 | 18.834 | 19.279 | 0.977 | 0.809 |
| Col4a1 | 119.272 | 95.303 | 1.252 | 0.270 |
| Col4a2 | 9.994 | 12.379 | 0.807 | 0.311 |
| Col4a2 | 17.272 | 21.290 | 0.811 | 0.355 |
| Col4a2 | 52.864 | 42.141 | 1.255 | 0.199 |
| Col4a3bp | 220.470 | 273.131 | 0.807 | 0.005 |
| Col4a4 | 24.690 | 22.466 | 1.099 | 0.452 |
| Col4a5 | 17.165 | 10.790 | 1.591 | 0.035 |

FIG. 6N

| | | | | |
|---|---|---|---|---|
| Col5a1 | 50.276 | 35.835 | 1.403 | 0.363 |
| Col5a1 | 18.591 | 16.185 | 1.149 | 0.510 |
| Col5a2 | 125.285 | 82.033 | 1.527 | 0.644 |
| Col5a3 | 109.416 | 129.895 | 0.842 | 0.417 |
| Col6a1 | 85.293 | 73.004 | 1.168 | 0.826 |
| Col6a2 | 659.898 | 486.081 | 1.358 | 0.813 |
| Col6a3 | 17.454 | 17.994 | 0.970 | 0.666 |
| Col6a3 | 129.864 | 101.682 | 1.277 | 0.685 |
| Col6a4 | 60.460 | 69.084 | 0.875 | 0.249 |
| Col6a4 | 56.297 | 42.840 | 1.314 | 0.138 |
| Col6a5 | 7.371 | 8.820 | 0.836 | 0.426 |
| Col6a6 | 7.598 | 8.231 | 0.923 | 0.566 |
| Col6a6 | 17.119 | 17.880 | 0.957 | 0.745 |
| Col7a1 | 22.680 | 29.112 | 0.779 | 0.195 |
| Col7a1 | 24.630 | 22.788 | 1.081 | 0.674 |
| Col8a1 | 10.021 | 6.094 | 1.644 | 0.306 |
| Col9a1 | 11.944 | 10.419 | 1.146 | 0.895 |
| Col9a3 | 14.015 | 17.274 | 0.811 | 0.389 |
| Dpt | 240.963 | 179.179 | 1.345 | 0.265 |
| Foxc1 | 26.833 | 21.231 | 1.264 | 0.072 |
| Foxc2 | 8.925 | 7.468 | 1.195 | 0.811 |
| Foxs1 | 9.484 | 10.204 | 0.929 | 0.808 |
| Lmx1b | 49.028 | 38.824 | 1.263 | 0.175 |
| Lmx1b | 9.112 | 7.121 | 1.280 | 0.412 |
| Lox | 52.499 | 28.187 | 1.863 | 0.032 |
| Nf1 | 54.387 | 56.583 | 0.961 | 0.490 |
| Nf1 | 15.914 | 16.813 | 0.947 | 0.556 |
| Nf1 | 84.956 | 94.691 | 0.897 | 0.163 |
| P4ha1 | 140.941 | 129.630 | 1.087 | 0.283 |
| Plod3 | 87.722 | 70.295 | 1.248 | 0.095 |
| Scx | 21.061 | 30.255 | 0.696 | 0.018 |
| Serpinf2 | 21.250 | 19.175 | 1.108 | 0.443 |
| Serpinh1 | 249.346 | 201.092 | 1.240 | 0.779 |
| Serpinh1 | 165.847 | 128.883 | 1.287 | 0.755 |
| Sfrp2 | 11.413 | 13.992 | 0.816 | 0.633 |
| Tgfb1 | 27.152 | 18.576 | 1.462 | 0.336 |
| Tgfb2 | 45.763 | 42.207 | 1.084 | 0.242 |
| Tgfb2 | 9.721 | 12.269 | 0.792 | 0.473 |
| Tgfbr1 | 11.870 | 11.784 | 1.007 | 0.858 |
| Tnxb | 46.815 | 37.689 | 1.242 | 0.183 |
| Tram2 | 19.855 | 19.952 | 0.995 | 0.985 |
| Tram2 | 19.248 | 17.179 | 1.120 | 0.800 |
| Tram2 | 45.072 | 36.440 | 1.237 | 0.071 |

FIG. 6O

FIG. 7A
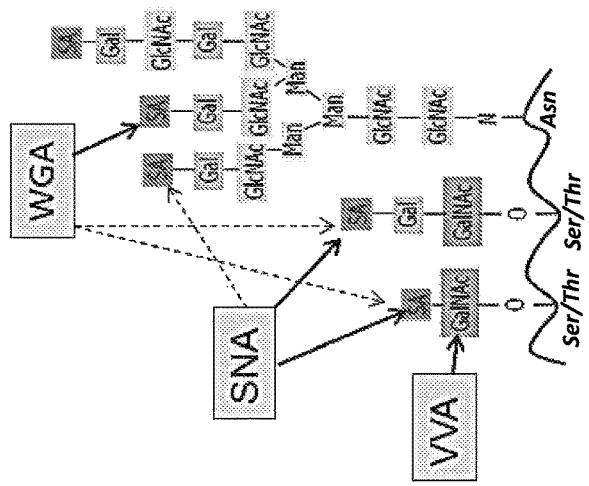
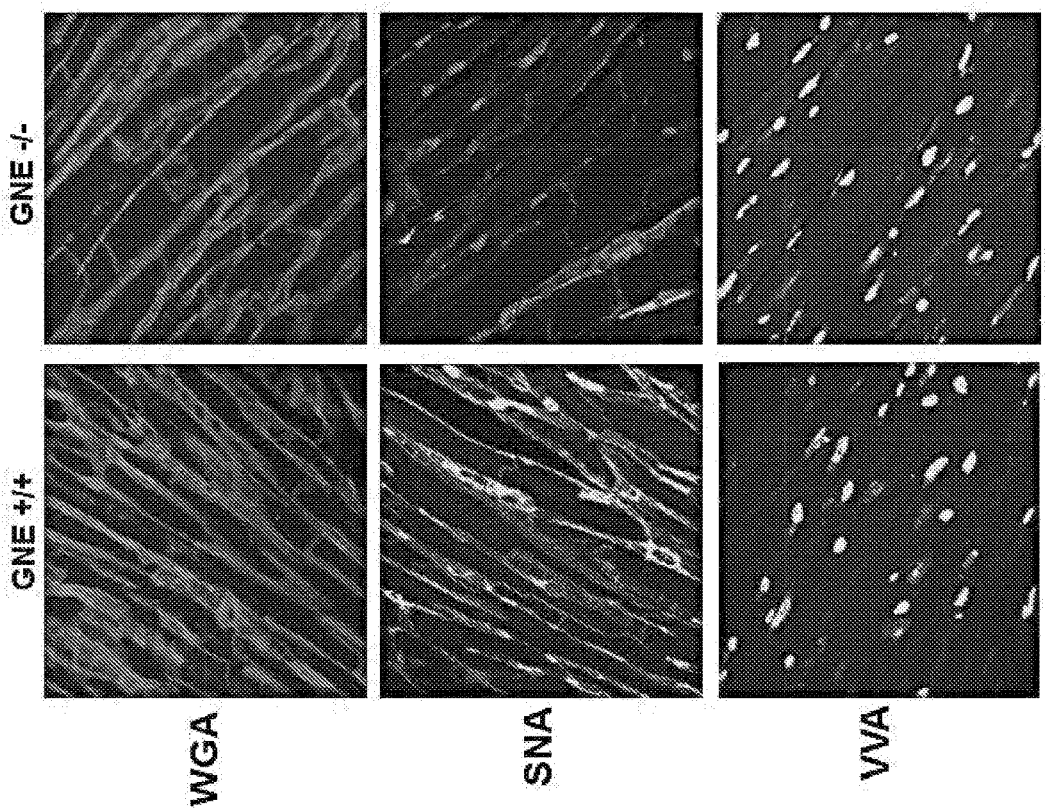

Ejection Fraction

Fractional Shortening

LV Mass

LV Mass Corrected

Diastolic LV Volume

Systolic LV Volume

FIG. 10

| | RR Interval (ms) | Heart Rate (BPM) | PR Interval (ms) | P Duration (ms) | QRS Interval (ms) | QT Interval (ms) | QTc (ms) | JT Interval (ms) |
|---|---|---|---|---|---|---|---|---|
| Mutant (n=5) | 131.6 (±11.03) | 457.65 (±38.25) | 40.475 (±2.11) | 14.285 (±2.96) | 9.739 (±0.25) | 16.91 (±1.05) | 46.61 (±7.17) | 7.1695 (±1.58) |
| Control (n=5) | 122.15 (±5.02) | 491.6 (±20.36) | 34.27 (±1.89) | 24.325 (±3.8) | 8.537 (±0.29) | 16.635 (±3.1) | 47.515 (±8.1) | 8.101 (±2.89) |

SIALYLATION-INCREASING THERAPIES FOR DISEASES ASSOCIATED WITH OXIDATIVE STRESS

CROSS REFERENCE TO RELATED APPLICATIONS

This is the U.S. National Stage of International Application No. PCT/US2016/019084, filed Feb. 23, 2016, which was published in English under PCT Article 21 (2), which claims the benefit of U.S. Provisional Application No. 62/120,742, filed Feb. 25, 2015, which is incorporated herein by reference.

ACKNOWLEDGEMENT OF GOVERNMENT SUPPORT

This invention was made with Government support under project number ZIA HG000215 16 by the National Institutes of Health, National Human Genome Research Institute. The Government has certain rights in the invention.

FIELD OF THE DISCLOSURE

This application relates to the use of sialylation increasing therapies, such as N-acetyl-mannosamine and derivatives thereof, for the treatment of disorders associated with oxidative stress, such as cardiovascular disorders associated with oxidative stress, for example heart failure, myocardial infarction, and atherosclerotic vascular disease.

BACKGROUND

Upon reaction with electrons, oxygen is transformed into reactive oxygen species (ROS). All ROS types, including superoxide anions and hydrogen peroxide, have unpaired valence electrons or unstable bonds. ROS is known to destroy bacteria and destroy human cells. In addition, exposure to high ROS concentrations can lead to damage to proteins, lipids, and nucleic acids. Low to intermediate ROS concentrations are believed to exert their effects rather through regulation of cell signaling cascades.

A variety of diseases are believed to be caused by a surplus of ROS, including cardiovascular diseases such as myocardial infarction and atherosclerosis. A need remains for therapeutic agents to treat subject with disorders associated with increased production of reactive oxygen species.

SUMMARY OF THE DISCLOSURE

It is disclosed herein that reactive oxygen species (ROS) generation is increased in GNE myopathy. In addition, it was determined that cardiac muscles are involved in GNE myopathy. Hyposialylation of cardiac muscles leads to impaired cardiac muscle contractility, and can be improved with sialylation-increasing therapies. The results show that sialylation increasing therapies can be of use in disorders associated with reactive oxygen species, specifically cardiovascular disorders.

Methods are disclosed for detecting a disorder associated with oxidative stress. In some embodiments, methods are disclosed for treating a subject with a cardiovascular disorder associated with oxidative stress, comprising administering to the subject a therapeutically effective amount of a sialic acid precursor, sialic acid, or one or more sialylated compounds, mannosamine, N-acetyl mannosamine or a derivative thereof.

In additional embodiments, methods are disclosed for treating a subject with GNE myopathy that has impaired cardiac function. The method include selecting a subject with GNE myopathy that has impaired cardiac function; and administering to the subject a therapeutically effective amount of a sialic acid precursor, sialic acid, or one or more sialylated compounds, mannosamine, N-acetyl mannosamine or a derivative thereof. The method can include the use of these agents for the treatment of heart failure, myocardial infarction, cardiovascular disorders, and atherosclerotic vascular disease.

In additional embodiments, the method includes selecting a subject with GNE myopathy who has not been identified as having impaired cardiac function and testing the subject's cardiac function. The method can also include administering to the subject at therapeutically effective amount of an anti-oxidant accompanied or unaccompanied by a therapeutically effective amount N-acetyl mannosamine or a derivative thereof, mannosamine, a sialic acid precursor, sialic acid, or one or more sialylated compounds. The method can improve cardiac function in the subject. The method can be used to treat previously unidentified of heart failure, myocardial infarction, cardiovascular disorders, and/or atherosclerotic vascular disease, or to prevent these conditions.

The foregoing and other features and advantages of the invention will become more apparent from the following detailed description of several embodiments which proceeds with reference to the accompanying figures.

BRIEF DESCRIPTION OF THE FIGURES

FIGS. 2A-2D. ROS production in GNE Myopathy muscle was measured in vivo using microdialysis. (A-B) Experimental setup and representative HPLC chromatograms. Perfusion medium containing 5 mM salicylate (SA) was pumped through a microdialysis probe and dihydroxybenzoic acid (DHBA) in dialysate was detected by HPLC-ECD system. A, baseline; B, post-stimulus. Electrical stimulus (ES) consisted of 50V, 40 Hz, 3 ms pulses for 300 trains. (C-D) 2, 5-DHBA increments after contraction was significantly greater in GNE Myopathy mice (n=9) than those in littermates (n=5). Pre-ES, before ES; ES1, $1^{st}$ 20 min after ES; ES2, $2^{nd}$ 20 min after ES. (C) Data represent mean±SEM. (D) Each circle represents a 2,5-DHBA level from an individual mouse.

FIGS. 3A-3F. Antioxidant capacity is impaired in hyposialylated GNE Myopathy myotubes. (A) Intracellular ROS generation was imaged by fluorescence microscopy with green DCF staining. (B) DCF fluorescence was quantified by using a multi-well fluorescence plate reader. Data represent mean±SEM of each group (n=14). (C-F) ROS levels and cells viability were analyzed with the addition of increasing concentration of $H_2O_2$(0.5, 1.0, 2.0, and 4.0 mM) or menadione (5, 10, 20, and 40 µM) to culture media. Control myotubes of each group were cultured in the same condition without adding $H_2O_2$ or menadione. Each point is mean±SEM of four determinations. (C-D) Increased ROS levels with the addition of pro-oxidants were determined by subtracting mean fluorescence of control cells. (E-F) Viable cells were counted using propidium iodide/Hoechst co-staining. Relative viability (%) was calculated in comparison to control cells of each group.

FIGS. 4A-4F. Oral N-acetyl cysteine (NAC) administration improved muscle force generation and motor performance in GNE Myopathy mice. Gne(-/) hGNED176V-Tg mice (circles) were treated with low dose (LD; light gray fill color; n=13) and high dose (HD; dark grayfill color; n=13) NAC and compared to untreated group (NT; white fill color; n=17). Littermate controls (reverse triangles) were treated in the same conditions (LD; n=7, HD; n=7, and NT; n=6). (A) Treadmil performance test evaluating the distance that the mice could run. (B) Treadmil endurance test evaluating the number of beam breaks during a constant loading. (C-F) Contractile forces of gastrocnemius muscles. (C) Peak isometric twitch force (Pt). (D) Maximum tetanic force (Po). (E) Specific isometric force (Pt normalized by CSA). (F) Specific tetanic force (Po normalized by CSA). Values from each mouse are shown with mean±SEM (*P<0.05, **P<0.01).

FIG. 6A-60. Tables 1-4. Collagen organization and biosynthesis related genes. Detailed genes lists.

FIGS. 7A-7B. (A) Paraffin-embedded heart sections from GNE myopathy mutant mice [Gne(-/-)hGNED176V-Tg mice (GNE (-/-) and unaffected littermates (GNE+/+)] were stained with three lectins informative for sialylation status and co-stained with the nuclear dye DAPI (blue). Left ventricular cardiac muscle tissue was imaged and showed selective hyposialylation in GNE myopathy compared with control muscle, demonstrated by apparent normal staining of WGA (binding to most sialic acid groups), but decreased staining of SNA (predominantly binding terminal α(2,6)-linked sialic acid on all glycans). In addition, staining of VVA (predominantly binding terminal GalNAc, without sialic acid attached, O-linked to serine or threonine residues of glycoproteins) was not significantly increased in GNE myopathy heart specimen. (B) Paraffin-embedded muscle sections (gastrocnemius) from GNE myopathy mutant mice (-/-) and unaffected control mice (control) were stained with the lectins SNA and VVA (green) and co-stained with the nuclear dye DAPI (blue) [adapted from Niethamer et al., 2012]. GNE myopathy muscle specimens show hyposialylation, as demonstrated by decreased staining of SNA compared with control skeletal muscle. In addition, staining of VVA showed an increased signal, indicating significant hyposialylation of O-linked glycoproteins. Oral supplementation of ManNAc (1 g/kg/day for 12 weeks) restored the sialylation status back to the normal range, demonstrated by increased SNA, and decreased/absent VVA signal intensities similar to control specimens.

FIG. 10. Electrocardiography (ECG) findings in GNE myopathy mice. Both 3 and 6 lead ECG were performed on GNE myopathy mutant [Gne(-/-)hGNED176V-Tg mice] and control littermate mice. ECG findings show that GNE myopathy mutant mice had an increased PR interval of 40.475 (±2.11) ms; the normal range of PR intervals is 31.7-36.5 ms. GNE myopathy mutant mice had QRS intervals within the normal range.

As shown in FIG. 7A, GNE -/- mice showed decreased staining of SNA (predominantly binding terminal α(2,6)-linked sialic acid on all glycans) of heart tissue compared to control littermates (GNE+/+). Heart tissues collected from ~1 year old GNE -/- mice treated since age 10 weeks with either 2 g/kg/day ManNAc or 2 g/kg/day Neu5Ac (sialic acid) (Malicdan et al. Nat Med 2009; 15: 690-695) showed significantly increased sialylation of glycans compared to untreated GNE -/- mice, indicating resialylation of glycans in heart tissue after these sialylation-increasing therapies.

DETAILED DESCRIPTION OF SEVERAL EMBODIMENTS

Figure 1A:
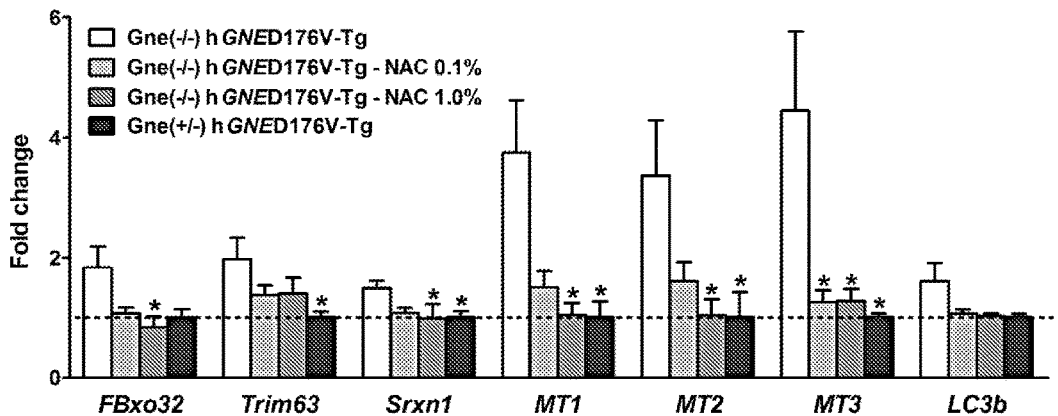
FIGS. 1A-1E. Atrogenes and oxidative stress related genes are upregulated in GNE Myopathy (GM) muscles. (A) Expression of atrogin-1/FBxo32, MuRF1/Trim63, Srxn1, MTs, and LC3b in untreated (white bars, n=17), N-acetyl-cysteine (NAC) treated (gray bars, n=6 per group), and littermate controls (black bars, n=6). $Gne^{-/-}hGNED176V$-Tg muscles were measured by quantitative RT-PCR and expressed as fold changes of littermates controls. Data represent mean±SEM of each group. (B-E) Microarray analysis followed by gene ontology profiling. Each dot represents average expression values for the same gene from $Gne^{-/-}hGNED176V$-Tg (vertical axis, n=9) and littermates (horizontal axis, n=3) muscles. Inverted triangles show recovered expression values with NAC treatment (vertical axis, n=6) for significantly upregulated genes. (B) Muscle atrophy related genes. (C) Oxidative stress and redox homeostasis related genes. (D) Autophagy related genes. (E) Collagen organization and biosynthesis related genes. Detailed genes are listed Tables 1-4 (FIG. 6).
Figure 1B:
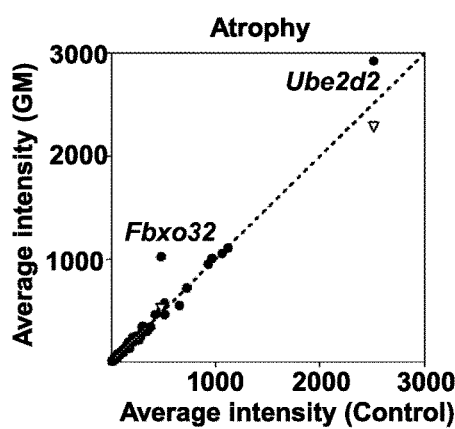
Figure 1C:
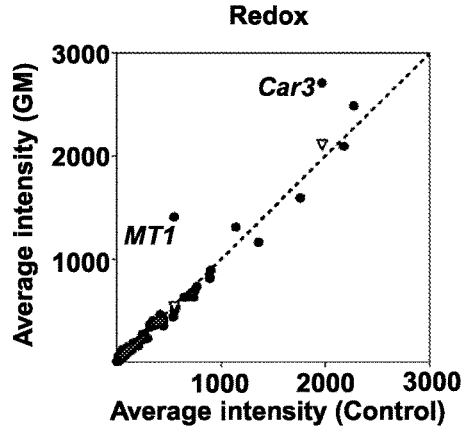
Figure 1D:
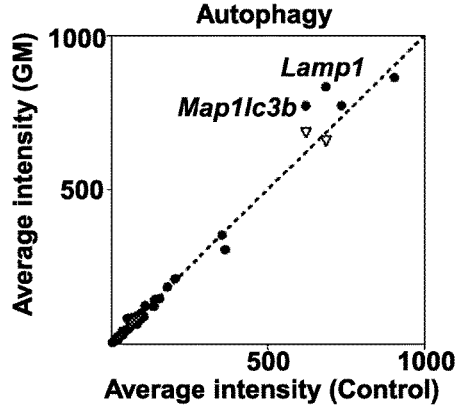
Figure 1E:
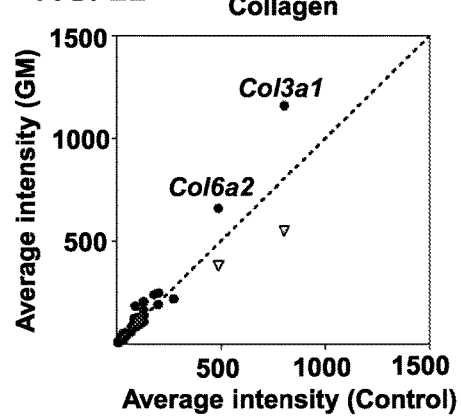

It is disclosed herein that disorders associated with oxidative stress, such as cardiovascular disorders associated with oxidative stress can be treated using an agent that increases sialylation. It was determined that generation of reactive oxygen species is increased in both in vitro and in vivo models of a hyposialylation disorder. Methods for treating disorders associated with oxidative stress, and methods for diagnosing these disorders are disclosed.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided:

Administration: Providing a compound to a subject by another person or self-administration by the subject.

Animal: Living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as big cats, zebras, etc. The term subject applies regardless of the stage in the organism's life-cycle.

Alteration: A statistically significant change in a parameter as compared to a control. In one example, an "increase" is a statistically significant elevation in a parameter, such as the presence of a biological marker, or the ratio of two biological markers, such as the T/ST ratio. The alternation can be measured as compared to a control. Suitable statistical analyses are well known in the art, and include, but are not limited to, Student's T test and ANOVA assays. In one example, a "decrease" or "reduction" is a statistically significant decline in a parameter, such as the presence of a biological marker, such as the T/ST ratio as compared to a control. In another example, an "increase" is a statistically significant higher level of a parameter, such as the presence of a biological marker, such as the T/ST ratio as compared to a control. Suitable statistical analyses are well known in the art, and include, but are not limited to, Student's T test and ANOVA assays.

Atherosclerosis: The progressive narrowing and hardening of a blood vessel over time. Atherosclerosis is a common form of arteriosclerosis in which deposits of yellowish plaques (atheromas) containing cholesterol, lipoid material and lipophages are formed within the intima and inner media of large and medium-sized arteries. Treatment of atherosclerosis includes reversing or slowing the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques). "Assessing atherosclerosis" indicates determining if a subject of interest has atherosclerosis, determining the prognosis of the subject of interest, and/or determining if a therapeutic regimen administered to the subject is effective in treating the subject.

Arrhythmia: A heart condition wherein the electrical activity of the heart is irregular, or faster or slower than normal. Tachycardia is general more than 100 beats per minute for a human adult, bradycardia is generally below 60 beats were minute for a human adult. The arrhythmia can be an atrial, ventricular, or at the atrioventricular junction. Atrial arrhythmias include sinus bradycardia, premature atrical contractions, wander atrial pacemaker, atrial tachycardia, multifocal atrial tachycardia, atrial flutter, and atrial fibrillation. Junction arrhythmias include AVnodal reentrant tachycardia, junctional rhythm, junctional tachycardia and premature junctional contraction. Ventricular arrhythmias include premature ventricular contractions, accelerated idio-ventricular rhythm, monomorphic ventricular tachycardia, polymorphic ventricular tachycardia, and ventricular fibrillation.

Beta blocker: A type of drug that targets the beta receptor, which are found on the cells of heart muscles. Beta blockers interfere with binding of epinephrine and other stress hormones to the beta receptor. These drugs are often used for the management of cardiac arrhythmias, prevention of heart attacks and heart failure, and for treating hypertension.

Bile acid binding resins: Agents that lower LDL cholesterol. Bile acids are the breakdown products of cholesterol and are excreted by the liver via the bile. Bile acids are 90% reabsorbed from the intestine and used to re-manufacture cholesterol in the liver. Bile acid binding resins (also referred to as bind acid sequestrants) interfere with this intestinal reabsorption by binding bile acids in the gut and promoting their excretion from the body.

Cardiomyopathy: Measurable deterioration of the ability of the myocardium to contract, usually leading to heart failure. Cardiomyopathy includes hypertrophic cardiomyopathy, arrhythmogenic right ventricular cardiomyopathy, isolated ventricular non-compaction, mitochondrial myopathy, dilated cardiomyopathy, restrictive cardiomyopathy, peripartum cardiomyopathy, Takotsubo cardiomyopathy, and Loeffler endocarditis.

Cardiovascular: Pertaining to the heart and/or blood vessels.

Cardiovascular disease (CVD): Disorders of the heart and blood vessels, such as atherosclerosis (ASCVD), coronary heart disease, cerebrovascular disease, and peripheral vascular disease. Cardiovascular diseases also include, for example, myocardial infarction, stroke, angina pectoris, transient ischemic attacks, and congestive heart failure. Atherosclerosis usually results from the accumulation of fatty material, inflammatory cells, extracellular matrices and plaque. Clinical symptoms and signs indicating the presence of CVD may include one or more of the following: chest pain and other forms of angina, shortness of breath, sweatiness, Q waves or inverted T waves on an EKG, a high calcium score by CT scan, at least one stenotic lesion on coronary angiography, and heart attack. Subclinical ASCVD can be identified by imaging tests (such as CT measures of coronary calcification, or MRI measures of coronary or aortic plaque, and/or ultrasound evidence of carotid plaque or thickening).

Cholesterol absorption inhibitor: A class of cholesterol lowering drugs that block absorption of cholesterol at the brush border of the intestine without affecting absorption of tri-glycerides or fat soluble vitamins. These drugs are not systemically absorbed and can lower cholesterol on their own (i.e. without the use of additional drugs). An exemplary cholesterol absorption inhibitor is ezetimibe (Ezetrol).

Cholesterol lowering agent: An agent that lowers the level of cholesterol in a subject, such as a pharmaceutical, vitamin, or small molecule. One of skill in the art can readily identify assays, such as blood screening, to determine the effect of cholesterol. Agents include, but are not limited to, niacin, the statins (e.g., ZOCOR™, LIPITOR™, PRAVACOL™, LESCOR™, MEVACOR™), bile acid binding resins (e.g., QUESTRAN™), and fibrates (e.g. LOPID™, LIPIDIL MICRO™).

Control: A "control" refers to a sample or standard used for comparison with an experimental sample. In some embodiments, the control is a sample obtained from a healthy patient or a non-diseased tissue sample obtained from a patient diagnosed with the disorder of interest, such as a cardiovascular disorder associated with oxidative stress, for example HF or ASCVD. In some embodiments, the control is a historical control or standard reference value or range of values (such as a previously tested control sample, such as a group of patients with the disorder, or group of samples that represent baseline or normal values, such as the level of specific genes in non-diseased tissue).

Determining or Measuring: Identifying the presence of a target molecule in a sample. There terms refer to measuring a quantity or quantitating a target molecule in the sample, either absolutely or relatively. For example, T and ST can be analyzed in a sample from a subject of interest, such as a subject suspected of having a hyposialylation disorder. The sample can be any biological sample of interest, such as, but not limited to, a plasma sample, serum sample, or tissue extract. Generally, detecting, measuring or determining a biological molecule requires performing an assay, such as mass spectrometry, and not simple observation.

Diagnosing or diagnosis of a disorder associated with oxidative stress: Detecting the disorder by measuring specific parameters. For example, a disorder can be detected by determining the T/ST ratio in a biological sample. Diagnosis can encompass laboratory confirmation of a pre-existing clinical condition or a specific disease.

Diuretic: A drug that promotes the production of urine. Diuretics are often used to treat heart failure, hypertension and other diseases.

Fibrates: Agents that lower tri-glyceride levels and raise HDL levels. Fibrates, also known as fibric acid derivatives, are particularly useful in diabetic patients whose characteristic lipid abnormality is high tri-glycerides and low HDL. In some patients who have combined lipid abnormalities, fibrates are combined with statins to lower both tri-glycerides and LDL and to raise HDL. Exemplary fibrates include gemfibrozil (LOPID™), fenofibrate (Lipidil micro, Lipidil Supra, Lipidil EZ), and bezafibrate (Bezalip).

Framingham Risk Score: A risk factor score that is used for predicting future risk of coronary artery disease in individuals free of disease, based on the measurement of Framingham risk factors which include age, gender, systolic blood pressure (and use of antihypertensive treatment), cigarette smoking, diabetes, as well as total cholesterol (or low density lipoprotein cholesterol (LDL cholesterol) and high density lipoprotein cholesterol (HDL cholesterol) levels (Wilson et al., *Circulation* 1998; 97: 1837-47).

Glycoprotein: Proteins that contain oligosaccharide chains (glycans) covalently attached to polypeptide sidechains. The carbohydrate is attached to the protein in a cotranslational or posttranslational modification process known as glycosylation. There are two main types of glycosylation, N-glycosylation, O-glycosylation. In N-glycosylation, the addition of the sugar occurs on an amide nitrogen, such as in the side chain of asparagine. In O-glycosylation, the addition of the sugar occurs on a hydroxyl oxygen, such as on the side chain of hydroxylysine, hydroxyproline, serine or threonine. The sugars commonly found in eukaryotic glycoproteins include, but are not limited to, β-D-glucose, β-D-galactose, β-D-mannose, α-L-fucose, N-Acetylgalactosamine, N-Acetylglucosamine, N-Acetylneuraminic acid, and xylose.

Heart failure (HF): The physiological state in which cardiac output is insufficient in meeting the needs of the body and lungs. This condition is also called "congestive heart failure," and is most commonly caused when cardiac output is low and the lungs become congested with fluid due to an inability of heart output to properly match venous return. Heart failure can also occur in situations of high output, where the ventricular systolic function is normal but the heart can't process the augmentation of blood volume. This can occur in overload situation (blood or serum infusions), renal diseases, chronic severe anemia, beriberi (vitamin B i/thiamine deficiency), thyrotoxicosis, Paget's disease, arteriovenous fistulae, or arteriovenous malformations. Heart failure includes left sided failure and right sided failure, wherein the left and right ventricles are affected, respectively, and biventricular failure. Ischemic heart disease (including myocardial infarction), cigarette smoking, hypertension, obesity, diabetes, and valvular heart disease are associated with increased risk of heart failure. Viral myocarditis, human immunodeficiency virus infections, connective tissue disease (such as systemic lupus erythematous), drug (cocaine) abuse, and some chemotherapeutic agents can cause heart failure.

Hyposialylation: Reduced or absent addition of sialic acid (N-acetyl neuraminic acid (Neu5Ac) and its derivatives) to galactose (Gal) or other underlying monosaccharides (such as, but not limited to N-acetylgalactose (GalNAc)), Mannose (Man), N-acetylglucosamine (GlcNAc), N-acetlylneuraminic acid (Neu5Ac) or of sialic acid chains in polysialylation (PSA), such as on PSA-NCAM.

Hyposialylation disorders are conditions with hyposialylation of glycoproteins and glycolipids in affected tissues. Hyposialylation of affected tissues can be detected, for example, using histochemistry staining of fixed tissue slides with specific lectins. A demonstration of a significant reduction (or absence) of sialic acid, either by a statistically reduced staining/binding of sialic acid recognizing lectins (such as, but not limited to wheat germ agglutinin (WGA), *Sambucus nigra* agglutinin (SNA), and Limax flavus agglutinin (LFA) or by presence of staining of free monosaccharides underlying sialic acid on the glycan chain, including galactose or GalNAc, by the lectins (such as, but not limited to, *helix pomatia* agglutinin (HPA), *Vicia villosa* agglutinin (VVA), jackfruit agglutinin (Jacalin), and peanut agglutinin (PNA) can be used to identify hyposialylation disorders, such as certain cases with myopathy (including the adult-onset, progressive, autosomal recessive muscular disorder, GNE myopathy, also called distal myopathy with rimmed vacuoles (DMRV)/hereditary inclusion body myopathy (HIBM)), renal disorders (including, but not limited to minimal change nephrosis, lupus nephritis, IgA nephropathy, diabetic nephropathy), sleep disorders (including those with reduced REM sleep), neurodegenerative disorders (including those with amyloid depositions), cancers and liver disorders. Western blotting or 2D gel electrophoresis followed by lectin labeling or immunolabeling with a specific antibody to a sialoglycan can also be used to detect hyposialylation disorders. Methods for detecting are disclosed, for example, in Kakani et al. Am J Pathol 2012: 180: 1431-1440 and Niethamer et al. Mol Genet Metab 2012: 107:748-755.

Inhibiting or treating a disease: Inhibiting the full development of a disease or condition, or decreasing intensity for example, in a subject who has a cardiovascular disorder associated with oxidative stress. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, reports of reduced intensity of pain, or by other parameters well known in the art that are specific to the particular disease. A "prophylactic" treatment is a treatment administered to a subject who does not exhibit signs of a disease or exhibits only early signs for the purpose of decreasing the risk of developing pathology.

Ion Exchange Chromatography: A chromatographic process that allows the separation of ions and polar molecules based on their charge. Ion-exchange chromatography retains analyte molecules on the column based on coulombic (ionic) interactions. The stationary phase surface displays ionic functional groups (R-X) that interact with analyte ions of opposite charge. This type of chromatography is further subdivided into cation exchange chromatography and anion exchange chromatography. The ionic compound consisting of the cationic species M+ and the anionic species B− can be retained by the stationary phase.

Generally, a sample is introduced, either manually or with an autosampler, into a sample loop of known volume. A buffered aqueous solution (often called the "mobile phase") carries the sample from the loop onto a column that contains a stationary phase material that is typically a resin or gel matrix consisting of agarose or cellulose beads with covalently bonded charged functional groups. The target analytes (either anions or cations) are retained on the stationary phase, but can be eluted by increasing the concentration of a similarly charged species that will displace the analyte ions from the stationary phase. For example, in cation exchange chromatography, the positively charged analyte can be displaced by the addition of positively charged sodium ions. The analytes of interest are detected, such as by conductivity or an ultraviolet (UV)/Visible light absorbance. Generally, a chromatography data system (CDS) is used to control the chromotography system.

Intravenous Immunoglobulin (IVIG): A blood product that includes pooled polyvalent IgG extract from the plasma of a number of blood donors. It is used as treatment for immune deficiencies such as X-linked agammaglobulinemia, autoimmune diseases, such as immune thrombocytopenia and Kawaski disease, and acute infections.

Level of Expression: An amount, such as of a protein or an mRNA, that can be measured in a biological sample.

Lipoprotein: A biochemical assembly that contains both proteins and lipids, bound to the proteins, which allow fats to move through the water inside and outside cells. There are five major groups of lipoprotein particles, which, in order of molecular size, largest to smallest, are chylomicrons, very low-density lipoprotein (VLDL), intermediate-density lipoprotein (IDL), low-density lipoprotein (LDL), and HDL. HDL contains the highest proportion of protein to cholesterol; its most abundant apolipoproteins are apo A-I and apo A-II. LDL contains apolipoprotein B, and has a core consisting of linoleate and includes esterified and non-esterified cholesterol molecules. LDL particles are approximately 22 nm in diameter and have a mass of about 3 million daltons. Lipoprotein a, (Lp(a)) is a lipoprotein subclass; lipoprotein a consists of an LDL-like particle and the specific apolipoprotein(a) [apo(a)], which is covalently bound to the apolipoprotein B of the LDL like particle.

Mammal: This term includes both human and non-human mammals. Examples of mammals include, but are not limited to: humans, pigs, cows, goats, cats, dogs, rabbits, rats, and mice.

Mass Spectrometry: A process used to separate and identify molecules based on their mass. Mass spectrometry ionizes chemical compounds to generate charged molecules or molecule fragments and measures their mass-to-charge ratios. In a typical MS procedure, as sample is ionized. The ions are separated according to their mass-to-charge ratio, and the ions are dynamically detected by some mechanism capable of detecting energetic charged particles. The signal is processed into the spectra of the masses of the particles of that sample. The elements or molecules are identified by correlating known masses by the identified masses.

"Time-of-flight mass spectrometry" (TOFMS) is a method of mass spectrometry in which an ion's mass-to-charge ratio is determined via a time measurement. Ions are accelerated by an electric field of known strength. This acceleration results in an ion having the same kinetic energy as any other ion that has the same charge. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion. "Liquid chromatography-mass spectrometry" or "LC-MS" is a chemistry technique that combines the physical separation capabilities of liquid chromatography (or HPLC) with the mass analysis capabilities of mass spectrometry. Liquid chromatography mass spectrometry (LC-MS) separates compounds chromatographically before they are introduced to the ion source and mass spectrometer. It differs from gas chromatography (GC-MS) in that the mobile phase is liquid, usually a mixture of water and organic solvents, instead of gas and the ions fragments. Most commonly, an electrospray ionization source is used in LC-MS.

Mean and Standard Deviation: The arithmetic mean is the "standard" average, often simply called the "mean".

$$\bar{x} = \frac{1}{n} \cdot \sum_{i=1}^{n} x_i$$

The mean is the arithmetic average of a set of values.

The standard deviation (represented by the symbol sigma, σ) shows how much variation or "dispersion" exists from the mean. The standard deviation of a random variable, statistical population, data set, or probability distribution is the square root of its variance. The standard deviation is commonly used to measure confidence in statistical conclusions. Generally, twice the standard deviation is about the radius of a 95 percent confidence interval. Effects that fall far outside the range of standard deviation are generally considered statistically significant. One of skill in the art can readily calculate the mean and the standard deviation from a population of values.

Myocardial Infarction (MI): An event that occurs when blood stops flowing properly to part of the heart and the heart muscle is injured due to inadequate oxygen delivery. Acute myocardial infarction refers to two subtypes of acute coronary syndrome, namely non-ST-elevated myocardial infarction and ST-elevated myocardial infarction, which are most frequently (but not always) a manifestation of coronary artery disease. The most common triggering event is the disruption of an atherosclerotic plaque in an epicardial coronary artery, which leads to a clotting cascade, sometimes resulting in total occlusion of the artery. If impaired blood flow to the heart lasts long enough, it triggers a process called the ischemic cascade; the heart cells in the territory of the occluded coronary artery die, chiefly through necrosis. A collagen scar forms in the heart in place of the damaged cells.

Niacin: A B-vitamin that is used as a medication for patients with elevated levels of tri-glycerides and cholesterol. A long-acting preparation of niacin is available as NIASPAN®.

Prognosis: A prediction of the future course of a disease, such as ASCVD or HF. The prediction can include determining the likelihood of a subject to develop complications of ASCVD or HF, or to survive a particular amount of time (e.g., determine the likelihood that a subject will survive 1, 2, 3 or 5 years), to respond to a particular therapy (e.g., lipid lowering therapy), or combinations thereof.

Reactive Oxygen Species and Oxidative Stress: Reactive oxygen species are oxygen radicals and hydrogen peroxide ($H_2O_2$), singlet oxygen, lipid peroxides, $O_2$—, pro-oxidants and refers to molecules or ions formed by the incomplete one-electron reduction of oxygen. These reactive oxygen intermediates include singlet oxygen, superoxides; peroxides; hydroxyl radical; and hypochlorous acid. They contribute to the microbicidal activity of phagocytes, regulation of signal transduction and gene expression, and the oxidative damage to nucleic acids; proteins; and lipids.

Oxidative stress is an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA. Chemically, oxidative stress is associated with increased production of oxidizing species or a significant decrease in the effectiveness of antioxidant defenses, such as glutathione.

Renal hyposialylation disorder: A disease of the kidneys characterized by decreased sialylation. In some subjects, the glomeruli are hyposialylated. These disorders include some forms of podocytopathies, minimal change nephrosis, focal and segmental glomerulosclerosis, membranous glomerulonephritis, and other forms of unexplained idiopathic nephrotic syndrome, as well as glomerular basement membrane diseases such as Alport disease and thin membrane disease. Such kidney disorders and conditions are sometimes characterized by segmental splitting of the glomerular basement membrane and/or podocytopathy due to disturbed polyanions on podocyte membranes, or to changes in the amount or charge (sialylation) of glomerular basement membrane components.

Sample (or biological sample): A biological specimen containing genomic DNA, RNA (including mRNA), protein, or combinations thereof, obtained from a subject. Examples include, but are not limited to, peripheral blood, serum, plasma, urine, fine needle aspirate, tissue biopsy, surgical specimen, and autopsy material.

Sialic acid: A negative charged sugar that is a terminal sugar on glycans. The most common sialic acid is 5-N-acetylneuraminic acid, a monosaccharide with a nine-carbon backbone. Other less common sialic acids are N- or O-substituted derivatives of 5-N-neuraminic acid. Sialic acids are found widely distributed in animal tissues and to a lesser extent in other species, ranging from plants and fungi to yeasts and bacteria, mostly in glycoproteins and gangliosides. The amino group generally bears either an acetyl or glycolyl group. The hydroxyl substituents include acetyl, lactyl, methyl, sulfate, and phosphate groups. Sialic acid is transferred to an oligosaccharide by a sialyltransferase.

In renal functions, sialic acid residues are important for maintenance of glomerular integrity, facilitating glomerular filtration, and their deficiency is implicated in proteinuria and/or hematuria. It has also been reported that glomerular podocyte and podocyte foot process morphologies are maintained by the anionic charge of sialic acid residues on podocyte glycoproteins and glycolipids, and that a barrier to protein permeability is controlled by functional endothelial glycocalyx, rich in sialic acid.

Statin: Any of a class of lipid-lowering drugs that reduce serum cholesterol levels by inhibiting a key enzyme involved in the biosynthesis of cholesterol. Example statins include atorvastatin (LIPITOR®), fluvastatin (LESCOL®), lovastatin (MEVACOR®, ALTOCOR®, not marketed in the UK), pravastatin (PRAVACHOL®, SELEKTINE®, LIPOSTAT®), rosuvastatin (CRESTOR®), simvastatin (ZOCOR®). There are two groups of statins: (1) Fermentation-derived: lovastatin, simvastatin and pravastatin, and (2) Synthetic statins: fluvastatin, atorvastatin, cerivastatin and rosuvastatin. Generally, statins act by competitively inhibiting 3-hydroxy-3-methylglutaryl coenzyme A (HMG CoA) reductase, an enzyme of the HMG-CoA reductase pathway, the body's metabolic pathway for the synthesis of cholesterol.

The structure of one exemplary statin, lovastatin, is shown below.

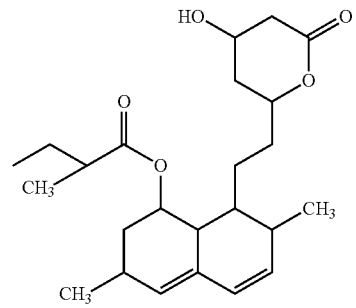 [SMILES: CCC(C)C(=O)OC1CC(C)C=C2C=CC(C)C(CCC3CC(O)CC(=O)O3)C21]

Standard: A substance or solution of a substance of known amount, purity or concentration that is useful as a control. A standard can also be a known value or concentration of a particular substance. A standard can be compared (such as by spectrometric, chromatographic, spectrophotometric, or statistical analysis) to an unknown sample (of the same or similar substance) to determine the presence of the substance in the sample and/or determine the amount, purity or concentration of the unknown sample. In one embodiment, a standard is a particular T/ST ratio. In another embodiment, a standard is a known ratio of T/ST that is found in a sample from a subject that does not have a cardiac disorder associated with oxidative stress.

Subject: Living organisms susceptible to hyposialylation disorders; a category that includes both human and non-human mammals, such as non-human primates.

Therapeutically effective amount: An amount of a pharmaceutical preparation that alone, or together with a pharmaceutically acceptable carrier or one or more additional therapeutic agents, induces the desired response. A therapeutic agent, such as MaNAc or any other sialylation increasing therapy, is administered in therapeutically effective amounts.

Effective amounts a therapeutic agent can be determined in many different ways, such as assaying for a reduction in atherosclerotic disease or improvement of physiological condition of a subject having vascular disease. Effective amounts also can be determined through various in vitro, in vivo or in situ assays.

Therapeutic agents can be administered in a single dose, or in several doses, for example daily, during a course of treatment. However, the effective amount of can be dependent on the source applied, the subject being treated, the severity and type of the condition being treated, and the manner of administration.

In one example, it is an amount sufficient to partially or completely alleviate symptoms of vascular disease within a subject. Treatment can involve only slowing the progression of the vascular disease temporarily, but can also include halting or reversing the progression of the vascular disease permanently. For example, a pharmaceutical preparation can decrease one or more symptoms of vascular disease, for example decrease a symptom by at least 20%, at least 50%, at least 70%, at least 90%, at least 98%, or even at least 100%, as compared to an amount in the absence of the pharmaceutical preparation.

Thomsen-Friedenreich Antigen: N-actetyl galactosamine linked Galactose (Galβ1-3GalNAcα1), also known as "T" antigen. The monosialylated form of this antigen (Neu5Ac-Gal-GalNAc) is called "ST" antigen; a disialylated form also exists. The structures of T and ST are shown in FIG. 3 of PCT Publication No. 2014/160018, incorporated herein by reference. Methods for detecting T and ST are disclosed, for example, in Leoyklang et al. Biomarkers Med 2014: 8: 641-652.

Treating a disease: "Treatment" refers to a therapeutic intervention that ameliorates a sign or symptom of a disease or pathological condition, such a sign, parameter or symptom of cardiovascular disease (for example, ASCVD). Treatment can also induce remission or cure of a condition, such as a cardiovascular disease. In particular examples, treatment includes preventing a disease, for example by inhibiting the full development of a disease, such as preventing development of cardiovascular disease. Prevention of a disease does not require a total absence of the disease. For example, a decrease of at least 50% can be sufficient.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods of Treatment

The methods disclosed herein relates to compositions and methods for preventing and/or reducing cellular and tissue damage caused by oxidative stress. The compositions and methods disclosed herein are useful in preventing and treating a variety of disease states or pathological situations in which reactive oxygen species (ROS) are produced and released. The methods include administering to the subject a therapeutically effective amount of a sialylation increasing therapy, such as a sialic acid precursor, sialic acid, one or more sialylated compounds, mannosamine, or N-acetyl mannosamine or a derivative thereof.

Methods are disclosed herein for treating a subject with a cardiovascular disorder associated with oxidative stress. In some embodiments, the cardiovascular disorder is associated with hyposialylation, such as hyposialylation in the cardiac and/or vascular tissue. In some embodiments, the subject has heart failure or atherosclerotic cardiovascular disease. In additional embodiments, the subject has myocardial infarction, ischemic heart disease, stroke, cardiomyopathy, arrhythmia, restrictive cardiomyopahyor peripheral arterial disease.

Subjects with restrictive cardiomyopathy or an arrhythmia identified by heart function testing will be good candidates for treatment. Such subjects have decreased cardiac output, and increased end-diastolic volume and end-systolic volumes. Exemplary decreased cardiac output, and increased end-diastolic volume and end-systolic volumes are shown in the GNE myopathy mouse model with oxidative-stress related cardiomyopathy (see the Examples section).

In some embodiments, to select a subject with cardiac impairment for sialylation-increasing therapy, levels of plasma oxidative stress markers and/or plasma T/ST ratios can be evaluated. When oxidative stress markers are increased compared to an unaffected individual and/or plasma T/ST ratios are increased beyond the normal range, the individual can be administered the sialylation increasing therapy, such as a sialic acid precursor, sialic acid, one or more sialylated compounds, mannosamine, or N-acetyl mannosamine or a derivative thereof.

In some embodiments, the subject has a hyposialylation disorder, such as, but not limited to GNE myopathy. The subject can have a cardiovascular disorder associated with oxidative stress, and GNE myopathy. In specific examples, the subject has cardiac impairment and GNE myopathy. A subject can be selected that has signs or symptoms of restrictive cardiomyopathy, an arrhythmia, decreased cardiac output, increased end-diastolic volume, decreased end-systolic volume, or a combination thereof. The method can include selecting this subject for treatment.

In further embodiments, the subject does not have GNE myopathy. Thus, in some examples, the subject has a cardiovascular disorder associated with oxidative stress, but does not have GNE myopathy. The method can include selecting this subject for treatment.

In yet other embodiments, the subject has GNE myopathy. Thus, in some examples, the subject has a cardiovascular disorder associated with oxidative stress, and has GNE myopathy. The method can include selecting this subject for treatment.

In yet other embodiments, the subject has been determined to be at risk for cardiovascular disease based on risk factors, such as, but not limited to, Framingham risk factors, or guidelines jointly issued by the American Heart Association and American College of Cardiology. In specific non-limiting examples, the method can include evaluating a subject to determine if the subject is at risk for cardiovascular disease using Framingham risk factors. These risk factors include age, gender, whether the subject smokes, blood pressure, total cholesterol level, and high density lipoprotein cholesterol level (see above).

The Framingham Risk Score is a gender-specific algorithm used to estimate the 10-year cardiovascular risk of a subject using specific factors. The Framingham Risk Score was first developed based on data obtained from the Framingham Heart Study, to estimate the 10-year risk of developing coronary heart disease (see Third Report of the National Cholesterol Education Program (NCEP) Expert Panel on Detection, Evaluation, and Treatment of High Blood Cholesterol in Adults (Adult Treatment Panel III) final report, *Circulation* 2002 Dec. 17; 106(25):3143-421, incorporated herein by reference). The method can include evaluation of a subject to determine if the subject is at risk for cardiovascular disease using risk factors, such as, but not limited to, Framingham risk factors and/or guidelines jointly issues by the American Heart Association and American College of Cardiology.

Framingham risk factors include age, gender, low density lipoprotein (LDL) cholesterol level, whether the subject smokes, blood pressure (and whether the subject is receiving pharmacological treatment for hypertension), total cholesterol level, and high density lipoprotein (HDL) cholesterol level. Programs for this evaluation are available on the internet, such as at the U.S. National Heart, Lung, and Blood Institute (NHLBI) website. The disclosed methods can include (a) selecting a subject for treatment based on the Framingham risk factor and/or (b) evaluating the Framingham risk factors as part of the treatment protocol.

In some embodiments, the subject has heart failure (HF). HF is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and enlarged hearts. The most common cause of HF is atherosclerosis, which causes blockages in the coronary arteries that provide blood flow to the heart muscle. Ultimately, such blockages may cause myocardial infarction with subsequent decline in heart function and resultant heart failure. Other causes of HF include valvular heart disease, hypertension, viral infections of the heart, alcohol consumption, and diabetes. Some cases of HF occur without clear etiology and are called idiopathic.

There are several types of HF. Two types of HF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure. The disclosed methods are of use in treating subject with systolic or diastolic heart failure.

HF is also classified according to its severity. The New York Heart Association classification classifies CHF into four classes:

Class I—no obvious symptoms, with no limitations on physical activity;
Class II—some symptoms during or after normal activity, with mild physical activity limitations;
Class III—symptoms with less than ordinary activity, with moderate to significant physical activity limitations;
Class IV—significant symptoms at rest, with severe to total physical activity limitations.

The disclosed methods can be used to treat a subject that has class I, class II, class III or class IV heart failure.

The disclosed methods are also of use to treat a subject that has acute HF. Acute HF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema, and dyspnea.

The subject with HF can be administered an additional therapeutic agent, such as, but not limited to vasodilators, positive inotropes, and/or diuretics. In some embodiments, the subject is administered a beta-antagonists. The subject can be administered dopamine, dobutamine, dopexamine, or isoproterenol. The subject can be administered a therapeutically effective amount of an angiotensin-converting enzyme (ACE) inhibitor, a beta blocker, an aldosterone antagonist, a diuretic, an angiotensin receptor blocker (ARB), and/or a vasodilator.

In some embodiments, the disclosed methods are of use to treat a subject with atherosclerosis. The subject can have atherosclerotic heart disease. In some embodiments the subject can also be administered a therapeutically effective amount of a statin, niacin, a fibrate, a bile acid binding resin, a cholesterol absorption inhibitor, a PCSK9-targeting drug, an LDL-targeting drug or an HDL-targeting drug.

In some embodiments, the disclosed methods are of use to treat a subject who has a myocardial infarction, or previously had a myocardial infarction. Generally, these subjects have cardiac tissue death caused by ischemia. Acute myocardial infarction (AMI), or a "heart attack," occurs when localized myocardial ischemia causes the development of a defined region of tissue death. AMI is most often caused by rupture of an atherosclerotic lesion in a coronary artery. This causes the formation of a thrombus that plugs the artery, stopping it from supplying blood to the region of the heart that it supplies.

The disclosed methods are of use to treat a subject that has cardiac ischemia. Severe and prolonged ischemia produces a region of necrosis spanning the entire thickness of the myocardial wall. Such a transmural infarct usually causes ST segment elevation. Less severe and protracted ischemia can arise when coronary occlusion is followed by spontaneous reperfusion; an infarct-related artery is not completely occluded; occlusion is complete, but an existing collateral blood supply prevents complete ischemia; or the oxygen demand in the affected zone of myocardium is smaller. Under these conditions, the necrotic zone may be mainly limited to the subendocardium, typically causing non-ST segment elevation MI. A subject with any of these changes can be selected for treatment.

The subject can have a myocardial infarction or cardiac ischemia, and can also be administered a therapeutically effective amount of an antiplatelet agent, an anticoagulation agent, or a lipid or blood pressure regulating agent. Exemplary lipid regulating agents are statin, niacin, PCSK9-targeting drug, bile acid binding resin, or HDL-cholesterol targeting drug.

In other embodiments the disclosed methods are of use to treat subject has a vascular disorder, thrombotic stroke, peripheral vascular disease, restenosis, acute coronary syndrome, or reperfusion myocardial injury. The subject can also have chronic kidney disease associated with a heart condition, such as diabetic neuropathy. The disclosed methods can also be used to treat a subject with diastolic dysfunction, restrictive cardiomyopathy, and/or and arrhythmia.

In any embodiment disclosed herein, the subject can be administered a therapeutically effective amount of an anti-oxidant, such as N-acetylcysteine, vitamin C, beta carotene, or vitamin E. In a specific non-limiting example, the subject can be administered a therapeutically effective amount of N-acetylcysteine.

In additional embodiments, the method includes selecting a subject with GNE myopathy who has not been identified as having impaired cardiac function and testing the subject's cardiac function. The method can also include administering to the subject at therapeutically effective amount of an anti-oxidant.

Sialylation Increasing Therapies

The methods disclosed herein include administering to the subject a therapeutically effective amount of a sialylation increasing therapy. Thus, a therapeutically effective amount of a sialic acid precursor, sialic acid, or one or more sialylated compounds, mannosamine, or N-acetyl mannosamine, a derivative thereof, or any combination of these sialylation increasing agents, can be administered to the subject.

Sialic acids are sugars found on many cellular and tissue components. For example, sialic acids are present on most cell surfaces, and on proteins and lipids and are involved in cell to cell interactions. Sialic acid-rich oligosaccharides on the glycoconjugates found on surface membranes help keep water at the surface of cells. The sialic acid-rich regions also contribute to creating a negative charge on the cells surface. Since water is a polar molecule, it is attracted to cell surfaces and membranes. Thus, sialic acids contribute to cellular hydration and fluid uptake. Sialic acid is also a vital component of many body fluids including, serum, cerebrospinal, saliva, amniotic, and mother's milk. Any therapeutic agent that increases sialylation can be used in the methods disclosed herein. In some embodiments, the subject is administered a sialic acid precursor, sialic acid, or one or more sialylated compounds.

The subject can be administered intravenous immunoglobulin (IVIG) or sialyllactose. Intravenous immunoglobulin is pooled, polyvalent immunoglobulin G (IgG) extracted from donors. In some embodiments, IVIG is administered at a high dosage, such as about 100 to 400 mg per kg of body weight, or about 1 to about 2 grams IVIG per kg body weight.

The therapeutic agent can be mannosamine or a derivative thereof. See also European Patent No. EP 1521761, which is incorporated herein by reference.

I. N-acetyl-mannosamine

N-acetyl-mannosamine and derivatives thereof are useful for treating a variety of diseases and cardiovascular disorders associated with oxidative stress, as disclosed herein, including. N-acetyl-D-mannosamine is a key compound in the sialic acid biosynthetic pathway. In particular, there is a regulated, rate-limiting enzymatic step in the pathway that leads to sialic acid formation, and this rate-limiting step gives rise to N-acetyl-D-mannosamine. Hence, once N-acetyl-D-mannosamine is formed or administered, no other enzymatic step leading to the formation of sialic acid is subject to feedback inhibition. Thus, administration of N-acetyl-D-mannosamine will lead to increased amounts of sialic acid. The structure of N-acetyl-mannosamine is shown below.

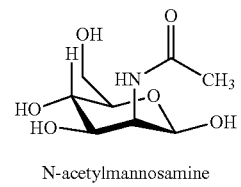

N-acetylmannosamine

Therefore, administration of N-acetyl mannosamine (ManNAc) and/or its derivatives promotes formation of sialic acid (N-acetylneuramic acid).

II. N-Acetylmannosamine Derivatives

N-acetylmannosamine and derivatives thereof can also be used in the therapeutic methods and compositions of the invention. The structures of such N-acetylmannosamine derivatives of use are shown by Formula I.

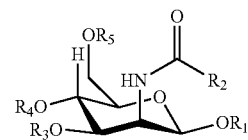

wherein:

$R_1$, $R_3$, $R_4$, or $R_5$ is hydrogen, lower alkanoyl, carboxylate or lower alkyl; and $R_2$ is lower alkyl, lower alkanoylalkyl, lower alkyl alkanoyloxy.

The following definitions are used, unless otherwise described: Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

Lower alkyl refers to $(C_1-C_6)$alkyl. Such a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$ cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

III. Formulations and Administration

N-acetyl mannosamine and/or derivatives thereof or any sialylation increasing therapeutic agent are administered so as to achieve a reduction in at least one symptom associated with an indication or disease. For example, administration of N-acetyl mannosamine and/or derivatives thereof or any sialylation increasing therapeutic agent can lead to an improvement in vascular function, an improvement in cardiac function, and/or increased oxygenation of the blood. In additional embodiments, administration of N-acetyl mannosamine and/or derivatives thereof or any sialylation increasing therapeutic agent results in re-sialylating hyposialylated heart tissue, reducing reactive oxygen species in the heart and/or blood vessels, and/or improving vascular function.

To achieve the desired effect(s), N-acetyl mannosamine and/or derivatives thereof, or any sialylation increasing therapeutic agent, can be administered as single or divided dosages, for example, of at least about 0.01 mg/kg to about 500 to 750 mg/kg, of at least about 0.01 mg/kg to about 300 to 500 mg/kg, at least about 0.1 mg/kg to about 200 to 400 mg/kg or at least about 1 mg/kg to about 25 to 200 mg/kg of body weight, although other dosages may provide beneficial results. The amount administered will vary depending on various factors including, but not limited to the disease, the weight, the physical condition, the health, the age of the mammal, whether prevention or treatment is to be achieved. Such factors can be readily determined by the clinician employing animal models or other test systems that are available in the art.

Administration of the therapeutic agents can be in a single dose, in unit dosage form, in multiple doses, in a continuous or intermittent manner, depending, for example, upon the recipient's physiological condition, whether the purpose of the administration is therapeutic or prophylactic, and other factors known to skilled practitioners. The administration of N-acetyl mannosamine and/or derivatives thereof, or any sialylation increasing therapeutic agent, may be essentially continuous over a pre-selected period of time or may be in a series of spaced doses. Both local and systemic administration is contemplated.

To prepare the composition, N-acetyl mannosamine and/or one or more derivatives thereof and/or or any sialylation increasing therapeutic agent are synthesized or otherwise obtained, and purified as necessary or desired. N-acetyl mannosamine (and/or derivatives thereof, or any sialylation increasing therapeutic agent) can then be added to a composition (or food product), adjusted to the appropriate concentration, and optionally combined with other agents. The absolute weight of N-acetyl mannosamine and/or its derivatives, or any sialylation increasing therapeutic agent, that is included in a unit dose can vary widely. For example, about 0.01 to about 2 g, or about 0.1 to about 1 g of N-acetyl mannosamine and/or derivatives thereof (or any sialylation increasing therapeutic agent) are often used in compositions. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of N-acetyl mannosamine and/or derivatives thereof (or any sialylation increasing therapeutic agent) can vary as well. Such daily doses can range, for example, from about 0.01 g/day to about 50 g/day, from about 0.02 g/day to about 25 g/day, from about 0.03 g/day to about 12 g/day, from about 0.04 g/day to about 10 g/day, from about 0.05 g/day to about 8 g/day, and from about 0.07 g/day to about 6 g/day.

In some non-limiting example, a dose of dose 2 g/kg/day N-acetyl mannosamine is administered. In another embodiment, a dose of 2 g/kg/day Neu5Ac (sialic acid) is administered.

Thus, one or more suitable unit dosage forms comprising N-acetyl mannosamine and/or derivatives thereof, or any sialylation increasing therapeutic agent, can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing N-acetyl mannosamine and/or derivatives thereof with liquid carriers, solid matrices, semisolid carriers, finely divided solid carriers or combinations thereof, and then, if necessary, introducing or shaping the product into the desired delivery system.

When N-acetyl mannosamine and/or its derivatives, or any sialylation increasing therapeutic agent, is prepared for oral administration, it is generally combined with a pharmaceutically acceptable carrier, diluent or excipient to form a pharmaceutical formulation, or unit dosage form. For oral administration, N-acetyl mannosamine (and/or derivatives thereof or any other sialylation increasing therapeutic agent) may be present as a powder, a granular formulation, a solution, a suspension, an emulsion or in a natural or synthetic polymer or resin for ingestion of N-acetyl mannosamine (and/or derivatives thereof or any other sialylation increasing therapeutic agent) from a chewing gum. The active ingredients may also be presented as a bolus, electuary or paste. Orally administered N-acetyl mannosamine and/or derivatives thereof, or any sialylation increasing therapeutic agent, can also be formulated for sustained release. For example, N-acetyl mannosamine and/or derivatives thereof or any sialylation increasing therapeutic agent, can be coated, can be micro-encapsulated, or otherwise placed within a sustained delivery device, for example, in order to avoid salivary bacteria degradation. The total N-acetyl mannosamine and its derivatives, or any other sialylation increasing therapeutic agent, in such formulations comprises from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing N-acetyl mannosamine and/or derivatives thereof, or any sialylation increasing therapeutic agent, can be prepared by procedures known in the art using well-known and readily available ingredients. For example, N-acetyl mannosamine and/or its derivatives, or any sialylation increasing therapeutic agent, can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as acetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing N-acetyl mannosamine (and/or its derivatives or any sialylation increasing therapeutic agent) can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing N-acetyl mannosamine (and/or its derivatives or any sialylation increasing therapeutic agent) can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing N-acetyl mannosamine and/or its derivatives, or any sialylation increasing therapeutic agent, are designed to resist disintegration in the stomach and dissolve in the more neutral to alkaline environment of the duodenum.

N-acetyl mannosamine and/or its derivatives, or any sialylation increasing therapeutic agent, can also be formulated as an elixir or solution for convenient oral administration or as a solution appropriate for parenteral administration, for instance by intramuscular, subcutaneous, intraperitoneal or intravenous routes. The pharmaceutical formulations of N-acetyl mannosamine and/or its derivatives, or any sialylation increasing therapeutic agent, can also take the form of an aqueous or anhydrous solution or dispersion, or alternatively the form of an emulsion or suspension or salve.

Thus, N-acetyl mannosamine and/or its derivatives, or any sialylation increasing therapeutic agent, may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The N-acetyl mannosamine, its derivatives, or any sialylation increasing therapeutic agent, and other ingredients may form suspensions, solutions, or emulsions in oily or aqueous vehicles, and may contain formulatory agents such as suspending, stabilizing and/or dispersing agents. Alternatively, the N-acetyl mannosamine, its derivatives, or any sialylation increasing therapeutic agent, and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add other ingredients such as antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added. In one embodiment, N-acetylcysteine is added to the composition.

Additionally, N-acetyl mannosamine and/or derivatives thereof, or any sialylation increasing therapeutic agent, are well suited to formulation in a sustained release dosage form. Thus, such formulations can be so constituted that they release the N-acetyl mannosamine and/or its derivative, for example, in a particular part of the intestinal, urogenital or respiratory tract, over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, N-acetyl mannosamine and/or its derivative(s), or any sialylation increasing therapeutic agent, may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, N-acetyl mannosamine and/or its derivatives, or any sialylation increasing therapeutic agent, can be delivered via patches or bandages for dermal administration. Alternatively, N-acetyl mannosamine and/or its derivatives, or any sialylation increasing therapeutic agent, can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The therapeutic agents can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with N-acetyl mannosamine and/or derivatives thereof, or any sialylation increasing therapeutic agent, in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

N-acetyl mannosamine and/or its derivatives, or any sialylation increasing therapeutic agent, may further be formulated for topical administration in the mouth or throat. For example, N-acetyl mannosamine and/or its derivatives, or any sialylation increasing therapeutic agent, may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations may include, as optional ingredients, pharmaceutically acceptable carriers, diluents, solubilizing or emulsifying agents, and salts of the type that are available in the art.

Furthermore, N-acetyl mannosamine and/or its derivatives, or any sialylation increasing therapeutic agent, may also be used in combination with other therapeutic agents, for example, pain relievers, anti-inflammatory agents, and the like, whether for the conditions described or some other condition.

The present invention further pertains to a packaged pharmaceutical composition such as a kit or other container for increasing production of sialic acid in a mammal. The kit or container holds a therapeutically effective amount of a pharmaceutical composition for increasing intracellular production of sialic acid and instructions for using the pharmaceutical composition for increasing production of sialic acid in the mammal. The pharmaceutical composition includes N-acetyl mannosamine and/or its derivatives in a therapeutically effective amount such that sialic acid production is increased.

IV. Food Supplement

N-acetyl mannosamine and/or its derivatives, or any sialylation increasing therapeutic agent, can be administered as a food supplement or incorporated into food or drink item such as a nutritional bar, snack bar, cookie, candy, cereal, pudding, ice cream, frozen confectionary, chewing gum, drink mix, soda pop, liquid supplement, sauce, salad dressing, gravy, jelly, jam, spread, margarine, peanut butter, nut spread, frosting, and the like. In essence, it can be used in any food, composition or supplement in which sugar is employed. Hence, N-acetyl mannosamine and/or derivatives thereof, or any sialylation increasing therapeutic agent, can be used as a partial or full substitute for sugar.

Such food supplements, drinks and food items can include any other food ingredient including, for example, flour, oil, cream, butter, sugar, salt, spices and the like. In addition, the food supplements, drinks and food items can include vitamins and nutrients commonly found in other nutritional supplements.

Methods for Diagnosis

Methods are disclosed herein for diagnosing a disorder associated with oxidative stress, including confirming a diagnosis of a disorder associated with oxidative stress, such as a clinical diagnosis. In some embodiments, disorder is a cardiovascular disorder associated with oxidative stress (see above). These methods include obtaining a biological sample from a subject of interest, such as a subject suspected of having a cardiovascular disorder associated with oxidative stress, and measuring monosialylated Thomsen-Friedenreich (ST) antigen and measuring non-sialylated Thomsen-Friedenreich antigen (T). The ratio of T to ST (T/ST), in the biological sample is determined.

In some embodiments, a method is provided for diagnosing a cardiovascular disorder associated with oxidative stress, for example confirming the diagnosis of a cardiovascular disorder associated with oxidative stress, that includes measuring an amount of monosialylated Thomsen-Friedenreich (ST) antigen in a biological sample from the subject and measuring an amount of non-sialylated Thomsen-Friedenreich antigen (T) in the biological sample from the subject. The ratio of T to ST is determined. The ratio of T to ST can be compared to a control, such as a standard value. In some embodiments, a subject is selected that is suspected of having the cardiovascular disorder, such as based on clinical symptoms.

In specific non-liming examples method can be used to diagnose heart failure or atherosclerotic cardiovascular disease. In other non-limiting examples, the method can be used to diagnose myocardial infarction, ischemic heart disease, stroke, or peripheral arterial disease. In further non-limiting examples the method can be used to diagnose decreased cardiac function associated with a hyposialylation disorder, such as GNE myopathy. Thus, the method can be used to detect cardiomyopathy and/or arrhythmia.

In some embodiments, a ratio of T to monosialylated ST (T/ST) in a plasma or serum sample of greater than about 0.051 to greater than about 0.062, greater than about 0.052 to greater than about 0.06, greater than about 0.058 to greater than about 0.062, such as about 0.052 or greater, about 0.053 or greater, about 0.054 or greater, about 0.055 or greater, about 0.056 or greater, about 0.057 or greater, about 0.058 or greater, about 0.059 or greater, or about 0.06 or greater indicates that the overall sialylation of O-linked glycoproteins in the plasma or serum is below 95% of the population and that the subject has the cardiovascular disorder, and/or confirms the diagnosis of the cardiovascular disorder. In some embodiments, a T/ST ratio in serum or plasma of greater than about 0.07, about 0.08, about 0.09, or about 0.1 indicates that the subject has a cardiovascular disorder. In other embodiments, a ratio of T to ST (T/ST) of less than about 0.06, less than about 0.059, less than about 0.058, less than about 0.057, less than about 0.056, less than about 0.054, less than about 0.053, less than about 0.052, or less than about 0.051, in plasma or serum indicates that the subject does not have the cardiovascular disorder. In some embodiments, a ratio of T to ST in plasma or serum of less than about 0.05, about 0.04 or about 0.03 indicates that the subject does not have a cardiovascular disorder. In this context, "about" indicates within about 0.005.

In some specific non-limiting examples, the biological sample is a serum or plasma sample. In other embodiments, the biological sample is a heart tissue sample or a sample that includes blood vessels.

In some embodiments, the methods also include administering to the subject a therapeutic agent for the treatment of the cardiovascular disorder associated with oxidative stress, such as if the ratio of T to ST in a serum or plasma sample from the subject is greater than about 0.051 to greater than about 0.062, greater than about 0.052 to greater than about 0.06, greater than about 0.058 to greater than about 0.062, such as about 0.052 or greater, about 0.053 or greater, about 0.054 or greater, about 0.055 or greater, about 0.056 or greater, about 0.057 or greater, about 0.058 or greater, about 0.059 or greater, or about 0.06 or greater. Suitable therapeutic agents are disclosed above. In specific non-liming examples, the subject has heart failure or atheroscleoric cardiovascular disease. In other non-limiting examples, the subject has myocardial infarction, ischemic heart disease, stroke, or peripheral arterial disease. In further non-limiting examples the subject has cardiac function associated with a hyposialylation disorder, such as GNE myopathy.

A ratio of T to monosialylated ST (T/ST) can also be measured in biological samples other than serum or plasma, including, but not limited to platelets, red cells, white cells, cerebrospinal fluid, cell extracts (such as cell culture extracts) urine or a biopsy sample, such as a cardiac biopsy. In some embodiments, T and monosialylated ST are measured in biological samples from subjects known not to have the cardiovascular disorder associated with oxidative stress, and a control ratio of the T to ST is established.

T and ST are measured in a biological sample from a subject of interest, to determine if the subject has the cardiovascular disorder associated with oxidative stress. In some embodiments, a T to ST ratio of greater than two standard deviations greater than the control ratio of T to ST diagnoses the cardiovascular disorder associated with oxidative stress. In additional embodiments, a ratio of T to ST of greater than three standard deviations than the control ratio of T to ST diagnoses the cardiovascular disorder associated with oxidative stress. In some embodiments, the methods also include administering to the subject a therapeutic agent for the treatment of the disorder associated with oxidative stress, such as if the T to ST in a tissue sample other than serum or plasma is greater than two standard deviations, such as three standard deviations greater than the ratio of T to ST for the control, such as the mean T/ST ratio for biological samples from subjects without the disorder associated with oxidative stress (and/or without any disorder associated with oxidative stress). Suitable therapeutic agents are disclosed herein.

Methods are also disclosed herein for determining the effectiveness of a first dosage, or the duration of a dosage, of a therapeutic agent for treatment of a cardiovascular disorder associated with oxidative stress in a subject. The method can determine if a therapeutic agent of interest is of use for treating the cardiovascular disorder associated with oxidative stress in a subject, or if the therapeutic agent has been administered for a sufficient period of time to treat the subject. The methods can be used to determine the lowest effective therapeutic dosage of an agent for the treatment of a subject. These methods include measuring monosialylated ST antigen and T antigen in a biological sample from the subject administered the therapeutic agent. In some embodiments, the methods include administering the therapeutic agent to the subject. The ratio of T to monosialylated ST is determined.

In some embodiments, a ratio of T to ST in a plasma or serum sample of less than about 0.06, less than about 0.059, less than about 0.058, less than about 0.057, less than about 0.056, less than about 0.054, less than about 0.053, less than about 0.052, or less than about 0.051 indicates that the first dosage of the therapeutic agent is effective for the treatment of the cardiovascular disorder associated with oxidative stress, and/or that the therapeutic agent has been administered for a sufficient duration of time to treat the subject. In additional embodiments, a ratio of T to ST of less than about 0.05, about 0.04 or about 0.03 indicates that the first dosage of the therapeutic agent is effective for the treatment of the cardiovascular disorder associated with oxidative stress, and/or that the therapeutic agent has been administered for a sufficient duration of time to treat the subject. Biological samples other than serum or plasma can also be used.

In additional embodiments, a ratio of T to ST of greater than about 0.051, greater than about 0.052, greater than about 0.053, greater than about 0.054, greater than about 0.055, greater than about 0.056, greater than about 0.057 or greater, greater than about 0.058, greater than about 0.059, or greater than about 0.06, such as in serum or plasma, indicates that the first dosage of the therapeutic agent is not effective for the treatment of the cardiovascular disorder associated with oxidative stress and/or that the therapeutic agent has not been administered for a sufficient duration of time to treat the subject. In some embodiments, a serum or plasma T/ST ratio of greater than about 0.07, about 0.08, about 0.09, or about 0.1 indicates that the first dosage of the therapeutic agent is not effective for treating the subject, and/or that the therapeutic agent has not been administered for a sufficient duration of time to treat the subject. Biological samples other than serum or plasma can also be used. In some non-limiting examples, for any of the methods disclosed herein, the biological sample can be a sample other than serum or plasma.

In some embodiments, a ratio of T to monosialylated ST of at least two standard deviations less than a control ratio of T to ST indicates that the first dosage of the therapeutic agent is effective for the treatment of the cardiovascular disorder associated with oxidative stress and/or that the therapeutic agent has not been administered for a sufficient duration of time to treat the subject. In yet other embodiments, a ratio of T to monosialylated ST of at least three standard deviations less than a control ratio of T to ST for a control indicates that the first dosage of the therapeutic agent is effective for the treatment of the cardiovascular disorder associated with oxidative stress and/or that the therapeutic agent has been administered for a sufficient duration of time to treat the subject. In further embodiments, the control ratio is the mean ratio of T to ST in biological samples from subjects that do not have the cardiovascular disorder associated with oxidative stress. The biological sample can be any biological sample of interest, such as blood, an extract from a biopsy, such as an extract of platelets, white blood cell, red blood cells, kidney cells, muscle cells, heart cells, brain cells, lung cells, or liver cells. The biological sample can be urine or cerebrospinal fluid.

In certain aspects, these assays are performed at a diagnostic laboratory, and the information is then provided to the subject or a physician or other healthcare provider. In some embodiments, the dosage of the therapeutic agent is decreased, and a second lower dosage of the therapeutic agent is administered to the subject. In additional embodiments, these methods can be used to determine the lowest effective dosage of the therapeutic agent of use to treat the subject. In yet other embodiments, the dosage of the therapeutic is increased and administered to the subject. In other examples, and additional dosage of the therapeutic agent is administered to the subject.

Thus, in additional embodiments, the method can include administering to the subject a second dosage of the therapeutic agent, wherein the second dosage is the same, greater, or less than the first dosage of the therapeutic agent. Monosialylated ST antigen and T antigen are measured in a biological sample from the subject, and the ratio of T to ST is determined.

In some embodiments, a ratio of T to monosialylated ST in serum or plasma samples of less than about 0.0521, less than about 0.052, less than about 0.053, less than about 0.054, less than about 0.055, less than about 0.056, less than about 0.057, less than about 0.058, less than about 0.059, or less than about 0.06, indicates that the second dosage of the therapeutic agent is effective for the treatment of the cardiovascular disorder associated with oxidative stress and/or has been administered for a sufficient duration. In some embodiments, a ratio of T to ST of less than about 0.05, about 0.04 or about 0.03 in the plasma or serum sample indicates that the second dosage of the therapeutic agent is effective for the treatment of the cardiovascular disorder associated with oxidative stress and/or has been administered for a sufficient duration. A ratio of T to ST of greater than about 0.051, greater than about 0.052, greater than about 0.053, greater than about 0.054, greater than about 0.055, greater than about 0.056, greater than about 0.057 or greater, greater than about 0.058, greater than about 0.059, or greater than about 0.06 in the plasma or serum sample indicates that the second dosage of the therapeutic agent is not effective for the treatment of the cardiovascular disorder associated with oxidative stress and/or has not been administered for a sufficient duration. In other embodiments, a ratio of T to ST of greater than about 07, about 0.08, about 0.09, or about 0.1 in the plasma or the serum sample indicates that the second dosage of the therapeutic agent is not effective for the treatment of the cardiovascular disorder associated with oxidative stress. Thus, in some embodiments, the methods disclosed herein can be repeated to determine the lowest dosage of an agent that is effective for the treatment of the subject. Biological samples other than serum or plasma can also be used.

In some embodiments, in other samples than plasma or serum, a ratio of T to monosialylated ST of at least two standard deviations less than a control ratio of T to ST for a control indicates that the second dosage of the therapeutic agent is effective for the treatment of the cardiovascular disorder associated with oxidative stress and/or is administered for a sufficient duration to treat the subject. In yet other embodiments, a ratio of T to monosialylated ST of at least three standard deviations less than a control ratio of T to monosialylated ST for a control indicates that the second dosage of the therapeutic agent is effective for the treatment of the cardiovascular disorder associated with oxidative stress and/or that the therapeutic agent has been administered for a sufficient duration of time to treat the subject. In further embodiments, the control ratio is the mean ratio of T to monosialylated ST in biological samples from subjects that do not have the cardiovascular disorder associated with oxidative stress. Thus, the methods can be repeated to determine the lowest dosage of an agent that is effective for the treatment of the subject. The biological sample can be any biological sample of interest, such as an extract from a tissue biopsy, such as an extract of platelets, white blood cell, red blood cells, kidney cells, muscle cells, heart cells, brain cells, lung cells, or liver cells. The biological sample can be blood, urine or cerebrospinal fluid.

The methods can be repeated 1, 2, 3, 4, 5, 6, 7, 8, 9, 10 or more times to determine the lowest dosage of a therapeutic agent that is effective for treating the subject, and/or the shortest duration of administration that is effective for treating the subject. The methods can also be used over the course of a therapeutic regimen to monitor the efficacy of a therapeutic agent for the treatment of the subject.

The disclosed methods can include comparing the ratio of T to monosialylated ST to a control. The control can be a standard value, or the ratio of T to monosialylated ST in a biological sample from a subject known not to have the disorder associated with oxidative stress For any and all of the methods disclosed herein, the cardiovascular disorder associated with oxidative stress can be any disorder of interest. In some embodiments, the disorder is associated with hyposialylation in the cardiac or vascular tissue. The disorder can be heart failure or atheroscleoric cardiovascular disease. In additional embodiments, the disorder is myocardial infarction, ischemic heart disease, stroke, or peripheral arterial disease.

In further embodiments, the subject does not have GNE myopathy. Thus, in some examples, the subject has a cardiovascular disorder associated with oxidative stress, but does not have GNE myopathy. In other examples, the subject has a vascular or cardiac disorder is associated with hyposialylation, such as hyposialylation in the cardiac or vascular tissue, but does not have GNE myopathy.

The method can include purifying O-glycans from the biological sample. Thus, the method can include releasing O-glycans, such as by treating the biological sample with sodium hydroxide and sodium borohydrate. Suitable concentrations of sodium hydroxide and sodium borohydrate are, for example, about 1M sodium borohydrate in 0.05M sodium hydroxide. In some embodiments, O-glycans are purified from the biological sample. Methods for purifying O-glycans include organic solvent extraction with methanol, and ion-exchange chromatography, such as with AG 50W-X8 resin (Bio-Rad, Hercules, Calif.). Exemplary non-limiting methods are disclosed in the examples section.

Disclosed herein are methods of detecting biomarkers for a cardiovascular disorder associated with oxidative stress in order to detect the cardiovascular disorder associated with oxidative stress or to determine if a therapeutic agent is effective for the treatment of this disorder. The monosialylated ST antigen and T antigen biomarkers may be detected using any means known to those of skill in the art, including the use of antibodies that specifically bind T antigen, antibodies that specifically bind ST antigen (see, for example, Cao et al. *Histochem. Cell Biol.* 106, 197-207 (1996)), and/or the use of lectins that bind T and/or ST antigen, see for example, Almogren et al. *Front Biose S*4: 840-863 (2012), incorporated herein by reference. These methods include fluorescence activated cell sorting (FACS) and enzyme linked immunosorbent assays (ELISA), Western blotting and 2D gel electrophoresis. These methods can utilize both lectins and antibodies; suitable antibodies are disclosed, for example, in Published U.S. Patent Application No. 2012/0294859. In some embodiments, these methods are used to detect monosialylated ST antigen and T antigen on white blood cells, platelets, red blood cells, or other tissues. Generally, the monosialylated ST antigen and T antigen biomarkers are quantitated.

In particular disclosed embodiments of the method, the biomarkers are detected as a ratio using mass spectrometry. Any mass spectrometry technique known to those of ordinary skill in the art to be suitable for analyzing biological molecules can be utilized. For example, mass spectrometric techniques contemplated herein include mass spectrometry techniques using various ionization techniques (such as, but not limited to, matrix-assisted laser desorption/ionization (MALDI), electrospray, thermospray, and the like) coupled with one or more mass analyzer components (such as, but not limited to, time-of-flight 66BTOF], quadrupole, and ion traps). Any of the mass spectrometry detection methods used herein, may also be modified to perform tandem mass spectrometry, and/or may be modified to employ additional analytical techniques, such as liquid chromatography, gas chromatography, and ion mobility.

Mass spectrometry has been used as a powerful tool to characterize polymers such as glycans because of its accuracy (.+−.1 Dalton) in reporting the masses of fragments generated (e.g., by enzymatic cleavage), and also because only pM sample concentrations are required. For example, matrix-assisted laser desorption ionization mass spectrometry (MALDI-MS) has been described for identifying the molecular weight of polysaccharide fragments in publications such as Rhomberg et al. *PNAS USA* 95, 4176-4181 (1998); Rhomberg et al. *PNAS USA* 95, 12232-12237 (1998); and Ernst et al. *PNAS USA* 95, 4182-4187 (1998). Other types of mass spectrometry known the art, such as electron spray-MS, fast atom bombardment mass spectrometry (FAB-MS) and collision-activated dissociation mass spectrometry (CAD) can also be used. However, the disclosed methods are not limited to the use of mass spectrometry. Other methods of use include, but are not limited to, capillary electrophoresis (CE), NMR, and HPLC with fluorescence detection.

The techniques, including mass spectrometry techniques disclosed herein may be used to determine the ratio of biomarkers present in a biological sample. For example, particular embodiments concern the core1 monosialylated ST antigen and the T antigen. The ratio of these two antigens within a particular biological sample may be determined by using the disclosed mass spectrometry techniques to produce one or more ions identifying the particular antigen. For example, a sample may be added to a mass spectrometer, which promotes fragmentation of the components within the sample to produce various different ions associated with each component.

Multiple reaction monitoring may be used to produce a unique fragment ion that can be monitored and quantified. In particular disclosed embodiments, the parent mass of the compound is specified and the sample comprising the compound is monitored for the unique fragment ion. Typically, the parent mass/ion of the compound is selected and fragmented and either a particular fragment, the unique fragment ion, is analyzed or all fragments from the parent ion are analyzed. The ratio of each compound can be determined using quantitative mass spectrometry, such as by using an internal standard. In particular disclosed embodiments, the monosialylated ST and T antigen have different mass transitions, which can be determined in order to quantify the ratio of the two antigens in a biological sample. Typically, the monosialylated ST antigen will have a parent mass (or parent ion m/z) of 895 and the fragment ion is 520. The T antigen can have a parent mass (or parent ion m/z) of 534 and the fragment ion is 298. The concentration of each of the monosialylated antigen and the T antigen can be measured by comparing the signals from the internal standard with that produced by either the ST or T antigens. In particular disclosed embodiments, one or more calibration curves may be produced using various different concentrations of either antigen.

According to one embodiment of the disclosed methods, a biological sample (e.g., a blood sample, plasma sample, tissue extract etc.) is collected and prepared for analysis. As an example, an internal standard may be added to the biological sample in solution (e.g., aqueous solution). The biological sample may then be treated with a buffered base solution (e.g., an aqueous solution of sodium borate and sodium hydroxide) in order to promote denaturation of the serum proteins. The solution may be neutralized using an appropriate neutralizing solution (e.g., acetic acid in methanol), and the desired glycans extracted using methanol. The extracted glycans may be desalted using an ion exchange resin and then dried.

Once the desired biological sample is obtained, it may be manipulated in order to promote analysis using the disclosed mass spectrometric method. In particular disclosed embodiments, desalted glycans may be permethylated using a base and appropriate methylating agent. Solely by way of example, the glycan may be exposed to an aqueous solution of sodium hydroxide in dimethylsulfoxide (DMSO) and then treated with methyl iodide. After extraction, the permethylated glycans are purified, such as by a SPE C18 column, and used in the disclosed mass spectrometric analysis.

According to one embodiment, the permethylated glycans are analyzed using tandem mass spectrometry coupled with high-performance liquid chromatography (HPLC-MS/MS); however, any suitable mass spectrometric methods may be used as disclosed herein. In particular disclosed embodiments, a suitable buffer/solvent system is selected for the HPLC analysis portion of the analytical technique. For example, a two-buffer system may be used. Particular disclosed embodiments concern using a first buffer of acetonitrile/formic acid/water having ratios of 1:0/1:99 (v:v:v), respectively, and a second buffer of acetonitrile/formic acid/water having ratios of 99:0/1:1 (v:v:v), respectively. Exemplary flow rate protocols are provided herein. In particular disclosed embodiments, mass spectrometry analysis is conducted using an enhanced product ion source in the positive mode and one or more quadrupole mass analyzers. Exemplary non-limiting methods are disclosed in PCT Application No. PCT/US2014/025633, which is incorporated by reference herein.

EXAMPLES

GNE myopathy, which is also known as distal myopathy with rimmed vacuoles or hereditary inclusion body myopathy, is a debilitating, autosomal recessive myopathy due to mutations in GNE, a gene that encodes critical enzymes in sialic acid biosynthesis. It is clinically characterized by skeletal muscle atrophy and weakness that preferentially involve the distal muscles. It was demonstrated that sialic acid deficiency is a key factor in the pathomechanism of GNE Myopathy, since prophylactic sialylation-increasing therapies prevented the onset of muscle athrophy and weakness in this animal model. However, there was an unexplained link between hyposialylation due to GNE mutations and the pathognomonic findings in the muscle. The GNE Myopathy mice muscle disease presents in early stages as muscle atrophy, which in later stages progressively contributes to muscle weakness and degeneration. Several phenomena were examined that could possibly contribute to the muscle atrophy in GNE Myopathy muscles. It was found that reactive oxygen species (ROS) generation is increased in both in vitro and in vivo models of GNE Myopathy and an antioxidant, N-acetylcysteine, successively ameliorated myopathic phenotypes of GNE Myopathy mice. This implicates that GNE mutation may induce oxidative stress in GNE myopathy skeletal muscle tissue and that excessive produced ROS were scavenged by NAC therapy and prevent severe myopathic features from developing. These findings also implicate that sialylation-increasing therapies, previously shown to ameliorate myopathic phenotypes of GNE Myopathy mice may actually function as antioxidant therapy. Previous in vitro studies suggested antioxidant features of sialic acid.

As disclosed herein, cardiac impairment is prevalent in GNE myopathy patients. Therefore a systematic evaluation was performed of the cardiac involvement in GNE myopathy by analyzing the mouse model Gne–/–hGNED176VTg. Cardiac function testing on GNE myopathy mice (Gne–/–hGNED176VTg), including MRI and ECG imaging, showed that GNE myopathy mutant mice have decreased cardiac output, and increased end-diastolic and end-systolic volumes. These finding suggest that GNE myopathy mutant mice have restrictive cardiomyopathy. Moreover, hyposialylation of left ventricular cardiac muscle was demonstrated. These findings suggest that the cardiac muscle pathology in GNE myopathy is similar to its skeletal muscle pathology. Antioxidant therapy and/or sialylation-increasing therapies can be used to treat he skeletal muscle impairment as well as the cardiac impairment of GNE myopathy patients. In addition, antioxidant therapies and/or sialylation-increasing therapies can be of use in related disorders with reactive oxygen species, such as vascular disorders and myocardial disease.

Example 1

Materials and Methods

Mice: Generation of Gne-knockout mice that express the human GNE mutation D176V (Gne$^{-/-}$hGNED176V-Tg) was described previously (Malicdan et al., Hum Mol Genet. 2007; 16:2669-2682). Same line of GNE Myopathy mice (Gne$^{-/-}$-hGNED176V-Tg) and littermate mice (Gne$^{+/-}$hGNED176V-Tg) as controls were used throughout the study.

Quantitative RT-PCR and microarray analysis: Total RNA was extracted from triceps brachii muscles using TRIZOL® reagent and subsequently treated with DNase I (Invitrogen). cDNA was synthesized using SUPERSCRIPT® VILO™ cDNA Synthesis Kit (Invitrogen).

Microarray experiments were carried out using a CODELINK™ Mouse Whole Genome Bioarray (Applied Microarrays Inc.) at Filgen Inc. The arrays were scanned using a GENEPIX®4000A Array Scanner (Molecular Devices Inc.). The data were analyzed by using Microarray Data Analysis Tool version 3.2 (Filgen Inc.).

For quantitative PCR, TAQMAN® probes were used in combination with the TAQMAN® Gene Expression Master Mix (Applied Biosystems) in a total reaction of 20 µl. STEPONEPLUS™ Real-Time PCR System (Applied Biosystems) was used to quantify mRNA expression. mRNA relative expression was normalized to internal control (GAPDH) and determined as fold change in the average expression value of littermate muscles. The TAQMAN® probes used were as follows: F-box protein 32 (Fbxo32), Mm00499523_m1; tripartite motif-containing 63 (Trim63), Mm01185221_m1; Sulfiredoxin1 homolog (Srxn1), Mm00769566_m1; metallothionein 1 (Mt1), Mm00496660_g1; metallothionein 2 (Mt2), Mm00809556_s1; metallothionein 3 (Mt3), Mm00496661_g1; LC3b, Mm00782868_sH.

In vivo hydroxyl radical measurement: Hydroxyl radicals in living mice muscles were measured by salicylate trapping method combined with microdialysis (Close et al., Free Radic Biol Med. 2005; 39:1460-14671; Patwell et al., Free Radic Biol Med. 2001; 30:979-985). 2,5-dihydroxybenzoic acid (2,5-DHBA) generated from the salicylate in the microdialysis fluids were measured as an index of reaction with hydroxyl radicals (Richmond et al., Anal Biochem. 1981; 118:328-335). Anesthesia was induced in mice with intraperitoneal sodium pentobarbital (50 mg per kg body weight) and was maintained with supplemental doses. Microdialysis probes OP-100-075 (Eicom) were placed into the gastrocnemius muscle of the left limb and perfused with 5 mM salicylate in Ringer's solution (8.6 g NaCl, 0.25 g CaCl$_2$ and 0.3 g KCl in 1 liter of ultra pure water) at a flow rate of 1 µl/min. All the liquid flow lines were shielded from light exposure to avoid oxidation. Microdialysates were collected every 20 min resulting in a total of 20 µl of dialysate per collection. Following 80 to 100 min of baseline microdialysis collections, the left gastrocnemius muscles were subjected to contract by electrical stimulation of surface electrodes. Muscles were stimulated to contract at 40 Hz with 3 ms pulses for 300 trains at 50 V. Following the contractions, at least 5 further 20-min microdialysate collections were taken. 2, 5-DHBAs in microdialysates were detected by HPLC-electrochemical detection system (Eicom) and the chromatograms were analyzed using PowerChrom software (eDAQ).

Cell cultures and myotubes analysis: Myocytes from Gne$^{-/-}$hGNED176V-Tg mice and littermate controls were proliferated in DMEM containing 20% fetal bovine serum and 1% chicken embryo extracts in a 5% CO$_2$ and induced to differentiation in a serum free medium, OPTIPRO™ SFM (Gibco), to make the cells hyposialylated. Where indicated, myotubes were treated with 5 mM NeuAc (Japan Food and Liquor Alliance) or 5 mM NAC (Sigma) for 72 h.

For the analysis of intracellular ROS, a popular fluorescence-based probe, 2',7'-dichlorodihydrofluorescein diacetate (DCFH-DA) (Wang et al., Free Radical Biology and Medicine. 1999; 27:612-616; Halliwell and Whiteman, Br J Pharmacol. 2004; 142:231-255) was used. Cells were loaded with 5 µM DCFH-DA (Invitrogen) in PBS for an hour and recovered with phenol red-free DMEM (Gibco) for 30 min at 37° C. in a 5% CO$_2$ incubator. Then the cells were placed in a CYTOFLUOR® Series 4000 multi-well fluorescence plate reader (PerSeptive Biosystems) with temperature maintained at 37° C. The excitation filter was set at 485 nm and the emission filter was set at 530 nm. The fluorescence from each well was captured and recorded.

To evaluate the ROS generation under pro-oxidants, myotubes cultured in each condition were loaded with 5 µM DCFH-DA for 1 h and recovered in the different concentrations of H$_2$O$_2$ or menadione-containing medium. After 30 min incubation in dark at 37° C., the microplate containing cells with pro-oxidants were placed in a plate reader and fluorescence was captured at every 5 min until it reached a plateau. Maximum fluorescence of each well was used for analysis.

For the cell viability assay, myotubes were exposed to $H_2O_2$ for 24 h and to menadione for 6 h before staining. Nuclear staining with Hoechst 33342 (Thermo Scientific) and propidium iodide (PI) (Dojindo) was used for morphological assessment of apoptosis by fluorescence microscopy (Lee and Shacter, *Journal of Biological Chemistry*. 1999; 274:19792-19798). Minimum 200 nuclei were counted and cell viability was calculated by the exclusion of PI-stained nuclei from Hoechst 33342-stained nuclei.

N-Acetylcysteine (NAC) Treatment Protocols: $Gne^{-/-}$ hGNED176V-Tg mice were randomly divided into high dose NAC (n=13), low dose NAC (n=13), or untreated control (n=17) groups. For NAC (Sigma) treatment, mice were provided ad libitum access to drinking water containing high dose NAC (1.0% w/v) or low dose NAC (0.1% w/v), which gives an average dose of 1.5 g/kg for high dose group and of 0.15 g/kg for low dose group per day. There was no difference in water consumption between mice receiving NAC supplemented water or regular drinking water. Treatment was initiated from the average age of 26 weeks until the mice reached at least 55 weeks. Three littermates groups (high dose NAC; n=7, low dose NAC; n=7, or untreated control; n=6) were treated in the same way.

Motor performance analysis: The motor performance was evaluated using treadmill exercise as previously reported (9, 10) with minor modification. Briefly, after 7 days of acclimation on the treadmill, two exercise tests were performed on separate days. The performance test started with a speed of 10 m/min for 5 minutes and the speed was gradually increased by 10 m/min every min until the mouse was exhausted and could no longer run. The time of exhaustion was used to calculate the total distance of the mice ran during the exercise. The endurance exercise consisted of a 60-min treadmill run at 20 m/min with a 70 ° incline, during which the number of beam breaks or rests were recorded. Both tests were done twice with 2 days rest in between.

Muscle contractile properties analysis: The contractile properties of the gastrocnemius and tibialis anterior muscles were measured according to previous protocol (Malicdan et al., *Nat Med.* 2009; 15:690-695; Malicdan et al., *Physiol Genomics.* 2008; 35:106-115). After the mouse was anesthetized with intraperitoneal sodium pentobarbital (50 mg per kg body weight), the entire skeletal muscles were isolated along with the proximal bone of origin intact. Then the muscle was mounted in a vertical chamber and connected to a force-displacement and length servo system. Square wave pulses 0.2 ms in duration were generated by a stimulator and amplified, and subsequently muscle length was adjusted to the length ($L_0$) that resulted in maximal isometric twitch force (Pt) as the muscles were bathed in a physiologic solution. With the muscle held at $L_0$ and duration changed to 3 ms, the force developed during trains of stimulation pulses (10 to 100 Hz) was recorded and the maximum absolute tetanic force (Po) was determined. Absolute force was normalized with the physiologic cross-sectional area (CSA; muscle weight divided by the product of $L_0$ and 1.066 $g/cm^3$) to obtain specific force (Pt/CSA and Po/CSA).

Fiber diameter analysis: Muscle tissues were processed according to previous protocols (8-10). For the morphometric analysis, we stained frozen transverse sections (6 μm) of gastrocnemius muscles with rabbit polyclonal antibody to caveolin 3 (BD Transduction Laboratories), followed by Alexa fluor-conjugated goat IgG antibody to rabbit (Invitrogen). Five randomly selected images per mouse were used to measure fiber diameters using ImageJ software (NIH). Minimal inner diameters of 1,000 myofibers from each mouse were measured.

Statistics: Statistics were calculated using GraphPad Prism 5 software (GraphPad). Quantitative RT-PCR data were analyzed using Mann-Whitney test. Between-group comparison for in vivo NAC treatment was performed using one-way analysis of variance (ANOVA) with Dunnett's post-test. All values are expressed as means±SEM. We performed two-sided tests with a $p<0.05$ level of significance.

Example 2

Atrogins and Oxidative Stress Related Genes are Upregulated in the GNE Myopathy Muscles Two muscle-specific ubiquitin ligases, atrogin-1/FBxo32 and MuRF1/Trim63, are upregulated in various models of muscle atrophy (Bodine et al., *Science Signaling.* 2001; 294:1704; Gomes et al., *Proc Natl Acad Sci USA.* 2001; 98:14440-14445). Quantitative RT-PCR revealed these two skeletal muscle atrophy markers are highly expressed with a 1.8-fold increase in atrogin-1 expression and a 2.0-fold increase in MuRF1 in $Gne^{-/-}$hGNED176V-Tg mice (n=17, 58.0±0.2 wk) muscles as compared to littermates (n=6, 57.9±0.2 wk) muscles (FIG. 1A). These results are in line with myopathic phenotypes in model mice (Malicdan et al., *Physiol Genomics.* 2008; 35:106-115) and suggest that common proteolytic systems of muscle atrophy are involved in the pathomechanism of GNE Myopathy.

In order to determine the pathologic pathways related with loss of GNE function, the expression of genes expected to be deregulated in GNE Myopathy was evaluated with microarray data analysis (FIG. 1, B-E; FIG. 6, Tables 1-4).

Through genetic ontology profiling, several genes related with muscle atrophy, redox homeostasis, autophagy, and collagen organization were found that were highly expressed in GNE Myopathy (n=9, 57.7±0.1 wk) muscles when compared to littermates (n=3, 57.8±0.2 wk) muscles. Among these genes, RT-PCR verified that oxidative stress responsive genes, MTs (metallothioneins) and Srxn1 (sulfiredoxin1), were upregulated. The expression of MT1, MT2, and MT3 were increased by 3.8-, 3.4-, and 4.4-fold respectively and Srxn1 expression was 1.5-fold increased in GNE Myopathy muscles (FIG. 1A).

Example 3

Oxidative Stress is Increased in GNE Myopathy Muscles

To directly establish that oxidative stress is associated with the pathomechanism of GNE Myopathy, the levels of ROS was analyzed in skeletal muscles in vivo (FIG. 2). Baseline hydroxyl radicals in microdialysate from resting muscles were similar in both GNE Myopathy mice (2.3±0.8 pM; n=9) and littermates (2.4±1.2 pM; n=5). Then ROS production ws monitored during and after muscle contraction by electrical stimulation of gastrocnemius muscles; considerable increases of hydroxyl radicals after muscle contraction were found. Notably, the degree of ROS increments was significantly greater in GNE Myopathy mice (14.5±8.8 pM) than those in littermates (6.3±2.8 pM;

p<0.05) (FIGS. 2, C and D), implying oxidative stress is indeed increased in the affected muscles.

Example 4

Antioxidant Capacity is Impaired in Hyposialylated Myotubes of GNE Myopathy

To further explore oxidative stress and hyposialylation, intracellular ROS production was measured in cultured GNE Myopathy myotubes. Intracellular ROS generation, quantified by dichlorofluorescein diacetate (DCF-DA) labeling, was increased in GNE Myopathy myotubes compared to controls (FIGS. 3, A and B). Mean DCF fluorescence measured in GNE Myopathy was 1113±30 AFU, which was ten times higher than fluorescence measured in littermate controls (115±15 AFU, p<0.01). By giving NeuAC in the medium, the increased DCF fluorescence levels in GNE Myopathy myotubes were significantly reduced to near-normal levels (349±19 AFU, p<0.01), suggesting that sialylation is important for maintenance of the redox homeostasis in skeletal muscle cells.

Then the susceptibility of GNE Myopathy myotubes to oxidative stress when exposed to increasing concentration of pro-oxidants was investigated (FIG. 3, C-F). Exposure of cells to $H_2O_2$ (FIG. 3C) or menadione (FIG. 3D) led to increased in intracellular ADCF fluorescence (fluorescence at each concentration—fluorescence at zero concentration) in a dose dependent manner. Hyposialylated GNE Myopathy myotubes showed more accelerated increase in ADCF fluorescence levels compared to littermate cells (p<0.01). When GNE Myopathy myotubes were incubated with NeuAc containing media before and during exposure to pro-oxidants, the ADCF fluorescence increments were significantly decreased in both $H_2O_2$ and menadione (p<0.01). In the same manner, relative cell viability decreased sharply in GNE Myopathy myotubes, whereas NeuAc treated myotubes were more resistant to the same concentrations of $H_2O_2$ or menadione (FIGS. 3, E and F).

To determine whether pharmacological antioxidants are protective against oxidative stress in GNE Myopathy myotubes, cells were incubated with N-acetylcysteine (NAC); a remarkable decrease in DCF fluorescence level was found (191±10 AFU, p<0.01) (FIGS. 3, A and B). NAC also worked effectively in the high oxidative stress condition and the protective effect appeared to be more evident for menadione (FIG. 3, C-F). NAC treated GNE Myopathy myotubes showed comparable ΔDCF fluorescence and even better cell viability compared to those of littermate myotubes under menadione exposure. The data suggest that impaired antioxidant capacity possibly due to a decreased ROS scavenging activity in hyposialylated GNE Myopathy myotubes can be recovered by normalization of sialylation levels or administration of exogenous antioxidants.

Example 5

NAC Treatment Restores Muscle Weakness and Atrophy in GNE Myopathy Model Mice

To clarify the implication of impaired antioxidant capacity in the myopathic phenotype of GNE Myopathy, NAC was administered to the model mouse. GNE Myopathy mice were treated continuously from 20-35 wk to 55-57 wk of age with two doses of NAC (0.15 g/kg and 1.5 g/kg per day) and analyzed motor performance, muscle force generation, and changes in muscle histology with emphasis on myofiber atrophy.

Figure 5B:
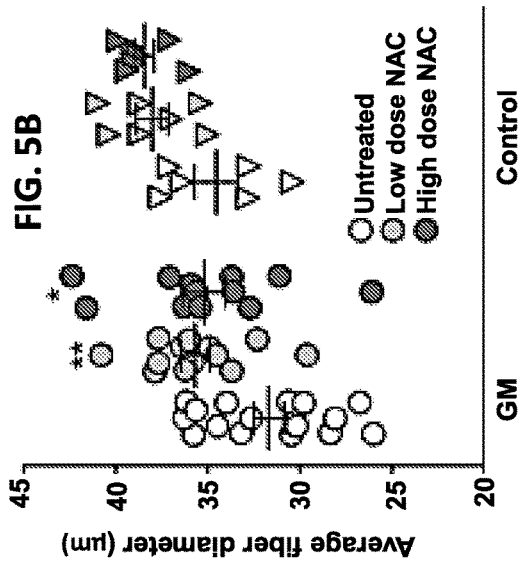
FIGS. 5A-5C. Skeletal muscle atrophy in GNE Myopathy mice was ameliorated by NAC treatment. (A) Representative sarcolemmal staining (caveolin) images from gastrocnemius muscles. (B) Muscle fiber diameters in low (light gray; n=13) and high dose (dark gray; n=13) NAC treated GNE Myopathy mice were compared to those in untreated controls (white; n=17). Data presented with mean±SEM (*P<0.05, **P<0.01). (C) Fiber diameter histogram from a mouse in each group was compared.
Figure 5A:
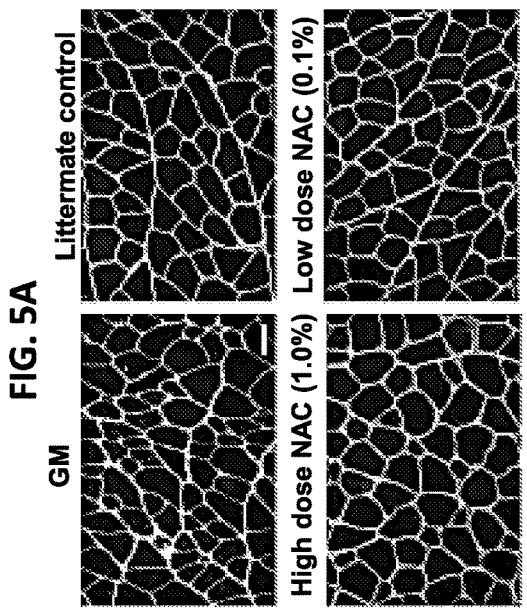
Figure 5C:
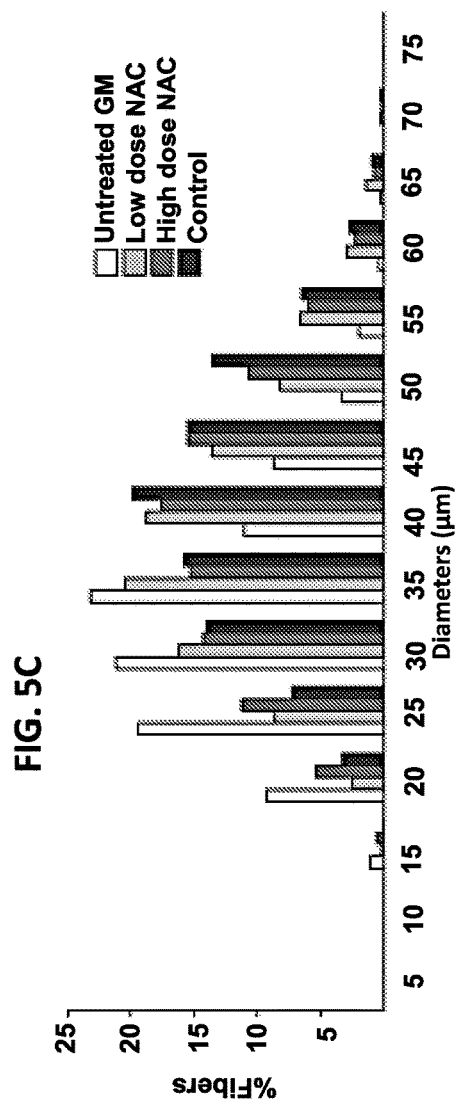

In high dose (HD) treatment group, both treadmill performance and endurance tests were significantly improved and low dose (LD) group also showed better motor function compared to untreated group (FIGS. 4, A and B). Consistently, gastrocnemius contractile properties were remarkably improved with NAC treatment. Peak isometric twitch force (Pt) and maximum tetanic force (Po) were 228.5±15.0 mN and 687.5±52.4 mN in HD group, 233.6±10.0 mN and 735.0±43.0 mN in LD group, and 167.1±6.0 mN and 526.7±24.1 mN in untreated group. Specific isometric force (Pt/CSA) and specific tetanic force (Po/CSA) increased as well in treated groups (HD: Pt/CSA=22.5±5.1 and Po/CSA=67.5±15.7 mN/mm$^2$; LD: Pt/CSA=23.4±3.3 and Po/CSA=73.5±13.5 mN/mm$^2$) compared to those in untreated GNE Myopathy mice (Pt/CSA=16.3±2.6 and Po/CSA=51.4±8.9 mN/mm$^2$). Some littermate mice also presented increased absolute contractile forces (Pt and Po) with NAC supplement (FIG. 4, C-F), but the increase was not statistically significant. With sialic acid supplement, muscle force generation in the treated mice increased in proportion to muscle fiber diameter (Malicdan et al., *Nat Med.* 2009; 15:690-69; Malicdan et al., *Physiol Genomics.* 2008; 35:106-115). To determine the effects of NAC on muscle atrophy, myofiber diameters were analyzed in gastrocnemius from the treated mice (FIG. 5B). Mean fiber diameters of NAC treated mice were significantly increased in both HD (35.2±1.2 μm, p<0.05) and LD (35.7±0.8 μm, p<0.01) groups compared to untreated group (31.7±0.8 μm). From the analysis of muscle biopsy images (FIG. 5A) and histograms of myofiber diameters (FIG. 5C), it was noted that the increase of average fiber diameters in treated mice was attributed to the decreased number of atrophic fibers.

Taken together, the data revealed the ability of NAC to recover muscle strength and myofiber size in GNE Myopathy mice. In an attempt to understand the therapeutic effects of NAC at molecular level, we then performed gene expression analysis with HD (n=6, 56.7±1.2 wk) and LD (n=6, 57.7±1.7 wk) treated muscles. As expected, the upregulation of atrogenes (atrogin-1 and MuRF1) and oxidative stress responsive genes (MT1 and MT2) in the GNE Myopathy muscle was recovered with NAC treatment (FIG. 1A). LC3b, a marker used for the presence of autophagy, was recovered as well (FIGS. 1, A and D) and β-amyloid expression by ELISA in muscle homogenates was decreased after treatment (FIG. 6).

No adverse side effects were found in long term NAC treatment. Serum aspartate aminotransferase, alkaline phosphatase, and blood urea nitrogen showed no difference between treated and untreated mice.

Thus, increased ROS was demonstrated in both in vitro and in vivo models of GNE Myopathy and proved this phenomenon is associated with cellular hyposialylation, which is a key pathogenic factor of this disease. Upregulation of ROS responsive genes such as MTs and Srxn1 suggests that the affected muscles are highly exposed to oxidative stress. Metallothioneins belong to the group of intracellular cysteine-rich proteins and the synthesis of them was known to be increased by several-fold under oxidative stress (Ruttkay et. al., *Int J Mol Sci.* 2013; 14:6044-606; Sato et al., *Free Radic Biol Med.* 1993; 14:325-337). Sulfiredoxin1 is an endogenous antioxidant protein that was initially identified by its $H_2O_2$-induced upregulation (Biteau et al., *Nature.* 2003; 425:980-984) and a recent study showed that Sulfiredoxin1 is critical to maintaining redox balance in cells, especially under exposure to low steady-state levels of $H_2O_2$ (Baek et al., *J Biol Chem.* 2012; 287:81-89). It is shown herein that contraction induced ROS increment was remarkable in the GNE Myopathy muscles, suggesting that the ROS increase may either be a consequent of muscle contraction or caused by decreased overall antioxidant capacity in hyposialylated muscles. In the cell culture experiments, however, acceleration in ROS increase was noted with the same amount of $H_2O_2$, indicating the reduction of ROS scavenging capacity in GNE Myopathy myotubes. Based on the data, it can be implicated that chronic deregulation of redox homeostasis in hyposialylated muscles directs cells into a catabolic state and ultimately leads to muscle atrophy in GNE Myopathy. The fact that the effect of NAC treatment and NeuAc treatment similarly reduces oxidative stress likely supports the antioxidant property of sialic acid.

The role of oxidative stress in disease has been described in other muscle diseases. In muscular dystrophy, deregulated ROS production might be caused by constitutive defects or tissue responses to the primary pathology (Menazza et al., *Hum Mol Genet.* 2010; 19:4207-4215; Tidball and Wehling-Henricks, *Journal of Applied Physiology.* 2007; 102:1677-1686; Lawler, *Journal of Physiology*-London. 2011; 589: 2161-2170; Terrill et al., *Neuromuscul Disord.* 2012; 22:427-434). In contrast, deregulated ROS production in GNE Myopathy is not a consequence of tissue injury, but rather an upstream phenomenon to muscle atrophy. Regardless of the primary etiology and mechanism of disease, however, increased radical injury can trigger a vicious cycle that can amplify or accelerate disease progression and thus remains as a common and rational therapeutic target in diseases of skeletal muscle.

From these results, NAC can ameliorate myopathic phenotypes of GNE Myopathy model mice. As NAC has free radical scavenging properties and is able to increase the pool of glutathione in the body, it has been regarded as a powerful antioxidant (Aruoma et al., *Free Radical Biology and Medicine.* 1989; 6:593-597; Zafarullah et al., *Cellular and Molecular Life Sciences CMLS.* 2003; 60:6-20; Cotgreave, *Advances in Pharmacology.* 1996; 38:205-227; Parasassi et al., *Scientific World Journal.* 2010; 10:1192-1202). In the skeletal muscle, it has been reported that NAC can protect an isolated muscle preparation from contraction-induced oxidative stress (Sandstrom et al, *J Physiol.* 2006; 575:251-262) and can inhibit muscle fatigue in humans (Reid et al., *Journal of Clinical Investigation.* 1994; 94:2468). In the current study, decreased expression of oxidative stress responsive genes in NAC treated mice suggests that NAC is able to counteract the oxidative stress in GNE Myopathy muscles.

The improvement of muscle atrophy and force generation with NAC treatment supports the hypothesis that ROS are associated with muscle atrophy and weakness in GNE Myopathy. The muscle force generation in NAC treated GNE Myopathy GM mice was very similar to littermates, supporting the theory that muscle force generation is proportional to and influenced by myofiber diameter (Malicdan et al., *Physiol Genomics.* 2008; 35:106-115). On the other hand, even after corrected with CSA, contractile forces of untreated GM mice were still lower than those of littermates, suggesting the existence of other factors contributing to muscle weakness in GM mice. Structural changes including intracellular protein deposits and rimmed vacuoles formation start to affect muscle contraction after 40 weeks of age in GM model mice (Malicdan et al., *Physiol Genomics.* 2008; 35:106-115). The data disclosed herein suggest that the abnormalities in muscle pathology, which appeared in advanced stages of GM, are associated with oxidative stress, and can be prevented by NAC treatment. Decrease of β-amyloid expression by ELISA and LC3b expression by RT-PCR and microarray after NAC treatment in this study provides additional evidence relating to redox imbalance to autophagy deregulation which is important in the pathomechanism of various rimmed vacuolar myopathies (Kiffin et al., *Antioxidants & redox signaling.* 2006; 8:152-162; Mammucari et al., *Cell metabolism.* 2007; 6:458-471; Tresse et al., IBMPFD. *Autophagy.* 2010; 6:217-227; Malicdan et al., *Autophagy.* 2007; 3:396-398).

NAC supplement also increased average fiber diameters and absolute contractile forces in some healthy control mice. A possible explanation for this finding is that NAC has a preventive effect on age-related redox imbalance and associated sarcopenia in littermate mice. Skeletal muscle is known to be particularly affected by age-related loss of function, to which the oxidative stress has been claimed to be relevant (Terman and Brunk, *Experimental gerontology.* 2004; 39:701-705; Cadenas and Davies, *Free Radic Biol Med.* 2000; 29:222; Bonetto et al., *Free Radic Biol Med.* 2009; 47:906-916).

Although the relation between sialic acid and oxidative stress has not been completely clarified, few studies infer to the roles of sialic acid in redox balance as ROS scavenger or by reciprocal action with glycoproteins. It has been shown that sialic acid has a biologic function as direct scavenger of radicals such as $H_2O_2$ (Iijima et al., *FEBS Lett.* 2004; 561: 163-166; Ogasawara et al., *FEBS Lett.* 2007; 581:2473-2477). Moreover, it has been found that non-reducing sialic acid residue can be a target of ROS and the sialic acid content of some glycoproteins are apparently linked with oxidative stress (Goswami et al., *Clin Chim Acta.* 2003; 337:163-168; Rajendiran et al., *Am J Trop Med Hyg.* 2008; 79:372-377). One of those glycoproteins being associated with diseases of free radical etiology is transferrin, a metal binding monomeric protein, of which the degree of sialylation has been suggested to play a role in the pathophysiology of Parkinson's disease and Alzheimer's disease (van Rensburg et al., *Metab Brain Dis.* 2004; 19:89-96; van Kamp et al., *Clin Chim Acta.* 1995; 235:159-167). The results disclosed herein support an important biologic function of sialic acid, i.e., its antioxidative activity, especially in a GM, a disease with a hyposialylation as a primary defect.

In summary, the data presented herein provide insight into the pathomechanism of by revealing an important role of oxidative stress. Increased oxidative stress in hyposialylated muscles invariably leads to skeletal muscle atrophy and weakness in GNE Myopathy mice. The success of NAC treatment in normalizing this phenomenon suggests that a similar approach may benefit human GNE Myopathy patients.

Example 6

Cardiac Impairment in GNE Myopathy

GNE myopathy is an adult-onset distal myopathy caused by mutations in the GNE gene, which codes for a bifunctional enzyme important in sialic acid biosynthesis. GNE myopathy is characterized by gradually progressive weakness and atrophy that preferentially involves distal extremities. Muscle degeneration occurs, with accumulation of inclusion bodies and rimmed vacuoles in muscle fibers. It was found that cardiac involvement in GNE myopathy patients may have a higher occurrence than expected.

A systematic evaluation of the cardiac involvement in GNE myopathy was established by analyzing the mouse myopathy patients that are all homozygous mutated for the most prevalent GNE variant p.M712T are listed (Table 1).

TABLE 1

Cardiac features of 7 GNE myopathy patients (homozygous for the GNE p.M712T mutation).

| Patient No. | ECG | Echocardiogram | Holter monitoring |
|---|---|---|---|
| 1 | NSR, prolonged QTc > 460 msec | Normal, EF 65% | None available |
| 2 | NSR | Normal, EF 65% | None available |
| 3 | NSR | Normal, EF 60 ± 5%, tiny color flow across intra-atrial septumsuggestive of patent foramen ovale | Recorded for 25 hours, NSR with episodes of sinus tach, sinus brady and ectopic atrial rhythm. Ectopics consisted of 69 SVEs including one couplet. |
| 4 | NSR | Normal, EF 65% | Recorded for almost 45 hours, NSR with episodes of sinus tachycardia (maximum 111 bpm). Ectopics consisted of 6 SVEs. |
| 5 | Sinus bradycardia, HR 50-60 bpm. Otherwise normal ECG. On Beta blocker for HTN | Mildly dilated LA, and ascending aorta. LV normal size and systolic function. EF 65% | Recorded for 48 hours, sinus bradycardia with episodes of NSR. 4,725 ventricular ectopics, including 10 runs of idioventricular rhythm with the longest lasting 4 beats, and 42 runs of ventricular bieminy. 9 premature atrial contractions. |
| 6 | None available | Normal, EF 65% | Recorded for 21 hours, NSR with episodes of sinus bradycardia and sinustachycardia. No ectopy. |
| 7 | Sinus arrhythmia, HR 64 bpm | Normal, EF 65% | Recorded for 23 hours, NSR with episodes of sinus tachycardia (150 bpm highest) and sinus bradycardia (42 bpm lowest). 1 SVE, no ventricular ectopy. |

Abbreviations:
bpm = beats per minute;
EF = Ejection Fraction;
HR = Heart Rate;
HTN = Hypertension;
LA = Left Atrium;
LV = Left Ventricle;
NSR = Normal Sinus Rhythm;
QTc = corrected QT;
SVE = SupraVentricular Ectopic model Gne$^{-/-}$hGNED176VTg. Histopathology showed the presence of rimmed vacuoles and disorganization of cardiac myofibrils. Lectin staining array corroborated the hyposialylation of O-linked glycoproteins. Echocardiogram revealed decreased ejection fraction and fractional shortening, and increased left ventricle mass, indicating a decrease of cardiac function. These data were also confirmed by functional MRI on the mouse model.

These findings provide evidence that cardiac muscles are involved in GNE myopathy. Hyposialylation of cardiac muscles can lead to impaired cardiac muscle contractility, and can be improved with sialylation-increasing therapies. It is important for clinicians to be aware of the possible occurrence of cardiac disease in GNE myopathy, so that cardiac function can be monitored and the subjects can be treated.

Example 7

GNE Myopathy Patients with Cardiac Impairment

Although GNE myopathy is known to preferentially affect skeletal muscles, there have been a few reports demonstrating involvement of the cardiac muscles (Chai et al., Muscle Nerve. 2011 January; 43(1):133-6; Kimpara et al., Rinsho Shinkeigaku. 1993 August; 33(8):886-90). It was observed that cardiac involvement in GNE myopathy patients may have a higher occurrence than expected. To rule out the effect of different GNE mutations, cardiac findings of 7 GNE Methods:

Cardiac function data, including Holter monitoring, electrocardiograms (ECG) and echocardiograms on GNE myopathy patients were collected through the NIH clinical study (11-HG-0218; see the internet at clinicaltrials.gov/, trial NCT01417533) "A Natural History Study of Patients with GNE Myopathy."

Results:

Electrocardiogram (ECG) findings: Three out of seven patients (all homozygous mutated for GNE variant p.M712T) showed abnormal ECG findings: Patient 1 had prolonged corrected QT (QTc) of >460 msec, Patient 5 had sinus bradycardia, with a heart rate of 50-60 bpm, and Patient 7 had sinus arrhythmia with a heart rate of 64 bpm.

Echocardiogram findings: Five out of seven patients had normal echocardiogram findings, with a ejection fraction between 60% and 66%. Patient 3's echocardiogram showed tiny color flow across intra-atrial septum suggestive of patent foramen ovale. Patient 5's echocardiogram suggests mildly dilated left atrium and ascending aorta, normal left ventricle size and systolic function.

Holter monitoring findings: Based on Holter monitoring, five out of seven patients displayed arrhythmia, ranging from episodes of sinus tachycardia, sinus bradycardia, ectopic atrial rhythm, and ventricular ectopics.

GNE myopathy is known to preferentially affect skeletal muscles. These studies demonstrate that cardiac impairment in GNE myopathy is not rare, as it was recorded it in 18% of our GNE myopathy cohort. Severity of cardiac impairment in GNE myopathy varies from mild to life-threatening arrhythmias. Additionally, GNE myopathy patients can present with no apparent cardiac abnormalities at onset of disease symptoms; some developed cardiomyopathy 20-26 years after disease onset (Chai et al., Muscle Nerve. 2011 January; 43(1):133-6).

The observation of cardiac impairment in GNE myopathy was further pursued by performing cardiac function testing on newly admitted GNE myopathy patients.

The findings provide evidence that cardiac muscles are involved in GNE myopathy. It is important for clinicians to be aware of the possible occurrence of cardiac disease in GNE myopathy for careful examination of the cardiac function in patients and treatment.

Example 8

Mouse Model of GNE Myopathy Shows Hyposialylation of Cardiac Muscle

Patients with GNE myopathy are deficient in the GNE gene, encoding the key enzyme of sialic acid synthesis (Eisenberg et al., Nature Genet 2001; 29: 83-7). Skeletal muscle of GNE myopathy mice and patients show hyposialylation of muscle membrane proteins and lipids by lectin staining (Niethamer et al., Mol Genet Metab 2012; 107: 748-55; Leoyklang et al., Biomarkers Med 2014; 8: 641-52). The sialylation status of heart tissue in GNE myopathy mice was determined.

Methods:

The transgenic Gne–/–hGNED176V-Tg mouse model was sued (Malicdan et al., Hum Mol Genet 2007; 16; 2669-82). All animals were housed in a barrier-protected, specific pathogen-free-grade facility.

Mouse hearts or skeletal muscle (gluteus) were harvested and fixed in 4% paraformaldehyde for 48 hours at room temperature, dehydrated in 70% ethanol at 4° C., and paraffin-embedded for sectioning (Histoserv, Gaithersburg, Md.). Tissue sections (5 um) were stained with a variety of lectins, as previously described for mouse kidneys and muscle (Kakani et al., Am J Pathol 2012; 180: 1431-40; Niethamer et al., Mol Genet Metab 2012; 107: 748-55) as well as for GNE myopathy patients' muscle (Leoyklang et al., Biomarkers Med 2014; 8: 641-52). Lectin histochemistry was performed with fluorescein isothiocyanate (FITC) labeled lectins WGA and VVA from EY Laboratories (San Mateo, Calif.) and SNA from Vector Laboratories (Burlingame, Calif.). Each slide was also stained with the nuclear dye DAPI. Fluorescence imaging of multiple sections of heart per slide was performed under a Zeiss 510 META confocal laser-scanning microscope. All fluorescent images represent collapsed stacks of confocal Z-sections, imaged at 63× magnification.

Results:

Heart and skeletal muscle sections from GNE myopathy mutant mice (GNE –/–) and unaffected littermates (GNE+/+) were stained with 3 lectins: WGA, SNA and VVA (FIG. 7A). WGA (wheat germ agglutinin from *Triticum vulgaris*) predominantly recognizes terminal sialic acid (Neu5Ac; independent of the linkage to the underlying glycan) and N-acetylglucosamine (GlcNAc) on glycans (Sharon, J Biol Chem 2007; 282: 2753-64; Iskratsch et al., Anal Biochem 2009; 386: 133-46). SNA (elderberry bark agglutinin from *Sambucus nigra*) predominantly recognizes terminal sialic acid (Neu5Ac) in an α(2,6)-linkage with either galactose (prevalent in N-linked glycans) or with N-acetylgalactosamine (GalNAc) (found in O-linked glycans) (Iskratch et al. supra, 2009; Shibuya et al., J Biol Chem 1987; 262: 1596-601). VVA (hairy vetch agglutinin from *Vicia villosa*) predominantly binds GalNAc O-linked to serine or threonine residues of proteins (Shibuya et al., supra, 1987).

Lectin imaging studies were focused on the left ventricle, because this section of the heart is expected to be especially affected (by hyposialylation) in GNE myopathy since it is composed of thicker walls of cardiac muscle tissue and needs to produce the strongest muscle contraction force (to pump blood throughout the body), as compared to other heart compartments.

Wild type mouse hearts (GNE+/+) exhibited similar WGA staining intensities as mutant mouse hearts (GNE –/–), demonstrating equal total sialylation. However, SNA staining intensities were significantly lower in mutant (GNE –/–) hearts, indicating hyposialylation of 2,6-linked sialic acids. The WGA and SNA findings are comparable to previously described GNE myopathy human and mouse skeletal muscle lectin staining (FIG. 7B; Niethamer et al., Mol Genet Metab 2012; 107: 748-55; Leoyklang et al., Biomarkers Med 2014; 8: 641-52). VVA staining did not show an apparent difference in intensity in wild type and mutant heart; it is possible that skeletal muscle (showing intense VVA signal) is more affected/hyposialylated than heart muscle in this disease (i.e., a larger degree of desialylation of O-linked glycoproteins with a more intense VVA signal).

Thus, it was demonstrated that heart muscle, in particular cardiac muscle in the left ventricle, in GNE myopathy mice is hyposialylated in 2,6-linked sialic acids, similar to skeletal muscle tissue in GNE myopathy mice and patients. These mouse findings together with the finding of heart impairment in GNE myopathy patients indicate that hyposialyation (of predominantly 2,6-linked sialic acids) is involved in the cardiac impairment associated with GNE myopathy.

It is likely that increased oxidative stress in GNE myopathy heart tissue (as demonstrated for the muscle phenotype in GNE myopathy mice) increased local levels of reactive oxygen species (ROS). This increase could not be rescued due to a deficit of local antioxidants. It was demonstrated that antioxidant therapy could rescue the skeletal muscle impairment in GNE myopathy mice.

Figure 7B:
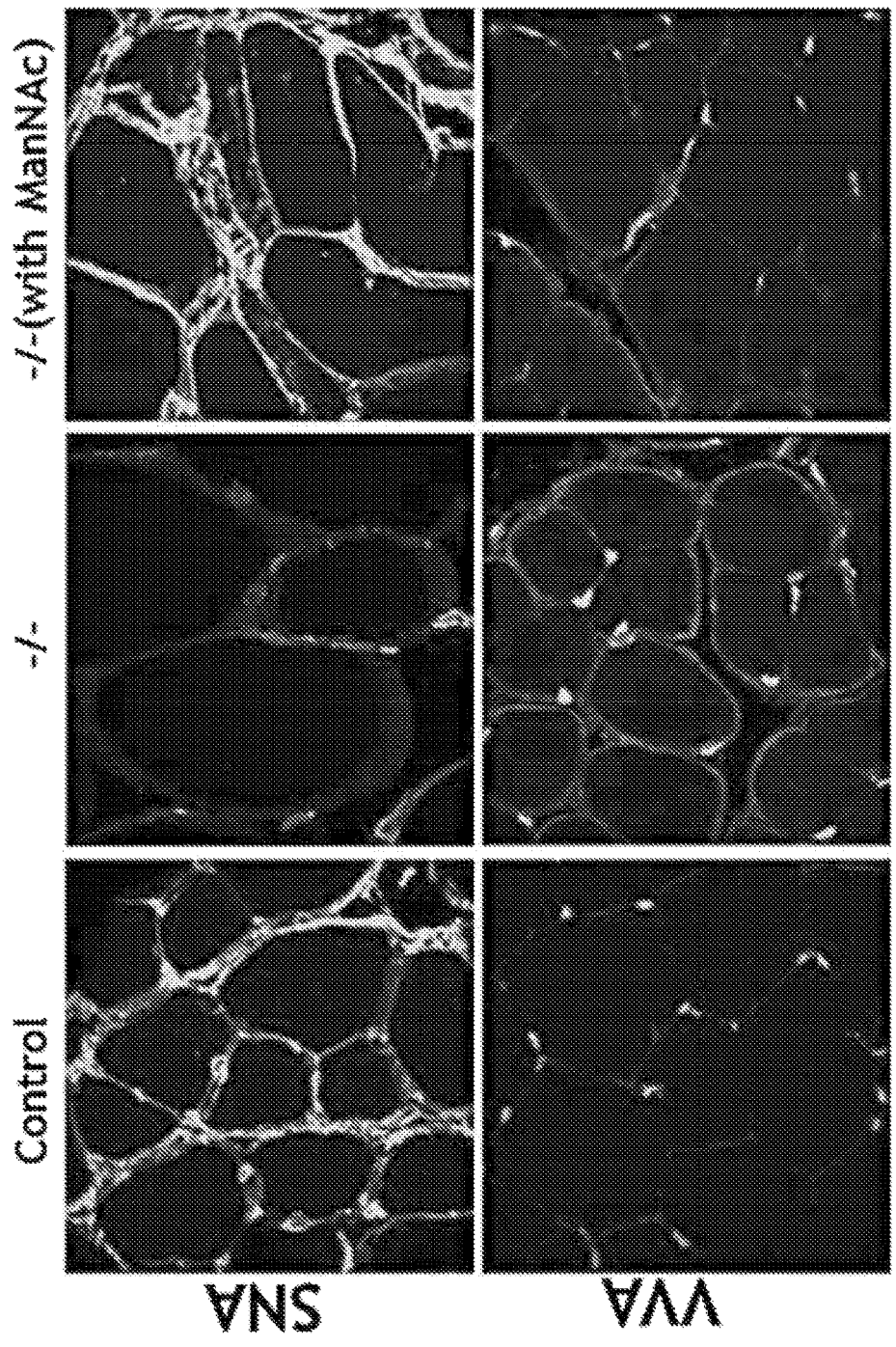
Figure 11:
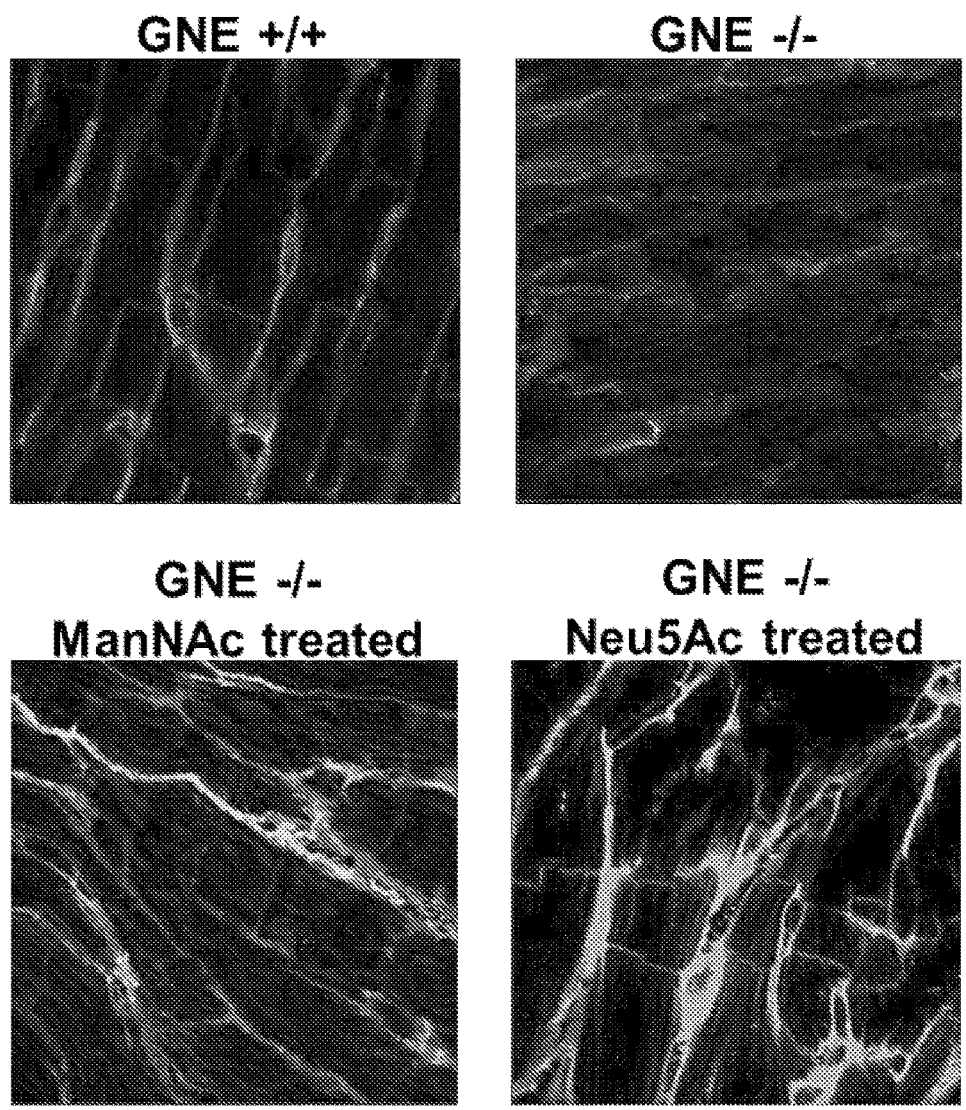
FIG. 11. Paraffin-embedded heart sections from GNE myopathy mutant mice [Gne(-/-)hGNED176V-Tg] mice (GNE (-/-) and unaffected littermates (GNE+/+) were stained with the SNA lectin informative for sialylation status (see also FIG. 7A,B).

The sialylation-increasing therapies ManNAc, sialic acid or mannosamine were shown to rescue hyposialylation of GNE myopathy mice skeletal muscle tissue (FIG. 7B; Niethamer et al., Mol Genet Metab 2012; 107: 748-55. In addition, sialylation increasing therapies ManNAc, sialic acid and sialyllactose were also able to prophylactically prevent muscle disease in GNE myopathy mice (Malicdan et al., Nature Med 2009; 15: 690-5). Sialylation-increasing therapies improve the sialylation status of GNE myopathy heart tissue (see FIG. 11), indicating resialylation of glycans in heart tissue after these sialylation-increasing therapies. This resialylation may affect the heart function.

These sialylation-increasing therapies may not only rescue heart impairment associated with GNE myopathy, but can be used to treat other cardiac impairment conditions associated with to oxidative stress that have hyposialylation of cardiac muscle. The plasma T/ST ratio (Leoyklang et al., 2014, Biomarkers Med 2014; 8: 641-52) can serve as a surrogate marker for detection of cardiac impairment associated with hyposialylation.

Example 9

Cardiac Function Testing Showed Cardiac Impairment in a Mouse Model of GNE Myopathy In the above examples, the unexpected high prevalence of cardiac impairment in GNE myopathy patients was demonstrated, and hyposialylation of heart muscle was found in a mouse model of GNE myopathy. The functional characteristics of the heart impairment of the GNE myopathy mouse model were examined using heart imaging studies.

Methods and Results:

For all heart imaging studies, the transgenic Gne-/-hGNED176V-Tg GNE myopathy mouse model was used (Malicdan et al., Hum Mol Genet 2007; 16; 2669-82; Malicdan et al., Autophagy 2007; 3: 396-8).

Figure 8A:
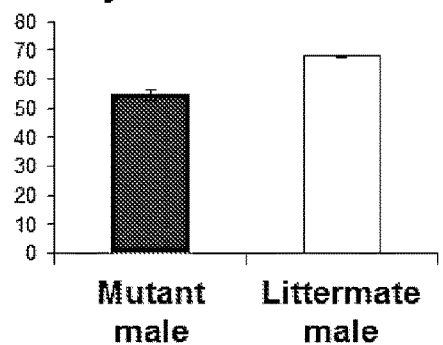
FIGS. 8A-8F: Echocardiogram findings in GNE myopathy mice. (A) GNE myopathy mutant mice [Gne(-/-) hGNED176V-Tg] showed slightly decreased ejection fractions, suggesting possibly decreased left ventricle pumping capacity. (B) GNE myopathy mutant mice showed decreased fractional shortening (the ratio between the diameter of the left ventricle when it is relaxed and its diameter when it has contracted) compared to control lieetermate mice. (C, D) GNE myopathy mutant mice displayed borderline increased left ventricle mass, implying increased wall or septal thickness. (E, F) GNE myopathy mutant mice showed increased systolic and diastolic left ventricle volumes.
Figure 8B:
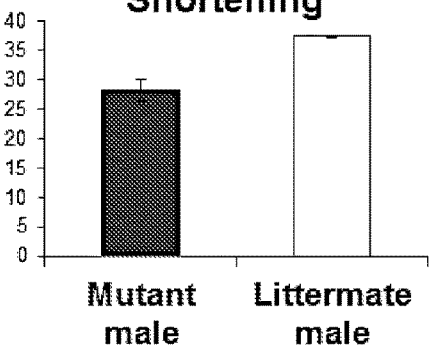
Figure 8C:
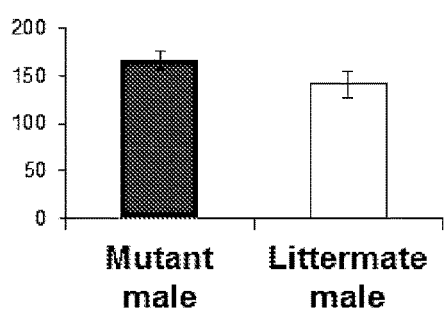
Figure 8D:
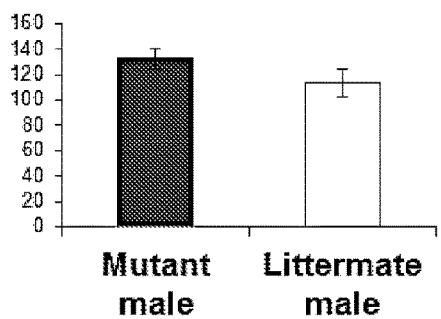
Figure 8E:
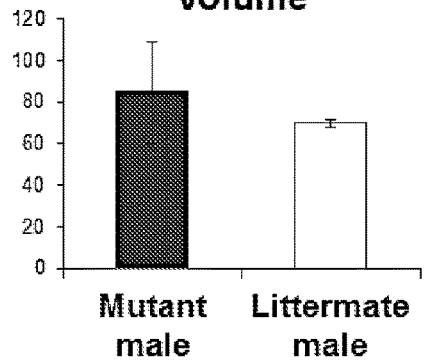
Figure 8F:
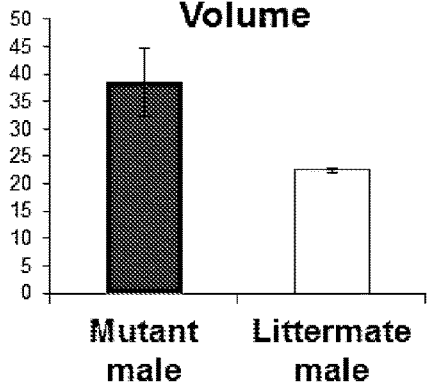

Echocardiogram findings: Echocardiogram images from GNE Myopathy and control mice were obtained using Visualsonics 2100 with LAZR. Cardiac left ventricular (LV) function was measured using B-mode and M-mode images at 40 mHz. For this procedure, the mice were anesthetized with isoflurane at 5 L/min for induction and 1.5 L/min for maintenance during echocardiogram measurements. GNE myopathy mutant mice showed slightly decreased ejection fraction (however, this was found to be normal by MRI and ECG imaging, see below), suggesting possibly decreased left ventricle pumping capacity (FIG. 8A). Mutant mice also showed slightly decreased fractional shortening (the ratio between the diameter of the left ventricle when it is relaxed and its diameter when it has contracted) compared to control mice (FIG. 8B). In addition, GNE myopathy mutant mice displayed slightly increased left ventricle mass (FIGS. 8C, 8D), implying increased wall or septal thickness. Lastly, GNE myopathy mutant mice showed slightly increased systolic and diastolic left ventricle volumes (FIGS. 8E, 8F). These echocardiogram findings in GNE myopathy mutant mice hearts were all in the minor abnormal range. More sensitive heart imaging techniques (MRI and ECG) were then utilized.

Figure 9A:
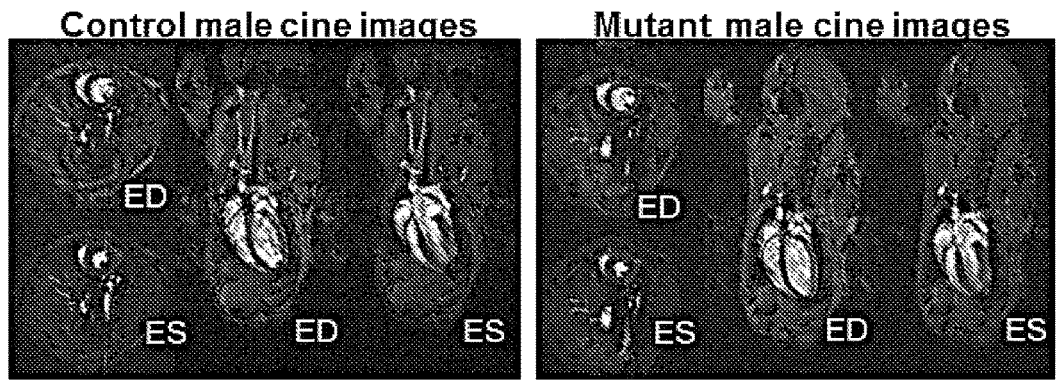
FIGS. 9A-9E. Magnetic Resonance Imaging (MRI) findings in GNE myopathy mice. (A) Still images of representative gradient echo cine scans from GNE myopathy mutant [Gne(-/-)hGNED176V-Tg] and control littermate mice hearts; both end of systole (ES) and end of diastole (ED) images are displayed. Left images: a long axis 4-chamber cine scan of the whole heart; Right images: 2D spin echo covering the chest and abdomen. (B) Mean ejection fractions calculated from MRI data showed that GNE myopathy mutant mice have ejection fraction and size within the normal range. (C) Cardiac output, calculated from MRI data was markedly decreased in GNE myopathy mutant mice compared to control. (D, E) MRI data showed slightly increased ED and ES volumes in GNE myopathy mutant mice hearts compared to control hearts.
Figure 9B:
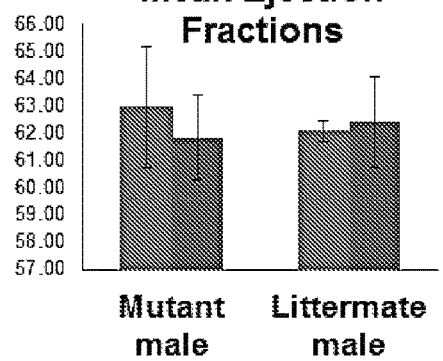
Figure 9C:
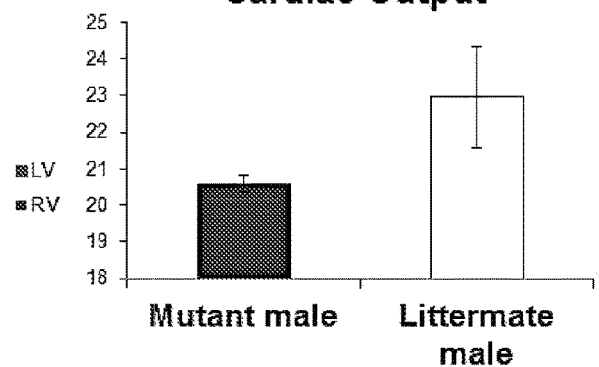
Figure 9D:
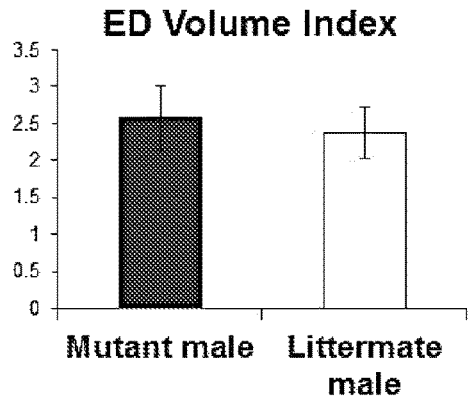
Figure 9E:
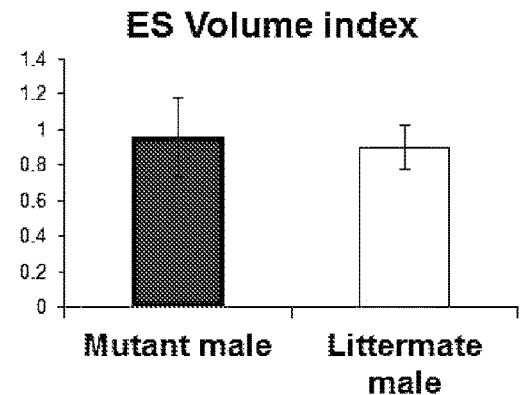

Magnetic Resonance Imaging (MRI) findings: A more sensitive test, MRI, was performed to further assess cardiac function in GNE myopathy mice. For MRI testing, the mice were anesthetized with 1-2% isoflurane and imaged on a 7T Bruker MRI system (Bruker, Billerica, Mass.) with electrocardiography (ECG) and respiratory detection. Gradient echo cine scans of the whole heart were acquired (FIG. 9A; representative still images), including Short axis cine scans (approx. 9-12 slices) covering the left ventricle in cross section from apex to base; One long axis 4-chamber cine scan; and a multislice 2D spin echo covering the chest and abdomen. MRI findings show that GNE myopathy mutant mice have ejection fraction and size within the normal range (FIG. 9B). However, GNE myopathy mutant mice showed decreased cardiac output (FIG. 9C), and slightly increased end-diastolic volume and end-systolic volumes (FIG. 9D, 9E).

Electrocardiography (ECG) findings: Both 3 and 6 leads ECG were performed on GNE myopathy mutant and control mice. ECG findings show that GNE myopathy mutant mice had an increased PR interval of 40.475 (±2.11) ms; the normal range of PR intervals is 31.7-36.5 ms. GNE myopathy mutant mice had QRS intervals within the normal range.

Cardiac function testing on GNE myopathy mice, including MRI and ECG imaging, showed that GNE myopathy mutant mice have ejection fractions and size within the normal range. However, GNE myopathy mutant mice show decreased cardiac output, and increased end-diastolic volume and end-systolic volume. These finding suggest that GNE myopathy mutant mice have restrictive cardiomyopathy in which the walls are rigid, and the heart is restricted from stretching and filling with blood properly, as opposed to hypertrophic or dilated cardiomyopathy. In restrictive cardiomyopathy, rhythmicity and contractility of the heart may be normal, but the stiff walls of the heart chambers keep them from adequately filling, reducing preload and end-diastolic volumes. Thus, blood flow is reduced, and blood volume that would normally enter the heart is backed up in the circulatory system. In time, restrictive cardiomyopathy patients develop diastolic dysfunction and eventually heart failure.

GNE myopathy skeletal muscle is pathologically characterized by the presence of rimmed vacuoles (RVs) (Malicdan et al., Autophagy 2007; 3: 396-8), which are empty spaces created by the aggregation of autophagic vacuoles. GNE myopathy skeletal muscles also are characterized by scattered small atrophic fibers, which also occasionally contain congophilic materials that are immunoreactive to b-amyloid, lysosomal proteins, ubiquitin and tau proteins. The accumulation of autophagic vacuoles in the heart muscle, similar as in skeletal muscle, might cause cardiac myocytes to be ultrastructrally abnormal and heart contractility to become severely reduced. The removal of sialic acid residues from heart tissue may play a functional role in the regulation of calcium channels (Werner et al., Biochem Pharmacol 1991; 42: Suppl S77-87); some (voltage-dependent) calcium channels play critical roles in the electro-physiology of cardiac muscle.

The results presented herein evidence that cardiac muscles are involved in GNE myopathy. It is important for clinicians to be aware of the possible occurrence of cardiac disease in GNE myopathy, examine of the cardiac function in patients, and provide proper management.

Sialic acid plays a role in cardiac function. Hyposialylation of heart tissue can cause cardiomyopathy-associated symptoms. Therapy with sialylation-increasing compounds can be used for treating group of disorders.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for treating a subject with a cardiovascular disorder associated with oxidative stress, consisting essentially of:
   selecting a subject that has the cardiovascular disorder associated with oxidative stress and has GNE myopathy; and
   administering to the subject a therapeutically effective amount of mannosamine, N-acetyl mannosamine or a derivative thereof, wherein the derivative is:

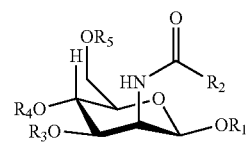

wherein: $R_1$, $R_3$, $R_4$, or $R_5$ is hydrogen, lower alkanoyl, carboxylate or lower alkyl; and $R_2$ is lower alkyl, lower alkanoylalkyl, or lower alkyl alkanoyloxy, thereby treating the cardiovascular disorder in the subject.

2. The method of claim 1, wherein the subject has heart failure, atherosclerotic cardiovascular disease, cardiomyopathy, a cardiac arrhythmia, myocardial infarction, ischemic heart disease, stroke, or peripheral arterial disease.

3. The method of claim 1, wherein the mannosamine, N-acetyl mannosamine or a derivative thereof, is microencapsulated.

4. The method of claim 1, wherein the mannosamine, N-acetyl mannosamine or a derivative thereof, is formulated in a coating, envelope or protective matrix made from a liposome.

5. The method of claim 1, wherein the mannosamine, N-acetyl mannosamine or a derivative thereof, is orally administered to the mammal.

6. The method of claim 5, wherein the mannosamine, N-acetyl mannosamine or a derivative thereof, is orally administered in the form of a food product.

7. The method of claim 1, wherein the cardiovascular disorder associated with oxidative stress is also associated with hyposialylation.

8. The method of claim 1, wherein the subject has heart damage from administration of a chemotherapeutic agent.

9. The method of claim 8, wherein the chemotherapeutic agent is doxorubicin.

10. A method for treating a subject with GNE myopathy that has impaired cardiac function, consisting essentially of:
    selecting a subject with GNE myopathy that has impaired cardiac function; and
    administering to the subject a therapeutically effective amount of mannosamine, or N-acetyl mannosamine or a derivative thereof, wherein the derivative is:

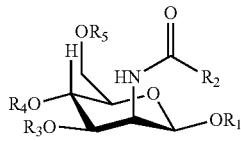

wherein: $R_1$, $R_3$, $R_4$, or $R_5$ is hydrogen, lower alkanoyl, carboxylate or lower alkyl; and $R_2$ is lower alkyl, lower alkanoylalkyl, or lower alkyl alkanoyloxy, thereby improving cardiac function in the subject.

11. The method of claim 10, further comprising
    performing a diagnostic test to determine the cardiac function of the subject.

12. The method of claim 11, wherein diagnostic test is a CT scan, cardiac catherization, coronary CT angiogram, echocardiography, ejection fraction testing, electrocardiogram, electrophysiology, exercise stress test, magnetic resonance imaging, tilt-table testing, transesphogeal echocardiogram, or an ultrasound.

13. The method of claim 10, wherein the, mannosamine, N-acetyl mannosamine or a derivative thereof, is microencapsulated.

14. The method of claim 10, wherein the, mannosamine, N-acetyl mannosamine or a derivative thereof, is formulated in a coating, envelope or protective matrix made from a liposome.

15. The method of claim 10, wherein the, mannosamine, N-acetyl mannosamine or a derivative thereof, is orally administered to the mammal.

16. The method of claim 10, wherein the mannosamine, N-acetyl mannosamine or a derivative thereof, is orally administered in the form of a food product.

17. The method of claim 10, wherein the N-acetyl mannosamine or a derivative thereof is administered at a dose of about 0.02 g/day to about 25 g/day.

18. The method of claim 1, further comprising performing a diagnostic test to determine the cardiac function of the subject.

* * * * *